United States Patent
Zhang et al.

(10) Patent No.: US 12,195,489 B2
(45) Date of Patent: Jan. 14, 2025

(54) SPIRO-BISPHOSPHOROUS COMPOUND, AND PREPARATION AND APPLICATION THEREOF

(71) Applicant: Guangdong OXO Chem Ltd., Huizhou (CN)

(72) Inventors: Runtong Zhang, Shenzhen (CN); Jianghua Peng, Shenzhen (CN); Baode Ma, Shenzhen (CN); Yongpeng Zheng, Shenzhen (CN); Shaotao Bai, Shenzhen (CN)

(73) Assignee: Guangdong OXO Chem Ltd., Huizhou (CN)

( * ) Notice: Subject to any disclaimer, the term of this patent is extended or adjusted under 35 U.S.C. 154(b) by 387 days.

(21) Appl. No.: 17/725,853

(22) Filed: Apr. 21, 2022

(65) Prior Publication Data

US 2022/0242891 A1    Aug. 4, 2022

(30) Foreign Application Priority Data

| Apr. 26, 2021 | (CN) | 202110452082.3 |
| Apr. 26, 2021 | (CN) | 202110464585.2 |
| May 8, 2021 | (CN) | 202110501267.9 |
| May 24, 2021 | (CN) | 202110565725.5 |

(51) Int. Cl.

| C07F 9/145 | (2006.01) |
| B01J 31/02 | (2006.01) |
| C07C 37/00 | (2006.01) |
| C07C 41/18 | (2006.01) |
| C07C 45/00 | (2006.01) |
| C07C 45/28 | (2006.01) |
| C07C 45/49 | (2006.01) |
| C07C 45/62 | (2006.01) |
| C07C 45/68 | (2006.01) |
| C07C 45/72 | (2006.01) |
| C07F 9/6561 | (2006.01) |

(52) U.S. Cl.
CPC ........... C07F 9/145 (2013.01); B01J 31/0258 (2013.01); C07C 37/001 (2013.01); C07C 41/18 (2013.01); C07C 45/00 (2013.01); C07C 45/28 (2013.01); C07C 45/62 (2013.01); C07C 45/68 (2013.01); C07C 45/72 (2013.01); C07F 9/6561 (2013.01)

(58) Field of Classification Search
CPC ........ C07F 9/145; C07F 9/6561; C07C 45/49; C07C 37/001; C07C 41/18; B01J 31/0258
See application file for complete search history.

(56) References Cited

U.S. PATENT DOCUMENTS

| 4,148,830 A | 4/1979 | Pruett et al. |
| 4,668,651 A | 5/1987 | Billig et al. |
| 4,769,498 A | 9/1988 | Billig et al. |
| 2013/0135574 A1 | 5/2013 | Wang |

FOREIGN PATENT DOCUMENTS

| CN | 86106770 A | 5/1987 |
| CN | 1041761 A | 5/1990 |
| CN | 105503542 A | 4/2016 |
| CN | 109761774 A | 5/2019 |

*Primary Examiner* — Sikarl A Witherspoon

(57) ABSTRACT

Disclosed are a spiro-bisphosphorous compound, and a preparation and application thereof. The spiro-bisphosphorous compound is expressed in formula (I), (II) or (III).

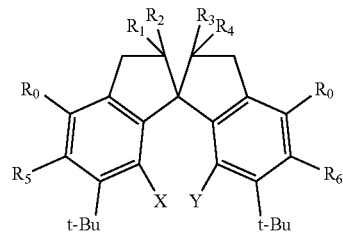

(I)

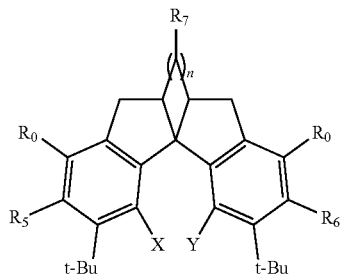

(II)

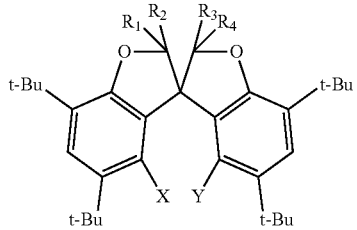

(III)

X = OH, OPR$_9$, PR$_9$, CH$_2$PR$_9$, NR$_9$
Y = OH, OPR$_9$, PR$_9$, CH$_2$PR$_9$, NR$_9$

20 Claims, 5 Drawing Sheets

SPIRO-BISPHOSPHOROUS COMPOUND, AND PREPARATION AND APPLICATION THEREOF

CROSS-REFERENCE TO RELATED APPLICATIONS

This application claims the benefit of priority from Chinese Patent Applications No. 202110464585.2, filed on Apr. 26, 2021; No. 202110452082.3, filed on Apr. 26, 2021; No. 202110501267.9, filed on May 8, 2021; and No. 202110565725.5, filed on May 24, 2021. The content of the aforementioned applications, including any intervening amendments thereto, is incorporated herein by reference in their entireties.

TECHNICAL FIELD

This application relates to chemical synthesis, and more particularly to a spiro-bisphosphorous compound, and a preparation and application thereof.

BACKGROUND

Axisymmetric organic compounds have attracted considerable attention in the asymmetric catalysis field, and have been widely used in the biomedical, industrial catalysis and functional materials. Among them, biaryl ligands, such as binaphthol (BINOL) and binaphthyl (BINAP) shown below, have been widely used in the industrial synthesis.

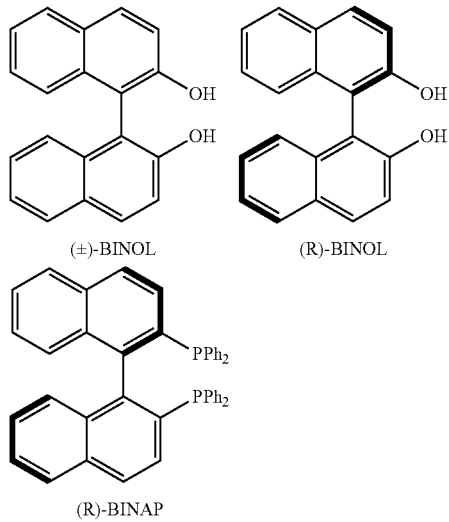

In 1999, Birman et al. prepared racemic 1,1'-spirobiindane-7,7'-diol ((±)-SPINOL) from acetone and 3-methoxybenzaldehyde by six steps. The diastereoisomers formed by the 1,1'-spirobiindane-7,7'-diol with L-menthyl chloroformate can be separated by column chromatography to obtain optically-pure (R)-(+)-SPINOL and (S)-(−)-SPINOL. Similar synthetic routes and resolution strategies have also been published in US20130135574A1 and CN1055003542A. Based on this, a more practical resolution approach was reported by Zhou et al. in 2002. In view of the fact that N-benzylcinchonidium chloride and one of the enantiomers are easy to form an inclusion complex, the optically-pure SPINOL can be obtained merely by steps of simple reflux, cooling, crystallization, filtration and acidification. In 2016, Tan et al. developed an asymmetric synthesis approach of SPINOL under the catalysis of a chiral phosphonic acid ligand, where the 1,5-bis-(5-hydroxy-2-methylphenyl)-3-pentanone underwent cyclodehydration to form (S)-4,4'-dimethyl-7,7'-dihydroxy-1,1'-spirobiindane (97% yield and 90% ee). It is worth noting that the phosphonic acid ligand is a phosphonic acid with a chiral SPINOL backbone. Additionally, CN109761774A proposed a method for manufacturing racemic SPINOL from 1,5-bis(3-hydroxyphenyl)-3-pentanone through Friedel-Crafts cyclization. This was the first report on the synthesis of SPINOL via cyclization without an occupying group at a para-position of the hydroxyl.

Discovered by Otto Roelen in 1938, hydroformylation is one of most prominent applications in the industrial homogeneous catalytic reaction. Propylene is hydroformylated to produce butyraldehyde, which undergoes consecutive aldol condensation and hydrogenation to afford butanol and octanol (mainly used in the production of dioctyl phthalate (DOP)). The DOP has the largest production and consumption with a global annual demand exceeds 6 million tons. However, due to its low molecular weight and volatility issue, the DOP does not meet the current environmental, health and safety standards. Plasticizer with larger molecular weight, lower volatility and greater stability is preferred. Consequently, butene is subjected to hydroformylation to produce valeraldehyde, follows by similar reactions to give 2-propylheptanol (2-PH). The diisodecyl phthalate (DPHP) plasticizer manufactured from 2-PH meets the requirements concerning environmental protection, health and safety issues. In some areas, such as the United States and the European Union regions, DOP has been replaced with DPHP, and this trend has already extended to the Asian market.

The hydroformylation of mixed C4 is recognized as the most economical and direct strategy in the current valeraldehyde production processes. A catalytic system of biphenyl bisphosphite ligand (Biphephos) and rhodium developed by the Union Carbide Company (now DOW Chemical) enables efficient hydroformylation of 2-butene in the mixed C4 with a high linear/branched (l/b) aldehydes ratio. U.S. Pat. Nos. 4,668,651A, 4,769,498A, 4,148,830A, CN86106770A and CN86106811A proposed that the bisphosphite ligand could increase the l/b ratio to 26. Currently, the Biphephos-catalyzed hydroformylation has been industrialized by Dow globally.

In the hydroformylation, bidentate and polydentate phosphite/phosphoramidite ligands with biphenyl, binaphthyl and anthracene skeletons (such as Biphephos and Anthracenetriol-based triphosphite) have been widely reported and patented by major companies such as BASF, Dow Chemical and Evonik, as well as several research groups, while spiro-bisphosphorous ligand was rarely reported. In 2012, Ding et al. proposed a series of spiroketal bisphosphoramidite ligands, which exhibited excellent conversions (up to 90%) and l/b ratios (up to 174.4) in the hydroformylation of 1-hexene and other terminal alkenes. Nevertheless, for internal olefins, the conversion was less than 15%. Therefore, developing novel SPINOL or O-SPINOL backbones and their bisphosphorous ligands with higher speed (reaction rate), selectivity, stability and easy separation ("4S" rule) for hydroformylation is important and valuable for industrial application.

SUMMARY

An object of the present disclosure is to provide a spiro-bisphosphorous compound to overcome the above-mentioned problems.

Technical solutions of the disclosure are described as follows.

In a first aspect, this application provides a spiro-bisphosphorous compound of formula (I), formula (II) or formula (III):

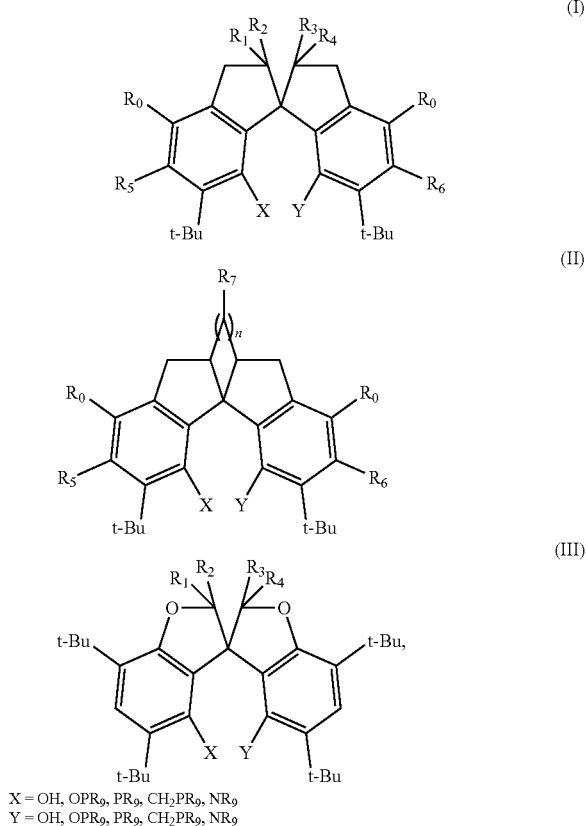

X = OH, OPR$_9$, PR$_9$, CH$_2$PR$_9$, NR$_9$
Y = OH, OPR$_9$, PR$_9$, CH$_2$PR$_9$, NR$_9$ $R_0$ is methoxy or tert-butyl; $R_1$, $R_2$, $R_3$ and $R_4$ are independently selected from the group consisting of $C_1$-$C_{10}$ alkyl, alkoxy, aryl, aryloxy and hydrogen; and $R_5$, $R_6$ and $R_7$ are independently selected from the group consisting of $C_1$-$C_{10}$ alkyl, alkoxy, aryl, aryloxy and hydrogen; n is $C_1$-$C_{10}$ alkylene; and PR$_9$ is a chlorophosphite structure comprising an aryl group selected from the group consisting of a biphenyl, methylene diphenyl, binaphthyl, benzoyloxy, o-phenyl, phenyl, and naphthyl group; or a chlorophosphoramidite structure comprising pyrrolyl, imidazolyl, carbazolyl or pyridyl.

In a second aspect, this application provides a method for preparing the spiro-bisphosphorous compound, comprising:
subjecting 3-hydroxybenzaldehyde, 5-hydroxy-2-methoxybenzaldehyde, 3-methoxybenzaldehyde or 3-hydroxybenzaldehyde to alkylation, aldol condensation, hydrogenation and cyclodehydration in sequence to obtain 1,1'-spirobiindane-7,7'-diol; and subjecting the 1,1'-spirobiindane-7,7'-diol to esterification to obtain the spiro-bisphosphorous compound of formula (I) or (II);
subjecting 3-methoxyphenol to alkylation, nucleophilic substitution, oxidation, cyclodehydration and debromination in sequence to obtain 1,1'-spirobiindane-7,7'-diol; and subjecting the 1,1'-spirobiindane-7,7'-diol to esterification to obtain the spiro-bisphosphorous compound of formula (III); or subjecting 1,3-dihalobenzene to lithiation, nucleophilic addition, dehydration, aldol condensation/Cannizzaro reaction, aromatic nucleophilic substitution, Pd/C-catalyzed debenzylation and alkylation in sequence to obtain 1,1'-spirobiindane-7,7'-diol; and subjecting the 1,1'-spirobiindane-7,7'-diol to esterification to obtain the spiro-bisphosphorous compound of formula (III).

In a third aspect, this application provides a method for catalyzing hydroformylation, comprising:
sequentially adding the spiro-bisphosphorous compound and a transition metal catalyst to an organic solvent in a reaction vessel under the protection of an inert gas followed by stirring at room temperature for complexation, wherein a molar ratio of phosphine in the spiro-bisphosphorous compound to the transition metal catalyst is (1-5):1;
under the protection of an inert gas, adding liquified etherified C4, methanol-to-olefins (MTO) C4, cis-2-butene or trans-2-butene to the reaction vessel followed by stirring at room temperature, wherein a concentration of the transition metal catalyst is controlled at 50-200 ppm; and
feeding hydrogen and carbon monoxide into the reaction vessel followed by reaction under stirring at 40-100° C. for 1-4 h, wherein a pressure ratio of the hydrogen to the carbon monoxide is 1:(1-5), and a total pressure of hydrogen and carbon monoxide is controlled at 0.5-1 MPa.

Compared to the prior art, this application has the following beneficial effects.

This application has significantly simplified synthesis process in which the racemic spirobiphenol can be produced from the staring material by merely four steps, and is free of expensive reagents and metal catalysts, and thus suitable for the scale-up industrial synthesis. Moreover, the synthesis approach developed herein has simple operation, high yield, mild reaction conditions and recyclable materials. The spiro-bisphosphorous compound provided herein can be applied to economically catalyze the hydroformylation of etherified C4 or MTO C4.

DETAILED DESCRIPTION OF EMBODIMENTS

Figure 1:
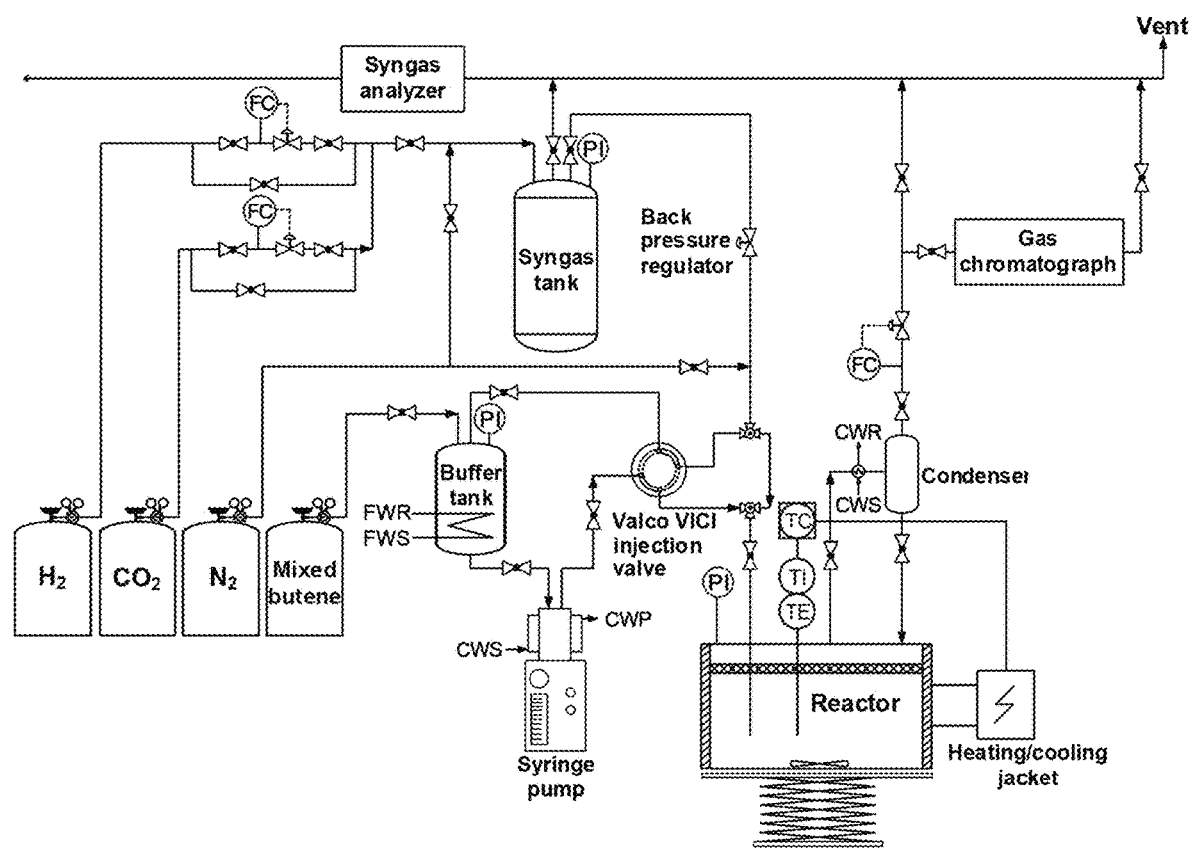
FIG. 1 schematically shows a batch/semi-batch oxo-synthesis unit in Comparative Example.

In order to make the objects, advantages and technical solutions of the present disclosure clearer, the present disclosure will be clearly and completely described below with reference to the embodiments. It should be understood that these embodiments are merely illustrative of the disclosure, and are not intended to limit the scope of the disclosure.

In a first aspect, this application provides a spiro-bisphosphorous compound of formula (I), formula (II) or formula (III):

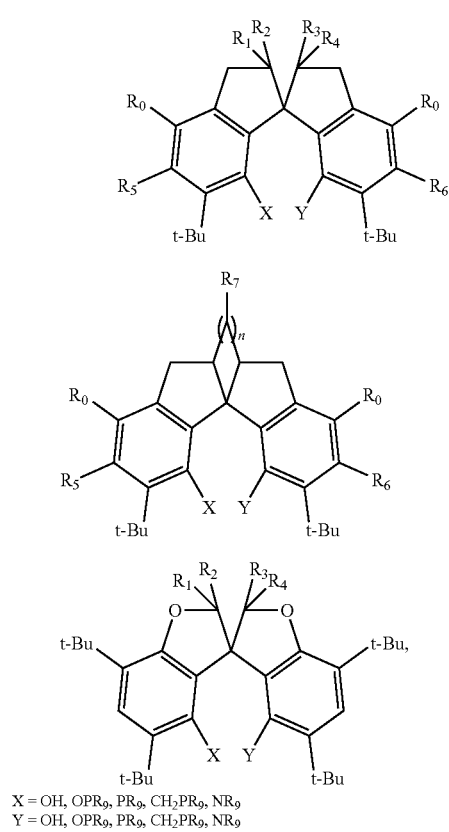

X = OH, OPR$_9$, PR$_9$, CH$_2$PR$_9$, NR$_9$
Y = OH, OPR$_9$, PR$_9$, CH$_2$PR$_9$, NR$_9$ where R$_0$ is methoxy or tert-butyl; R$_1$, R$_2$, R$_3$ and R$_4$ are independently selected from the group consisting of: C$_1$-C$_{10}$ alkyl, alkoxy, aryl, aryloxy and hydrogen; R$_5$, R$_6$ and R$_7$ are independently selected from the group consisting of C$_1$-C$_{10}$ alkyl, alkoxy, aryl, aryloxy and hydrogen; n is a C$_1$-C$_{10}$ alkylidene; and PR$_9$ is a chlorophosphite structure including an aryl group selected from the group consisting of a biphenyl, methylene diphenyl, binaphthyl, benzoyloxy, o-phenyl, phenyl, or naphthyl group; or a chlorophosphoramidite structure including pyrrolyl, imidazolyl, carbazolyl or pyridyl.

In an embodiment, the spiro-bisphosphorous compound is expressed by formula (I-1) or (II-1):

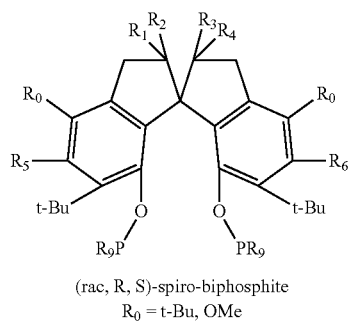

(rac, R, S)-spiro-biphosphite
R$_0$ = t-Bu, OMe

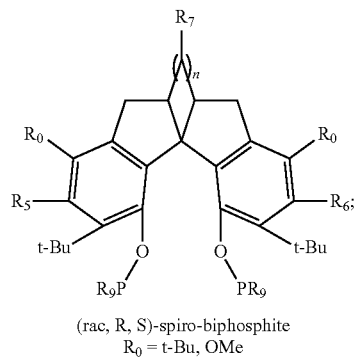

(rac, R, S)-spiro-biphosphite
R$_0$ = t-Bu, OMe where the PR$_9$ is selected from the group consisting of:

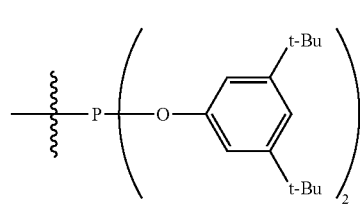

L1

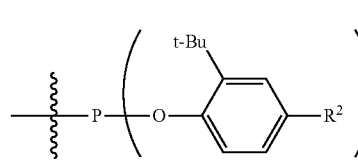

L2

R$^2$ = t-Bu, H, Me, OMe, CF$_3$, Cl

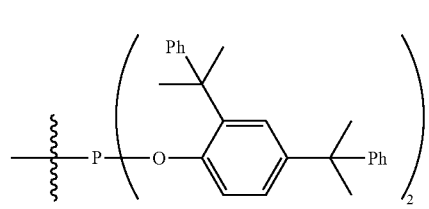

L3

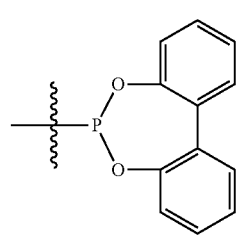

L4

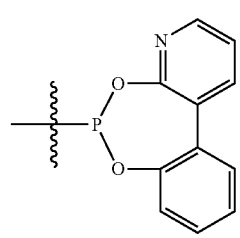

L5

-continued
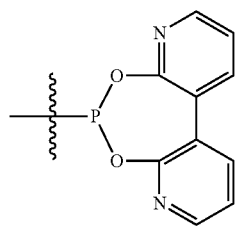
L6
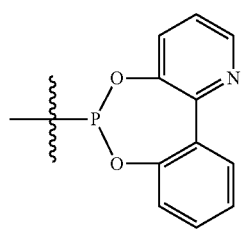
L7
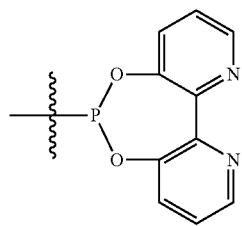
L8
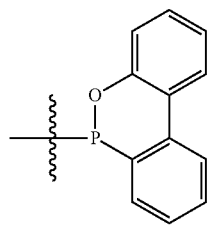
L9
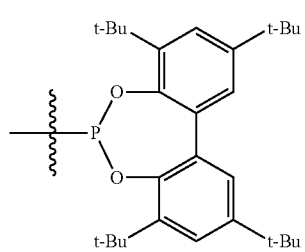
L10
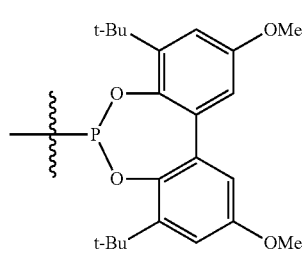
L11
-continued
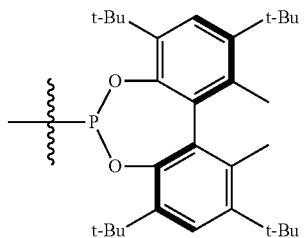
(R)-L12
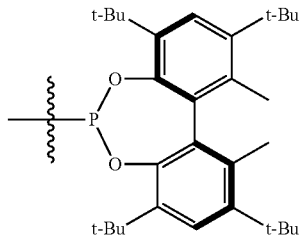
(S)-L12
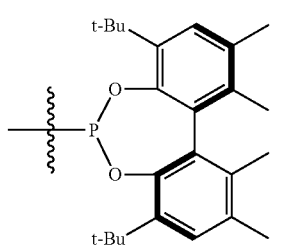
(R)-L13
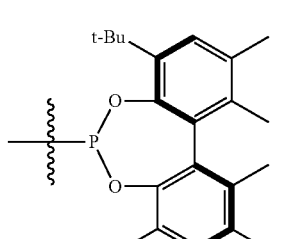
(S)-L13
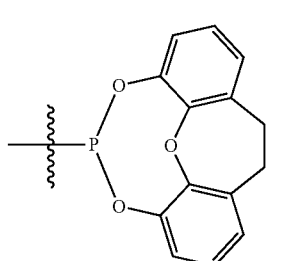
L14
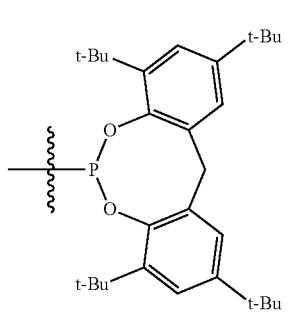
L15

-continued
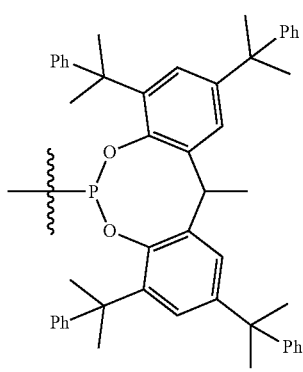
L16
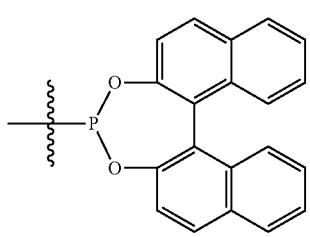
L17
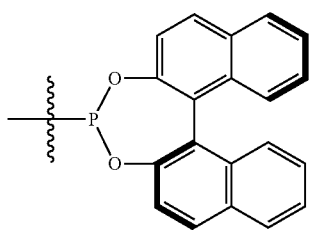
(R)-L17
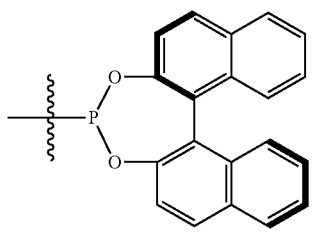
(S)-L17
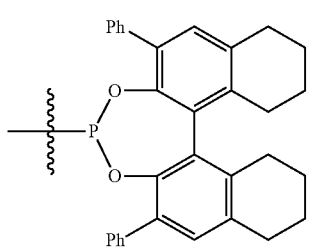
L18
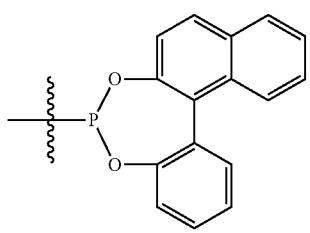
L19
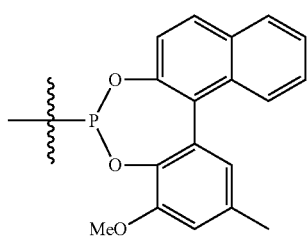
L20
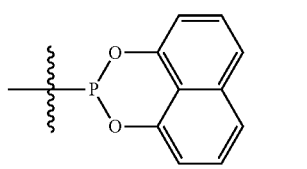
L21
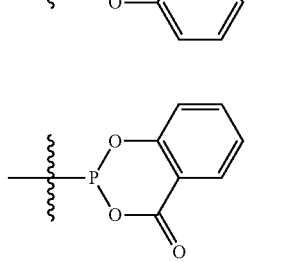
L22
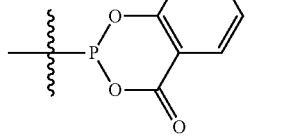
L23
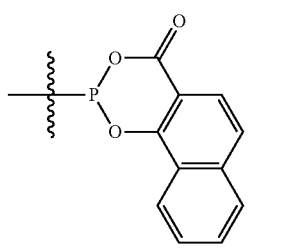
L24
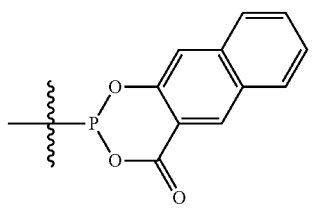
L25
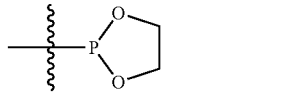
L26
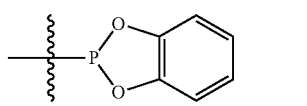
L27
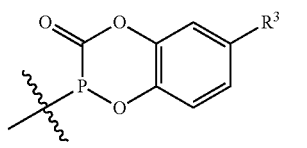
$R^3$ = H, $NO_3$, Cl -continued
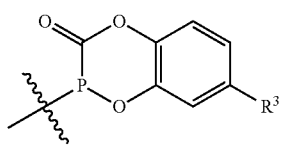
L28
R³ = OMe, Cl
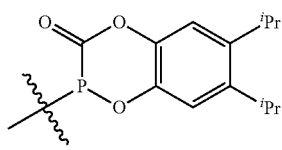
L29
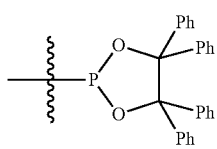
L30
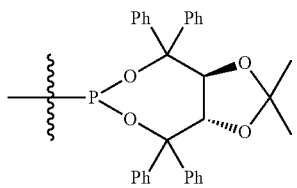
L31
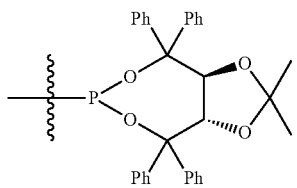
(R)-L31
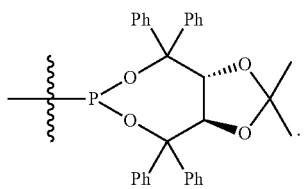
(S)-L31
In an embodiment, the spiro-bisphosphorous compound is expressed by formula (III-1):
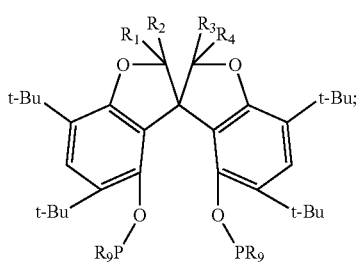
(III-1)
(rac, R, S)-O-spiro-biphosphite/biphosphoramidite
(t-Bu sub)
where the PR$_9$ is selected from the group consisting of:
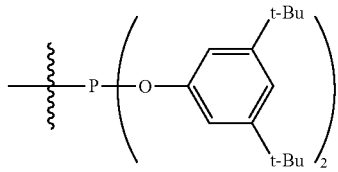
L1
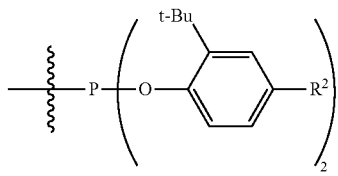
L2
R² = t-Bu, H, Me, OMe, CF₃, Cl
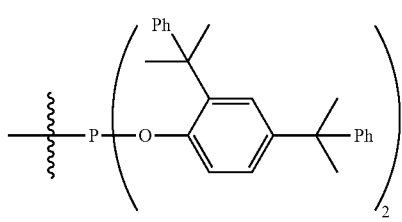
L3
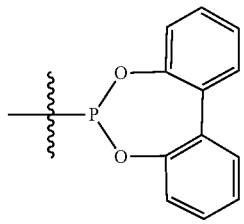
L4
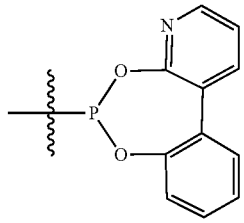
L5
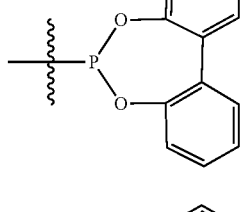
L6
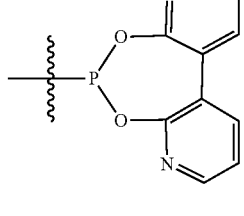
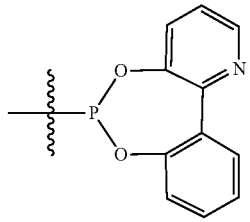
L7

L8
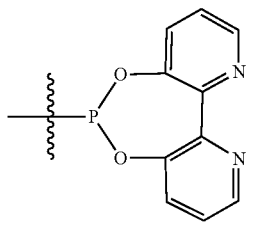
L9
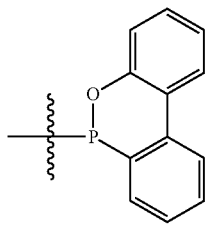
L10
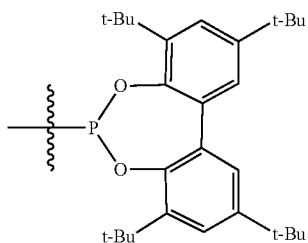
L11
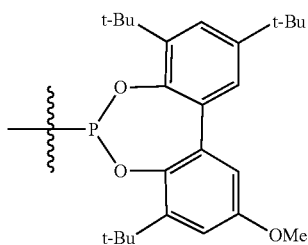
(R)-L12
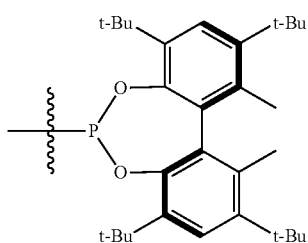
(S)-L12
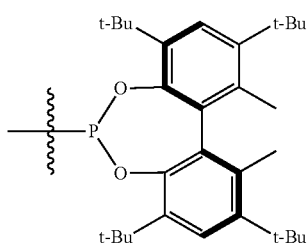
(R)-L13
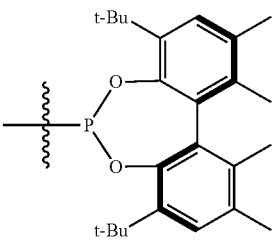
(S)-L13
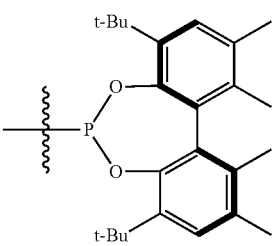
L14
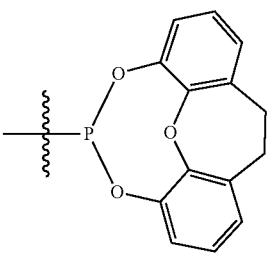
L15
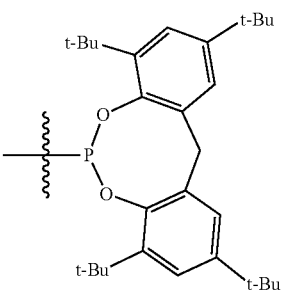
L16
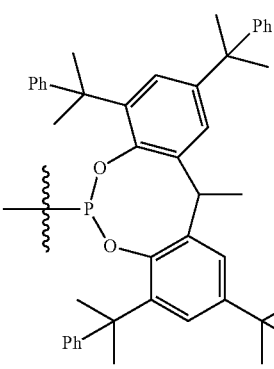
L17
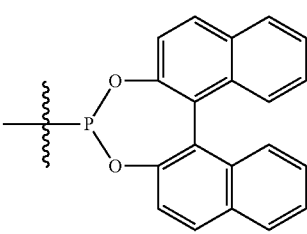

-continued
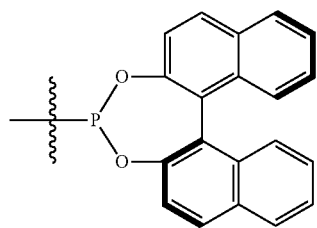
(R)-L17
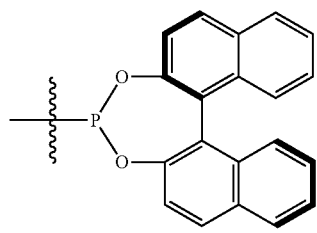
(S)-L17
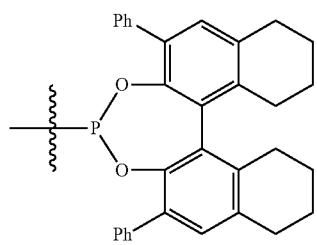
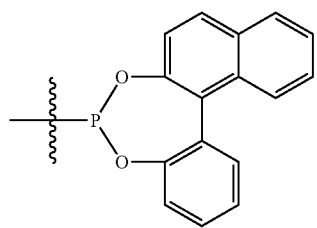
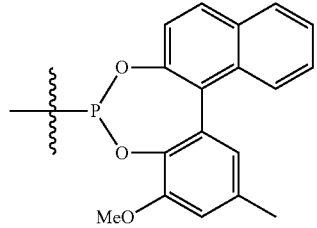
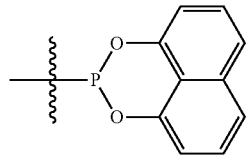
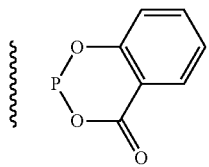
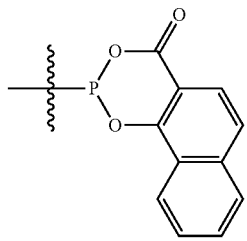
L23
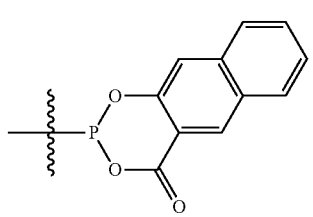
L24
L18
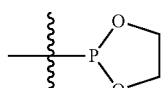
L25
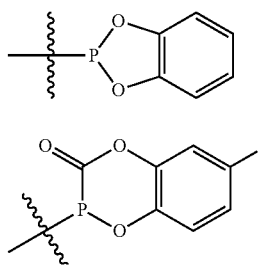
L26
L19
R³ = H, NO₂, Cl
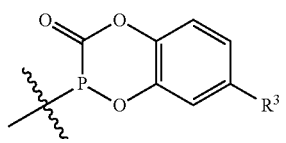
L27
L20
R³ = OMe, Cl
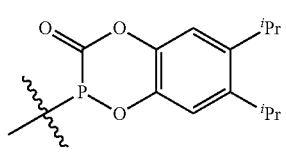
L28
L21
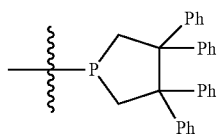
L29
L22
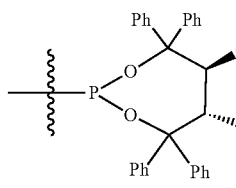
L30
L31

-continued
(R)-L31
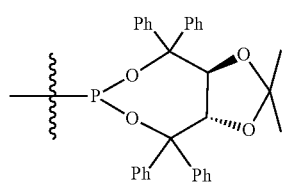
(S)-L31
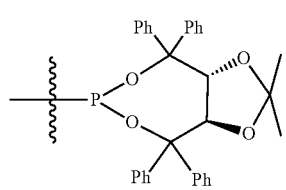
L32
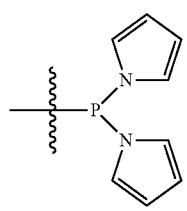
L33
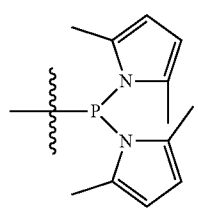
L34
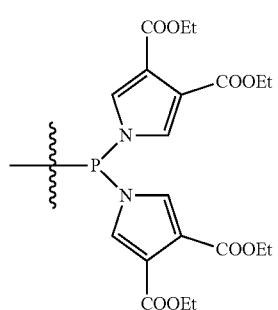
L35
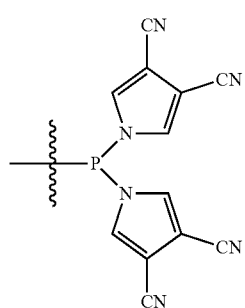
-continued
L36
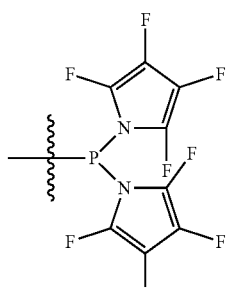
L37
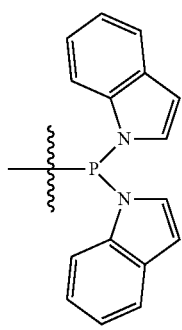
L38
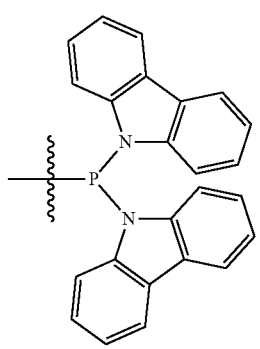
L39
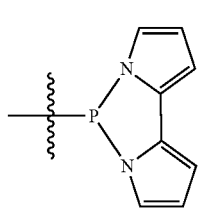
L40
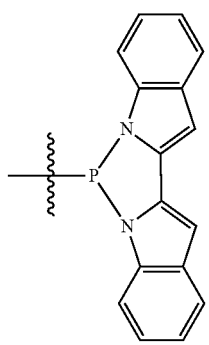

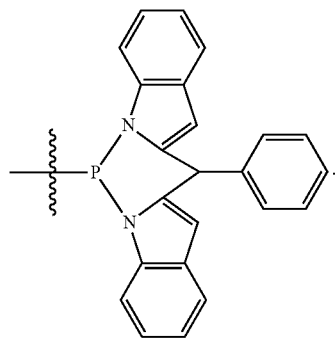

L41

This application also provides a method for preparing the above-mentioned spiro-bisphosphorous compound, including:

subjecting 3-hydroxybenzaldehyde, 5-hydroxy-2-methoxybenzaldehyde, 3-methoxybenzaldehyde or 3-hydroxybenzaldehyde to alkylation, aldol condensation, hydrogenation and cyclodehydration in sequence to obtain 1,1'-spirobiindane-7,7'-diol; and subjecting the 1,1'-spirobiindane-7,7'-diol to esterification to obtain the spiro-bisphosphorous compound of formula (I) or (II);

subjecting 3-methoxyphenol to alkylation, nucleophilic substitution, oxidation, cyclodehydration and debromination in sequence to obtain 1,1'-spirobiindane-7,7'-diol; and subjecting the 1,1'-spirobiindane-7,7'-diol to esterification to obtain the spiro-bisphosphorous compound of formula (III); or subjecting 1,3-dihalobenzene to lithiation, nucleophilic addition, dehydration, aldol condensation/Cannizzaro reaction, aromatic nucleophilic substitution, Pd/C-catalyzed debenzylation and alkylation in sequence to obtain 1,1'-spirobiindane-7,7'-diol; and subjecting the 1,1'-spirobiindane-7,7'-diol to esterification to obtain the spiro-bisphosphorous compound of formula (III).

In an embodiment, a synthesis route of 4, 4', 6, 6'-tetra-tert-butyl-1, 1'-spirobiindane-7, 7'-diol and a bisphosphorous ligand thereof (synthesis route 1) is illustrated as follows:

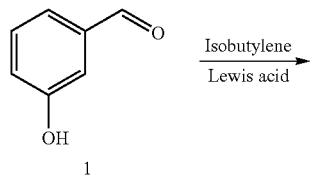

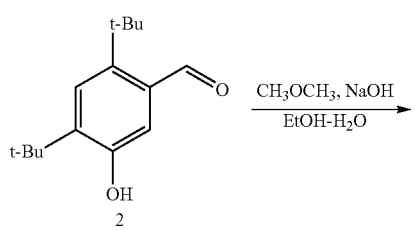

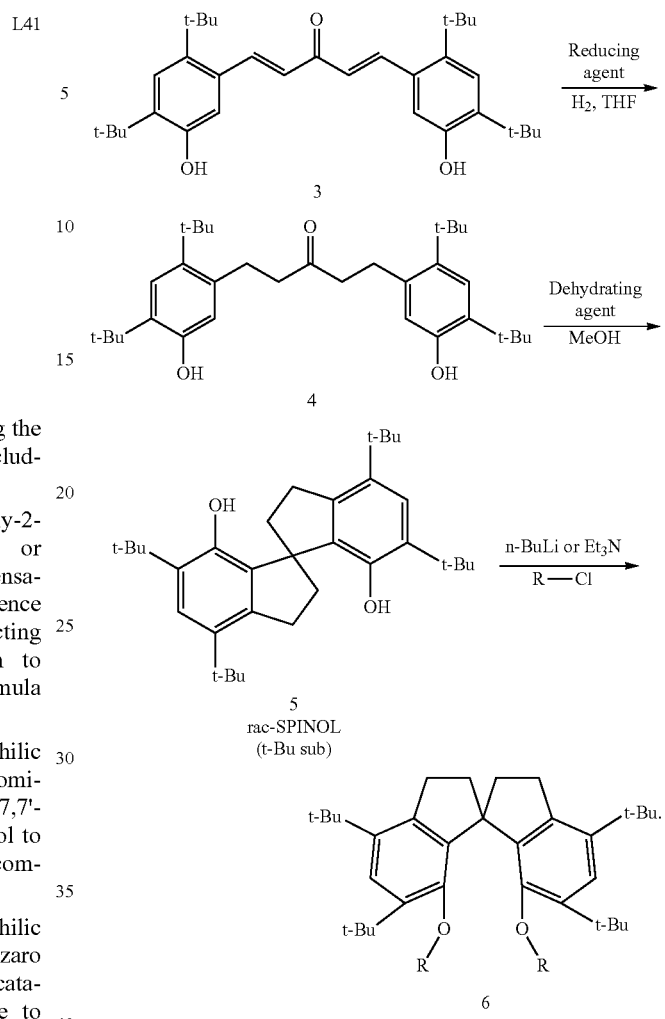

A synthesis route of 4, 4'-dimethoxy-6, 6'-di-tert-butyl-1, 1'-spirobiindane-7, 7'-diol and a bisphosphorous ligand thereof (synthesis route 2) is illustrated as follows:

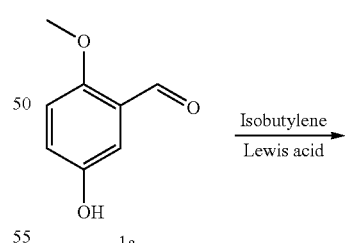

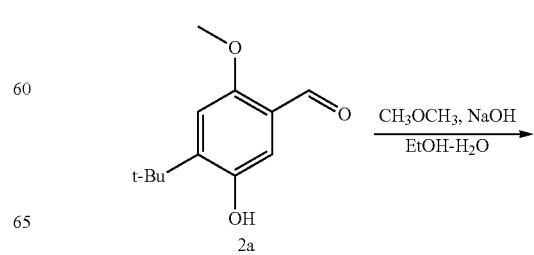

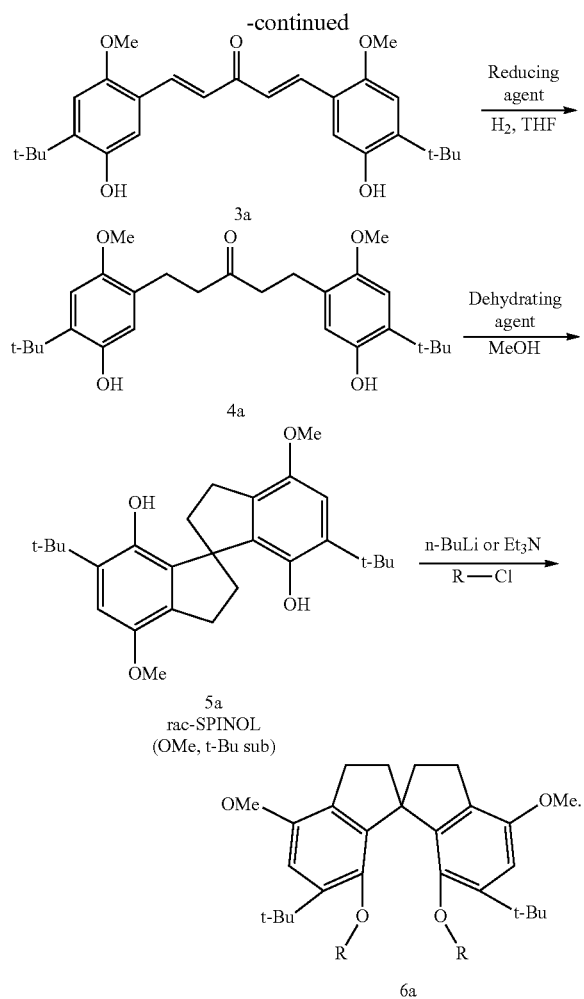

The compound 6 and compound 6a pertain to a class of spiro-bisphosphorous compounds of formula (I). These spiro-bisphosphorous compounds of formula (I) can be racemates containing a symmetrical structure or an asymmetrical structure, and also can be optically active or chiral. R denotes a class of chlorophosphite structures including a biphenyl group, a methylene diphenyl group, a binaphthyl group, a benzoyloxy, a o-phenyl group, a phenyl group, a naphthyl group or an aryl group.

The synthesis route 1 and the synthesis route 2 will be further described below. Serial numbers involved are limited to corresponding compounds in the synthesis routes 1-2. For example, intermediate 2 is 2,4-di-tert-butyl-5-hydroxybenzaldehyde (2).

Isobutylene is subjected to addition reaction with proton under the catalysis of a protonic acid or a Lewis acid to produce a tert-butyl carbocation, which is then subjected to alkylation with 3-hydroxybenzaldehyde or 5-hydroxy-2-methoxybenzaldehyde to obtain the compound 2 or compound 2a.

The protonic acid or Lewis acid is an organic acid, an inorganic acid or a combination thereof, where the organic acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluenesulfonic acid and a combination thereof, and the inorganic acid is selected from the group consisting of hydrobromic acid, hydrochloric acid, hydrofluoric acid, sulfurous acid, sulfuric acid, perchloric acid, phosphonic acid, pyrophosphoric acid, nitric acid, nitrous acid, chromic acid, magic acid, fluoroantimonic acid and a combination thereof. An alkylating agent is tert-butyl bromide, tert-butyl chloride, isobutene or tert-butanol. The alkylation is performed at 80-140° C. in a solvent selected from the group consisting of benzene, toluene, p-toluene, p-xylene, o-xylene, chlorobenzene and dichlorobenzene.

The compound 2 or 2a is subjected to aldol condensation with acetone to obtain 1, 5-bis(2, 4-di-tert-butyl-5-hydroxyphenyl)-1, 4-pentadien-3-one (3) or 1, 5-bis(2-methoxy-4-tert-butyl-5-hydroxyphenyl)-1, 4-pentadien-3-one (3a).

The above-mentioned aldol condensation is performed at 20-75° C. in a solvent in the presence of 1.5-10 equivalents of an alkali selected from the group consisting of potassium hydroxide, sodium hydroxide, potassium carbonate, sodium carbonate, sodium tert-butoxide and potassium tert-butoxide, where the solvent is ethanol, water or a mixture thereof in a volume ratio of (1-9):1.

The compound 3 or compound 3a is subjected to hydrogenation of carbon-carbon double bonds in the presence of a catalyst to obtain a compound 4 or 4a.

The catalyst is selected from the group consisting of Raney nickel, ferric chloride, cobalt oxide and Pd/C, and used in a ratio of 1-20% (w/w). The hydrogenation is performed at 20-50° C. and a hydrogen pressure of 0.05-5 MPa in a solvent for 24-72 h, where the solvent is selected from ethyl acetate, tetrahydrofuran, dichloromethane and 1,4-dioxane.

The compound 4 or 4a is subjected to cyclization in the presence of a dehydrating agent to obtain 4, 4', 6, 6'-tetra-tert-butyl-1, 1'-spirobiindane-7, 7'-diol (5) or 4, 4'-dimethoxy-6, 6'-di-tert-butyl-1, 1'-spirobiindane-7, 7'-diol (5a).

The dehydrating agent is selected from polyphosphoric acid, concentrated sulfuric acid, acetic anhydride, methanesulfonic acid, benzoic acid, p-toluenesulfonic acid and anhydrous aluminum trichloride, and 10-70 equivalents of the dehydrating agent are consumed. The cyclization is performed at 45-135° C. in a reaction solvent for 2-6 h, where the reaction solvent is selected from toluene, n-heptane, dichloromethane, trichloromethane and dichloroethane.

The compound 5 or compound 5a and an organic solvent are sequentially added to a reaction vessel under a nitrogen atmosphere to obtain a mixed solution; or the compound 5 or compound 5a and an organic solvent are successively added into a reaction vessel under a nitrogen atmosphere, to which n-butyllithium is added dropwise at a −78~−10° C., and the reaction mixture is restored to room temperature to obtain a lithiation product.

The mixed solution is dropwise added with a mixture of a chlorophosphite compound and an acid-binding agent, and subjected to esterification at room temperature under reflux conditions removal of inorganic salts and concentration to obtain a crude product of the compound 6 or 6a; or the lithiation product is dropwise added with an organic solution of the chlorinated form of the above-listed phosphite (L1-L31), and subjected to esterification under reflux conditions, removal of inorganic salts and concentration to obtain a crude product of the compound 6 or 6a, where the chlorophosphite compound includes an aryl group selected from the group consisting of a biphenyl group, a methylene diphenyl group, a binaphthyl group, a benzoyloxy group, an o-phenyl group, a phenyl group and a naphthyl group.

The esterification between the chlorophosphite compound and the compound 5 or 5a is performed in the presence of 5-20 equivalents of the acid-binding agent for 12-48 h, where the acid-binding agent is selected from triethylamine, N,N-diisopropylethylamine and pyridine. The esterification between the lithiation product and the chlorinated form of the phosphite is performed at −78-80° C. in the presence of 2-4 equivalents of n-butyllithium for 12-48 h. The organic solvent is selected from toluene, tetrahydrofuran, diethyl ether, 2-methyltetrahydrofuran, methyl tert-butyl ether, isopropyl ether, anisole, ethylene glycol dimethyl ether, diethylene glycol dimethyl ether, butyl ether, cyclopentyl methyl ether and 1,4-dioxane.

The crude product of the compound 6 or compound 6a is purified by crystallization with a solvent, which is selected from the group consisting of ethyl acetate, toluene, dichloromethane, ethanol, acetonitrile, petroleum ether, n-hexane, tetrahydrofuran and a combination thereof.

In an embodiment, a synthesis route 3 is illustrated as follows:

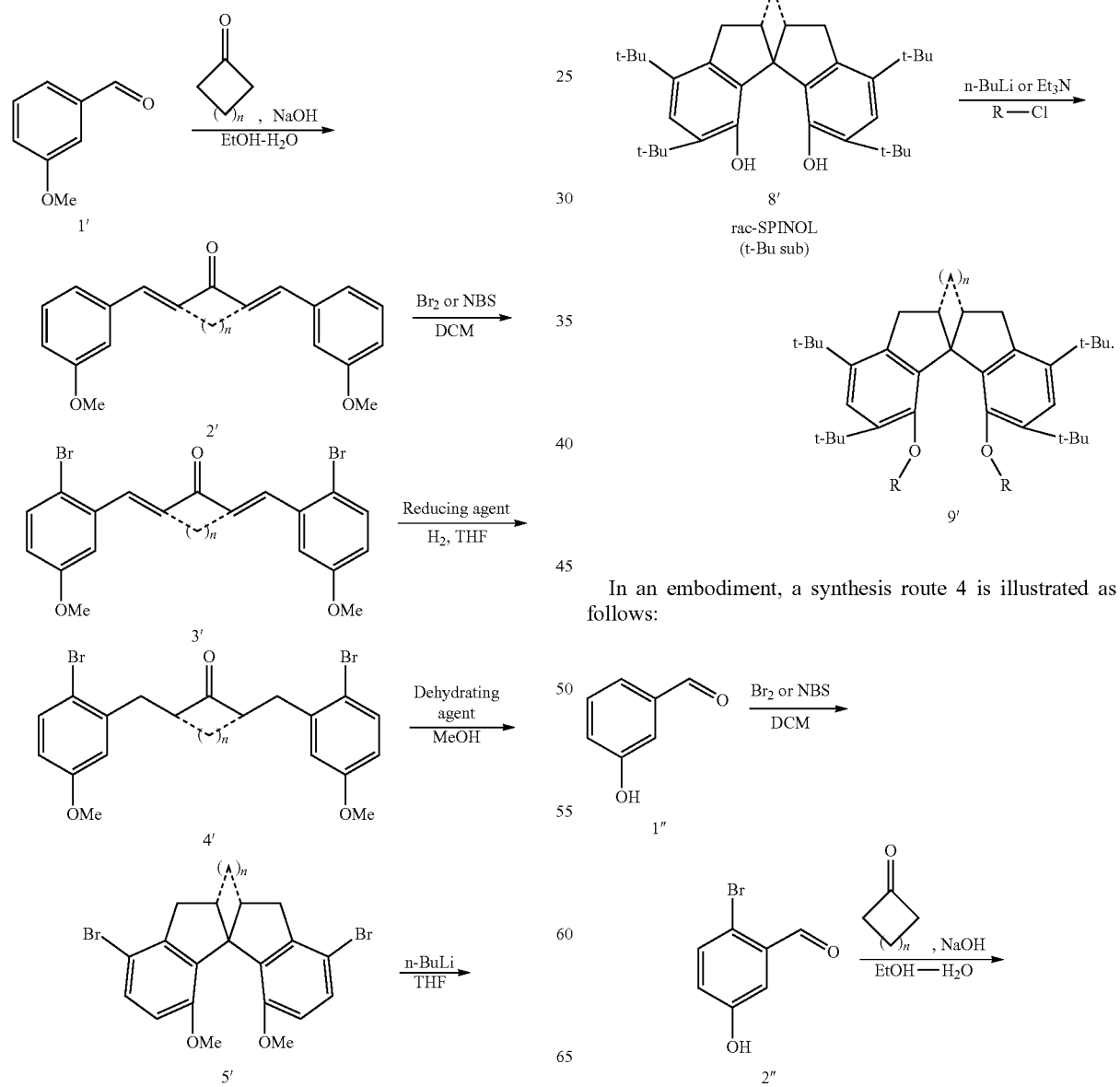

In an embodiment, a synthesis route 4 is illustrated as follows:

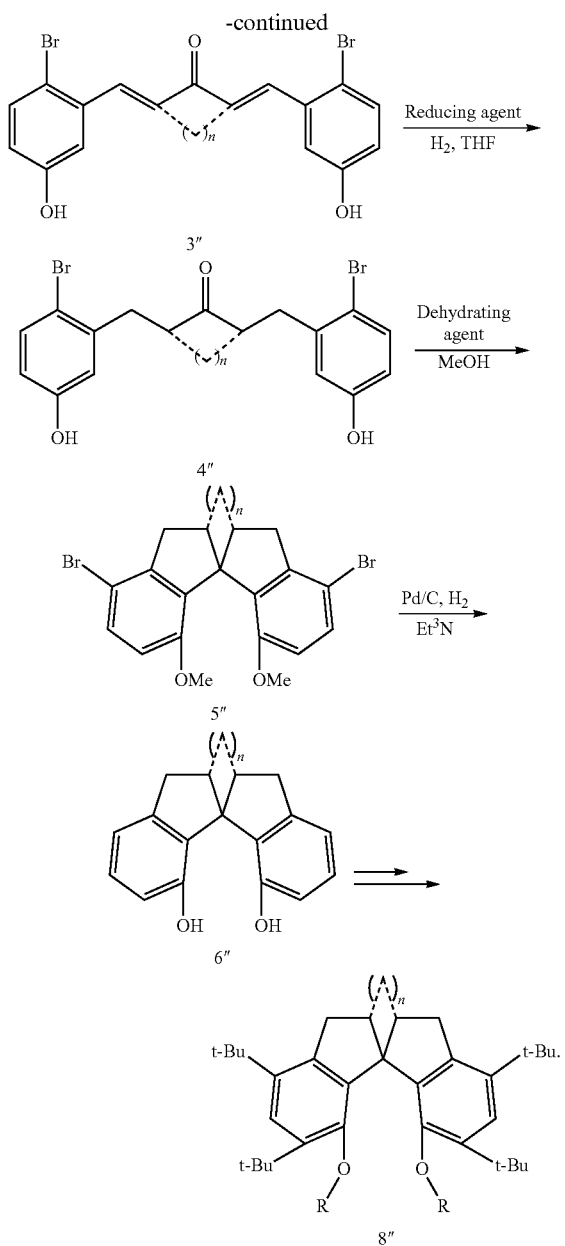

The compound 9' and a compound 8" pertain to a class of spiro-bisphosphorous compounds of formula (II) with large steric hindrance, which can be racemates including a symmetrical or asymmetrical structure, and also can be optically active or chiral. R—Cl denotes a class of chlorophosphite structures including a biphenyl group, a methylene diphenyl group, a binaphthyl group, a benzoyloxy group, an o-phenyl group, a phenyl group, a naphthyl group or an aryl group.

The synthesis route 3 and synthesis route 4 will be further described below. Serial numbers involved are merely limited to corresponding compounds in the synthesis routes 3 and 4.

3-methoxybenzaldehyde is subjected to aldol condensation with acetone (n=0) to obtain a compound 2', which is subjected to halogenation with bromine or N-bromosuccinimide to obtain a compound 3'. Or 3-hydroxybenzaldehyde is subjected to bromination and aldol condensation to obtain a compound 3".

The halogenation is performed at −20-40° C. in a solvent in the presence of 1-10 equivalents of the bromine or N-bromosuccinimide and 2-20 equivalents of pyridine for 2-24 h, where the solvent is an organic solvent such as diethyl ether, tetrahydrofuran, 1,4-dioxane and dichloromethane.

The aldol condensation is performed at 20-75° C. in a solvent in the presence of 1.5-10 equivalents of an alkali, where the alkali is selected from potassium hydroxide, sodium hydroxide, potassium carbonate, sodium carbonate, sodium tert-butoxide and potassium tert-butoxide, and the solvent is ethanol, water or a mixture thereof in a volume ratio of (1-9):1.

The compound 3' or compound 3" is subjected to hydrogenation of carbon-carbon double bonds in the presence of a catalyst to obtain 1, 5-bis(2-bromo-3-methoxyphenyl)-3-pentanone (4') or 1, 5-bis(2-bromo-3-hydroxyphenyl)-3-pentanone (4").

The hydrogenation is performed at 20-50° C. and a hydrogen pressure of 0.05-5 MPa in a solvent in the presence of 1-20% (w/w) of the catalyst for 24-72 h, where the solvent is selected from ethyl acetate, tetrahydrofuran, dichloromethane and 1,4-dioxane.

The compound 4' or compound 4" is subjected to cyclization in the presence of a dehydrating agent to obtain compound 5' or compound 5".

The cyclization is performed at 30-65° C. in a solvent in the presence of 5-50 equivalents of the dehydrating agent for 1-4 h, where the dehydrating agent is selected from polyphosphoric acid, concentrated sulfuric acid, acetic anhydride, methanesulfonic acid, benzoic acid, p-toluenesulfonic acid and anhydrous aluminum trichloride; and the solvent is selected from toluene, n-heptane, dichloromethane, trichloromethane and dichloroethane.

The compound 5' or compound 5" is subjected to debromination in the presence of Pd/C-based metal catalyst or n-butyllithium to obtain 7, 7'-dimethoxy-1, 1'-spirobiindane (6') or 1, 1'-spirobiindane-7, 7'-diol (6").

The debromination is performed at 25-40° C. and a hydrogen pressure of 0.1-5 MPa in a solvent in the presence of 5-10% (w/w) of the Pd/C-based metal catalyst for 5-12 h, or is performed at −78-5° C. in a solvent in the presence of 2.5-10 equivalents of n-butyllithium for 0.5-5 h, where the Pd/C-based metal catalyst contains at least 5% of Pd/C, and the solvent is an organic solvent such as diethyl ether, tetrahydrofuran, 1, 4-dioxane and methyl tert-butyl ether.

The compound 6' is subjected to demethylation in the presence of a demethylation agent to obtain 1, 1'-spirobiindane-7, 7'-diol (7', rac-SPINOL).

The demethylation is performed at −78-25° C. in a solvent in the presence of 2.0-5 equivalents of the demethylation agent, where the demethylation agent is selected from boron tribromide, hydrobromic acid, aluminum trichloride, pyridine hydrochloride and sodium ethanethiolate, and the solvent is dichloromethane, dichloroethane or trichloroethane.

Tert-butanol is dehydrated under the catalysis of a protonic acid or a Lewis acid to produce isobutylene, which is subjected to addition with a proton to obtain a tert-butyl carbocation. The tert-butyl carbocation is subjected to alkylation with compound 7' or compound 6" to obtain 4, 4', 6, 6'-tetra-tert-butyl-1, 1'-spirobiindane-7, 7'-diol (9' or 8").

The protonic acid or Lewis acid is an organic acid, an inorganic acid or a combination thereof. The organic acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluenesulfonic acid and a combination thereof. The inorganic acid is selected from the group consisting of hydrobromic acid, hydrochloric acid, hydrofluoric acid, sulfurous acid, sulfuric acid, perchloric acid, phosphonic acid, pyrophosphoric acid, nitric acid, nitrous acid, chromic acid, magic acid, fluoroantimonic acid and a combination thereof. An alkylating agent is selected from tert-butyl bromide, tert-butyl chloride, isobutene and tert-butanol. A reaction temperature is 50-110° C. A reaction solvent is selected from benzene, toluene, p-toluene, p-xylene, o-xylene, chlorobenzene and dichlorobenzene.

The compound 9' or the compound 8" and an organic solvent are successively added into a reaction vessel under a nitrogen atmosphere to obtain a mixed solution; or the compound 9' or compound 8" and an organic solvent are successively added into a reaction vessel under a nitrogen atmosphere, to which n-butyllithium is added dropwise at −78~−10° C., and the reaction mixture is restored to room temperature to obtain a lithiation product.

The mixed solution is dropwise added with a mixture of a chlorophosphite compound and an acid-binding agent, and subjected to esterification at room temperature under reflux conditions, removal of inorganic salts and concentration to obtain a crude product, or the lithiation product is dropwise added with an organic solution of the chlorinated form of the above-listed phosphite (L1-L31), and subjected to esterification under reflux conditions, removal of inorganic salts and concentration to obtain a crude product, where the chlorophosphite compound includes an aryl group selected from the group consisting of a biphenyl group, a methylene diphenyl group, a binaphthyl group, a benzoyloxy group, an o-phenyl group, a phenyl group and a naphthyl group.

The esterification between the spiro-bisphosphorous compound and the compound 9' or 8" is performed in the presence of 5-20 equivalents of the acid-binding agent for 12-48 h, where the acid-binding agent is selected from triethylamine, N,N-diisopropylethylamine and pyridine. The esterification between the lithiation product and the chlorinated form of the phosphite is performed at −78-80° C. in the presence of 2-4 equivalents of n-butyllithium for 12-48 h. The organic solvent is selected from toluene, tetrahydrofuran, diethyl ether, 2-methyltetrahydrofuran, methyl tert-butyl ether, isopropyl ether, anisole, ethylene glycol dimethyl ether, diethylene glycol dimethyl ether, butyl ether, cyclopentyl methyl ether and 1,4-dioxane.

The crude product is purified by crystallization with a solvent, which is selected from the group consisting of ethyl acetate, toluene, dichloromethane, ethanol, acetonitrile, petroleum ether, n-hexane, tetrahydrofuran and a combination thereof.

In an embodiment, three synthesis routes of the 4, 4', 6, 6'-tetra-tert-butyl-1, 1'-spirodihydrobenzofuran-7, 7'-diol and a bisphosphorous compound thereof are described as follows.

Synthesis Route 5

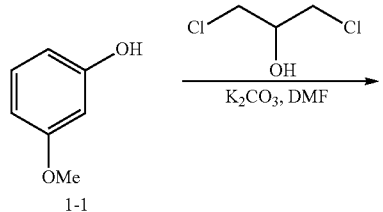

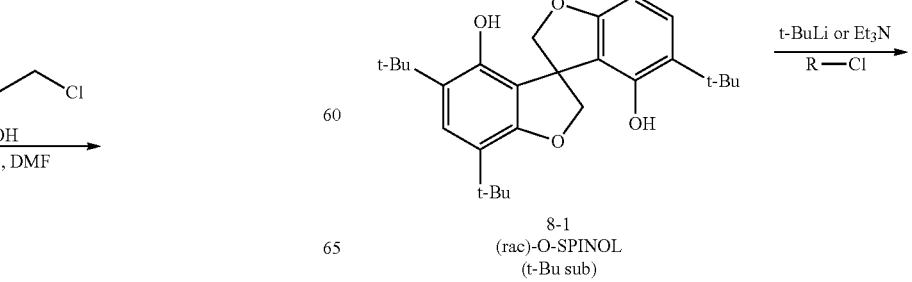

29
-continued
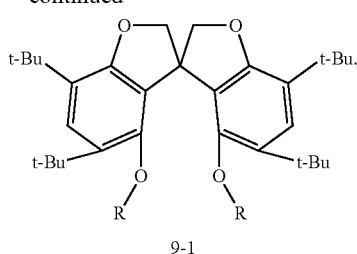
9-1
Synthesis Route 6
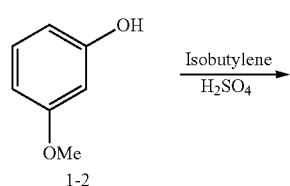
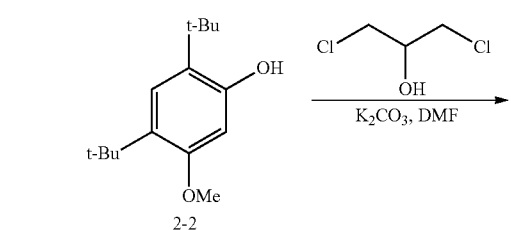
30
-continued
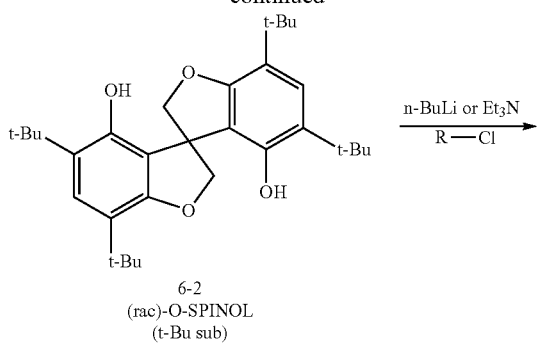
6-2
(rac)-O-SPINOL
(t-Bu sub)
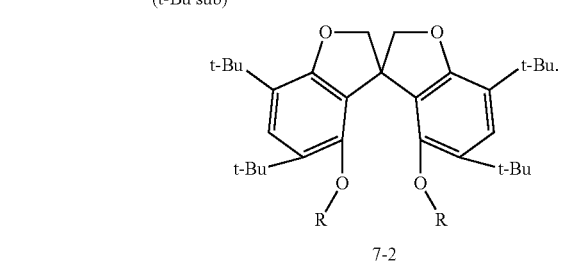
7-2
Synthesis Route 7
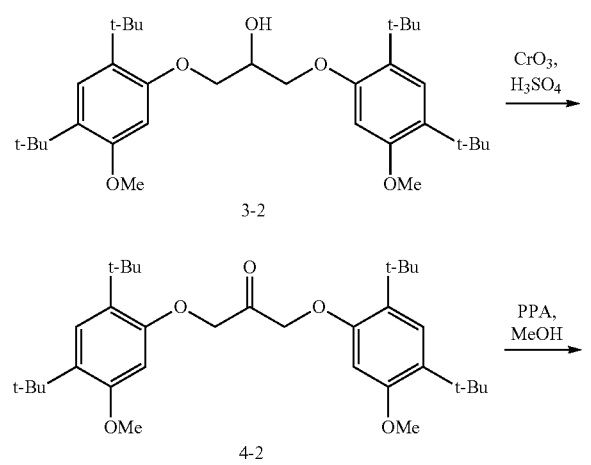
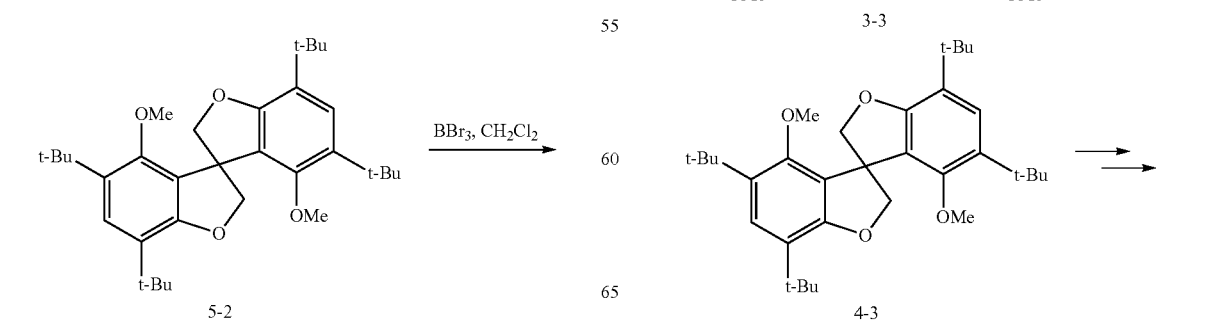

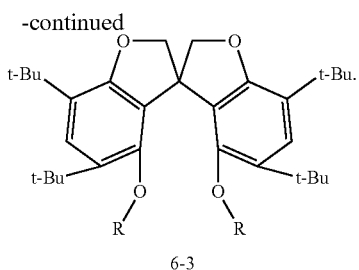

6-3

The compound 9-1, compound 7-2 and compound 6-3 pertain to a class of O-spiro-bisphosphorous ligands represented by formula (III), which can be racemates including a symmetrical or asymmetrical structure, and also can be optically active or chiral. R—Cl denotes a class of chlorophosphite structure including a biphenyl group, a methylene diphenyl group, a binaphthyl group, a benzoyloxy group, an o-phenyl group, a phenyl group, a naphthyl group or an aryl group; or a chlorophosphoramidite structure including pyrrolyl, imidazolyl, carbazolyl or pyridyl.

The synthesis route 5, synthesis route 6 and synthesis route 7 will be further described below. Serial numbers involved are merely limited to corresponding compounds in the synthesis routes 5-7.

3-methoxyphenol is subjected to nucleophilic substitution with 1,3-dichloro-2-propanol to obtain compound 2-1. Isobutylene is subjected to addition reaction with proton catalyzed by a protonic acid or Lewis acid to produce a tert-butyl carbocation, which is subjected to alkylation with 3-methoxyphenol to obtain compound 2-2 or 2-3. 2, 4-di-tert-butyl-5-methoxyphenol is further subjected to nucleophilic substitution with 1, 3-dichloro-2-propanol or 2, 2-bis(chloromethyl)-1, 3-dioxolane to obtain compound 3-2 or compound 3-3.

In addition to the 1, 3-dichloro-2-propanol and 2, 2-bis(chloromethyl)-1, 3-dioxolane, the halogenating reagent of the nucleophilic substitution can be also selected from 1, 3-difluoro-2-propanol, 1, 3-dibromo-2-propanol, 1, 3-diiodo-2-propanol and epichlorohydrin; or selected from 2, 2-bis(fluoromethyl)-1, 3-dioxolane, 2, 2-bis(bromomethyl)-1, 3-dioxolane and 2, 2-bis(iodomethyl)-1, 3-dioxolane.

The protonic acid or Lewis acid is an organic acid, an inorganic acid or a combination thereof. The organic acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulphonic acid, methanesulfonic acid, trifluoromethanesulfonic acid, p-toluenesulfonic acid and a combination thereof. The inorganic acid is selected from the group consisting of hydrobromic acid, hydrochloric acid, hydrofluoric acid, sulfurous acid, sulfuric acid, perchloric acid, phosphonic acid, pyrophosphoric acid, nitric acid, nitrous acid, chromic acid, magic acid, fluoroantimonic acid and a combination thereof. An alkylating agent is selected from the group consisting of tert-butyl bromide, tert-butyl chloride, isobutene and tert-butanol. A reaction temperature is 80-140° C. A reaction solvent is selected from benzene, toluene, p-toluene, p-xylene, o-xylene, chlorobenzene and dichlorobenzene.

The compound 2-1 or compound 3-2 is subjected to oxidation in the presence of chromium trioxide to obtain compound 3-1 or compound 4-2.

Apart from chromium trioxide, the oxidation can also be performed in the presence of 0.05-1 equivalents of chromic acid, potassium dichromate or sodium dichromate. The acid solution is concentrated sulfuric acid, phosphonic acid, hexafluorophosphonic acid, hypochlorous acid, chlorous acid, glacial acetic acid or peroxyacetic acid. A reaction solvent is acetone, water or a mixture thereof in a volume ratio of (50-70):(50-30). A reaction temperature is 25-45° C.

The compound 3-1 is subjected to halogenation with bromine or N-bromosuccinimide to obtain 1, 5-bis(2-bromo-3-methoxyphenoxy)-acetone (4-1). The compound 4-1, compound 4-2 or compound 3-2 is subjected to Friedel-Crafts reaction in the presence of a dehydrating agent to obtain compound 5-1, compound 5-2 or compound 4-3.

The halogenation is performed at −20-40° C. in a solvent in the presence of 1-10 equivalents of bromine or N-bromosuccinimide and 2-20 equivalents of pyridine for 2-24 h, where the solvent is an organic solvent such as diethyl ether, tetrahydrofuran, 1, 4-dioxane and dichloromethane.

The dehydrating agent is selected from polyphosphoric acid, concentrated sulfuric acid, acetic anhydride, methanesulfonic acid, benzoic acid, p-toluenesulfonic acid and anhydrous aluminum trichloride. The cyclization is performed at 45-135° C. in a solvent in the presence of 10-70 equivalents of the dehydrating agent for 2-6 h, where the solvent is selected from toluene, n-heptane, dichloromethane, trichloromethane and dichloroethane.

The compound 5-1 is subjected to debromination in the presence of n-butyllithium to obtain compound 6-1. The compound 6-1, compound 5-2 or compound 4-3 is subjected to demethylation in the presence of a demethylation reagent to obtain compound 7-1, compound 6-2 or compound 5-3. The compound 6-2 or the compound 5-3 is the target diphenol product (rac)-O-SPINOL. The compound 7-1 is subjected to alkylation with isobutene to obtain the target diphenol product.

The debromination is performed at −78-5° C. in a solvent in the presence of 2-4 equivalents of n-butyllithium for 0.5-5 h, where the solvent is an organic solvent such as diethyl ether, tetrahydrofuran, 1, 4-dioxane and methyl tert-butyl ether.

The demethylation is performed at −78-25° C. in a solvent in the presence of 2.0-5 equivalents of the demethylation reagent, where the demethylation reagent is selected from boron tribromide, hydrobromic acid, aluminum trichloride, pyridine hydrochloride and sodium ethanethiolate, and the solvent is dichloromethane, dichloroethane or trichloroethane.

The (rac)-O-SPINOL and an organic solvent are successively added into a reaction vessel under a nitrogen atmosphere to obtain a mixed solution; or the (rac)-O-SPINOL and an organic solvent are successively added into a reaction vessel under a nitrogen atmosphere, to which n-butyllithium is added dropwise at a −78~−10° C., and the reaction mixture is restored to room temperature to obtain a lithiation product.

The mixed solution is dropwise added with a mixture including a chlorophosphite or chlorophosphoramidite compound and an acid-binding agent, and subjected to esterification at room temperature under reflux conditions, removal of inorganic salts and concentration to obtain a crude product; or the lithiation product is added with an organic solution of the chlorinated form of the above-listed phosphite or phosphoramidite (L1-L40), and subjected to esterification under reflux conditions, removal of inorganic salts and concentration to obtain a crude product, where the chlorophosphite compound includes an aryl group selected from the group consisting of a biphenyl group, a methylene diphenyl group, a binaphthyl group, a benzoyloxy group, an o-phenyl group, a phenyl group and a naphthyl group; or a chlorophosphoramidite structure including pyrrolyl, imidazolyl, carbazolyl or pyridyl.

The esterification between the (rac)-O-SPINOL and the chlorophosphite or chlorophosphoramidite compound is performed in the presence of 5-20 equivalents of the acid-binding agent for 12-48 h, where the acid-binding agent is selected from triethylamine, N,N-diisopropylethylamine and pyridine. The esterification between the lithiation product and the chlorinated form of the above-listed phosphite or phosphoramidite is performed at −78-80° C. in the presence of 2-4 equivalents of n-butyllithium for 12-48 h. The organic solvent is selected from toluene, tetrahydrofuran, diethyl ether, 2-methyltetrahydrofuran, methyl tert-butyl ether, isopropyl ether, anisole, ethylene glycol dimethyl ether, diethylene glycol dimethyl ether, butyl ether, cyclopentyl methyl ether and 1, 4-dioxane.

The crude product is purified by crystallization with a solvent, which is selected from the group consisting of ethyl acetate, toluene, dichloromethane, ethanol, acetonitrile, petroleum ether, n-hexane, tetrahydrofuran and a combination thereof.

In an embodiment, the O-spiro-bisphosphorous is prepared via a synthesis route 8:

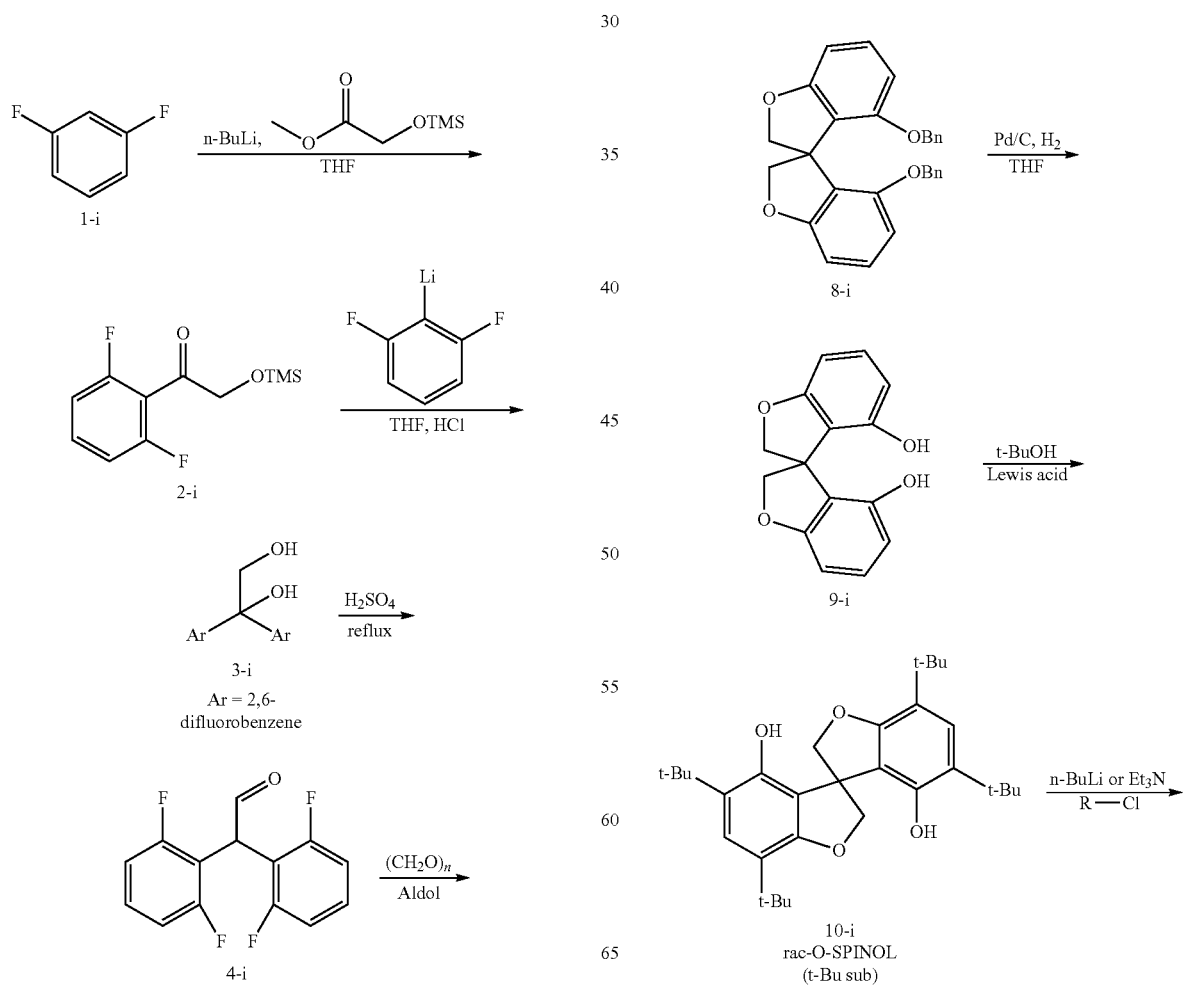

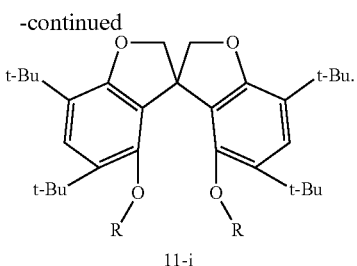

11-i

The compound 11-i pertain to a class of O-spiro-bisphosphorous ligands represented by formula (III), which can be racemates including a symmetrical or asymmetrical structure, and also can be optically active or chiral. R—Cl denotes a class of chlorophosphite structures including a biphenyl group, a methylene diphenyl group, a binaphthyl group, a benzoyloxy group, an o-phenyl group, a phenyl group, a naphthyl group or an aryl group; or a class of chlorophosphoramidite structures including a pyrrolyl, imidazolyl, carbazolyl or pyridyl.

The synthesis route 8 will be further described below. Serial numbers involved are merely limited to corresponding compounds in the synthesis route 8.

1, 3-difluorobenzene is subjected to lithiation with n-butyllithium to obtain an aryl lithium reagent, which is reacted with methyl trimethylsilyl (TMS) glycolate to obtain an aryl ketone. The aryl ketone is further subjected to nucleophilic addition with the aryl lithium reagent, and the addition product is hydrolyzed with dilute hydrochloric acid and subjected to TMS deprotection to obtain compound 3-i.

In this process, 1, 3-dichlorobenzene, 1, 3-dibromobenzene and 1, 3-diiodobenzene are also alternative starting materials. Considering that fluorine is the optimal leaving group in the subsequent SNAr reaction, 1, 3-difluorobenzene is preferred.

1-5 equivalents of the lithium reagent are required in the above reactions. The reaction is performed at −78-0° C. in a solvent for 1-12 h, where the solvent is an organic solvent such as diethyl ether, tetrahydrofuran, 1, 4-dioxane and dichloromethane.

In the nucleophilic addition, the organic lithium reagent is methyl lithium, isopropyl lithium, n-butyllithium, sec-butyl lithium, tert-butyl lithium or phenyl lithium.

The compound 3-i is refluxed under heating in sulfuric acid and dehydrated to obtain compound 4-i.

The compound 4-i is subjected to aldol condensation with paraformaldehyde in the catalysis of an alkali to obtain a compound 5-i, which further undergoes Cannizzaro reaction to obtain a compound 6-i.

The aldol condensation is performed at 50-120° C. in a solvent in the presence of 5-80 equivalents of the alkali for 6-12 h, where the alkali is potassium hydroxide, sodium hydroxide, lithium hydroxide, sodium methoxide, sodium ethoxide, sodium tert-butoxide or potassium tert-butoxide, the solvent is diethyl ether, tetrahydrofuran, 1, 4-dioxane or methyl tert-butyl ether.

The hydroxyl group of the compound 6-i and the leaving group are subjected to aromatic nucleophilic substitution reaction (SNAr) in the presence of an acid-binding agent, and 1, 1'-spirodihydrobenzofuran-7, 7'-difluoro (7-i) is obtained after cyclization. The compound 7-i is further subjected to aromatic nucleophilic substitution reaction with benzyl alcohol in the presence of the acid-binding agent to obtain a compound 8-i.

The acid-binding agent is an organic base, an inorganic base or a combination thereof. The organic base is triethylamine, N,N-diisopropylethylamine or pyridine. The inorganic base is cesium carbonate, potassium carbonate, lithium carbonate, sodium tert-butoxide, potassium tert-butoxide, sodium hydride, sodium hydroxide or potassium hydroxide. The aromatic nucleophilic substitution reaction is performed at −10-140° C. in a solvent in the presence of 5-100 equivalents of the acid-binding agent for 2-10 h, where the solvent is an organic solvent such as diethyl ether, tetrahydrofuran, 1,4-dioxane, tert-butyl methyl ether, toluene, p-toluene, p-xylene, o-xylene, chlorobenzene, dichlorobenzene and N,N-dimethyllformamide (DMF).

The compound 8-i is subjected to debenzylation in the presence of Pd/C-based metal catalyst to obtain a racemic 1, 1'-spirodihydrobenzofuran-7, 7'-diol (9-i).

The debenzylation is performed at 25-40° C. and a hydrogen pressure of 0.1-5 MPa in a solvent in the presence of 5-10% (w/w) of the catalyst for 5-12 h, where the Pd/C-based metal catalyst contains at least 5% of Pd/C, and the solvent is an organic solvent such as diethyl ether, tetrahydrofuran, 1, 4-dioxane and methyl tert-butyl ether.

Tert-butanol is dehydrated under the catalysis of a protonic acid or Lewis acid to produce isobutylene, which is subjected to electrophilic addition with the compound 9-i to obtain a target diphenol product rac-O-SPINOL (10-i).

The protonic acid or Lewis acid is an organic acid, an inorganic acid or a combination thereof. The organic acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluenesulfonic acid and a combination thereof. The inorganic acid is selected from the group consisting of hydrobromic acid, hydrochloric acid, hydrofluoric acid, sulfurous acid, sulfuric acid, perchloric acid, phosphonic acid, pyrophosphoric acid, nitric acid, nitrous acid, chromic acid, magic acid, fluoroantimonic acid and a combination thereof. An alkylating agent is selected from the group consisting of tert-butyl bromide, tert-butyl chloride, isobutene and tert-butanol. A reaction temperature is 50-110° C. A reaction solvent is selected from benzene, toluene, p-toluene, p-xylene, o-xylene, chlorobenzene and dichlorobenzene.

The rac-O-SPINOL and an organic solvent are successively added into a reaction vessel under a nitrogen atmosphere to obtain a mixed solution; or the rac-O-SPINOL and an organic solvent are successively added into a reaction vessel under a nitrogen atmosphere, to which n-butyllithium is added dropwise at a −78~−10° C., and the reaction mixture is restored to room temperature to obtain a lithiation product.

The mixed solution is dropwise added with a mixture including a chlorophosphite or chlorophosphoramidite compound and an acid-binding agent, and subjected to esterification at room temperature under reflux conditions, removal of inorganic salts and concentration to obtain a crude product, or the lithiation product is added with an organic solution of the chlorinated form of the above-listed chlorophosphite or chlorophosphoramidite (L1-L40), and subjected to esterification under reflux conditions, removal of inorganic salts and concentration to obtain a crude product, where the chlorophosphite compound includes an aryl group selected from the group consisting of a biphenyl group, a methylene diphenyl group, a binaphthyl group, a benzoyloxy group, an o-phenyl group, a phenyl group and a naphthyl group; or a chlorophosphoramidite structure including pyrrolyl, imidazolyl, carbazolyl or pyridyl.

The esterification between the rac-O-SPINOL and the chlorophosphite or chlorophosphoramidite compound is performed in the presence of 5-20 equivalents of the acid-binding agent for 12-48 h, where the acid-binding agent is selected from triethylamine, N,N-diisopropylethylamine and pyridine. The esterification between the lithiation product and the chlorinated form of the above-listed chlorophosphite or chlorophosphoramidite (L1-L40) is performed at −78-80° C. in the presence of 2-4 equivalents of n-butyllithium for 12-48 h. The organic solvent is selected from toluene, tetrahydrofuran, diethyl ether, 2-methyltetrahydrofuran, methyl tert-butyl ether, isopropyl ether, anisole, ethylene glycol dimethyl ether, diethylene glycol dimethyl ether, butyl ether, cyclopentyl methyl ether and 1,4-dioxane.

The crude product is purified by crystallization with a solvent, which is selected from the group consisting of ethyl acetate, toluene, dichloromethane, ethanol, acetonitrile, petroleum ether, n-hexane, tetrahydrofuran and a combination thereof.

In an embodiment, the SPINOL is (±)-SPINOL, (+)-SPINOL or (−)-SPINOL. The spiro-bisphosphorous compound is (±)-spiro-bisphosphite compound, (+)-spiro-bisphosphite compound or (−)-spiro-bisphosphite compound. The resolution of the chiral SPINOL compound could be efficiently performed by means of a resolution reagent such as D-proline, L-menthyl chloroformate and N-benzylcinchoninium chloride (chiral phase transfer catalyst), expressed as follows:

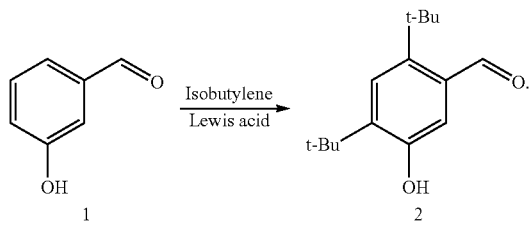

A complex of the racemic spiro-bisphosphorous (rac-SPINOL, rac-O-SPINOL) compound and a transition metal precursor (e.g., Rh, Pt, Pd, Ru and Ir) is capable of catalyzing the carbonylation of olefins, such as hydroformylation, isomerization-hydroformylation, alkoxycarbonylation, hydroaminomethylation, hydroaminocarbonylation, hydroxycarbonylation and hydroalkoxycarbonylation.

A complex of the chiral spiro-bisphosphorous compound and a transition metal precursor (e.g., Rh, Pt, Pd, Ru and Ir) is capable of catalyzing an asymmetric reaction, such as hydrogenation, hydroformylation, hydrosilylation, hydroboration, hydrohydroxylation, hydroamination, hydrocyanation, isomerization formylation, hydroaminomethylation, transfer hydrogenation, allylation, olefin metathesis, cycloisomerization, Diels-Alder reaction, asymmetric coupling reaction, Aldol reaction, Michael addition reaction, asymmetric epoxidation, kinetic resolution and [m+n] cyclization.

This application also provides a catalytic complex, including a racemic spiro-bisphosphorous compound and a transition metal precursor (e.g., Rh, Pt, Pd, Ru and Ir). The racemic spiro-bisphosphorous compound is selected from the group consisting of compounds of formula (I) except for (R,S)-L12, (R,S)-L13, (R,S)-L17 and (R,S)-L31. Alternatively, the catalytic complex includes a chiral spiro-bisphosphorous compound and a transition metal precursor (e.g., Rh, Pt, Pd, Ru and Ir). The chiral spiro-bisphosphorous compound is selected from the group consisting of compounds L1-L31 of formula (I) and (II) and compounds L1-L41 of formula (III).

Furthermore, this application provides an application of the spiro-bisphosphorous compound, including:
catalyzing the hydroformylation of olefins and syngas in the presence of the above-mentioned catalytic complex to produce straight-chain aldehydes.

Specifically, the above-mentioned spiro-bisphosphorous compound and a transition metal catalyst are sequentially added into an organic solvent in a reaction device under the protection of inert gas, and stirred at room temperature for complexation, where a molar ratio of phosphine in the spiro-bisphosphorous compound to the transition metal catalyst is (1-5):1.

Under the protection of inert gas, liquified etherified C4, methanol-to-olefins (MTO) C4, cis-2-butene or trans-2-butene is added into the reaction device and stirred evenly at room temperature, where the transition metal catalyst is controlled at 50-220 ppm.

Hydrogen and carbon monoxide are fed into the reaction device, where a pressure ratio of the hydrogen to carbon monoxide is 1(1-5), and a total pressure is 0.5-1 MPa. The reaction mixture is reacted under stirring at 40-100° C. for 1-4 hours.

In the above-mentioned hydroformylation, the etherified C4 or the MTO C4 consists of: 0-30 wt % of 1-butene, 0-70 wt % of trans-2-butene, 0-40 wt % of cis-2-butene, 0-30 wt % of n-butane, 0-20 wt % of isobutane and 0-10 wt % of isobutylene.

The disclosure will be further described below with reference to embodiments. Raw materials in each embodiment corresponds to the raw materials in a synthesis route thereof. Serial numbers of compounds in each embodiment are merely limited into the corresponding synthetic route.

Example 1 Preparation of 2,4-di-tert-butyl-5-hydroxybenzaldehyde (2)

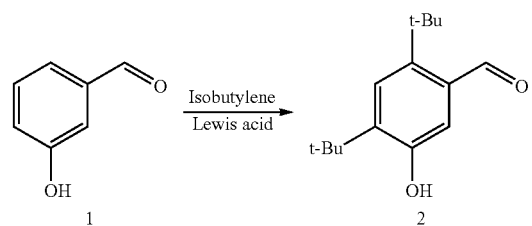

To a 2 L two-necked flask was added compound 1 (20.0 g, 163.8 mmol). Then 200 mL of tetrahydrofuran and 2.5 g of concentrated sulfuric acid were added into the two-necked flask at 25° C. under nitrogen atmosphere. To the two-necked flask was continuously fed 1.5 atmospheres of isobutylene. The reaction mixture was heated to 100° C. and reacted for 12 h, and then quenched by water. After that, the reaction mixture was added with 300 mL of water and subjected to extraction three times with ethyl acetate (each for 300 mL). The organic phases were combined, dried by anhydrous sodium sulfate and evaporated under vacuum to obtain 35.7 g of a pale-yellow solid as compound 2 (94% yield).

$^1$H NMR (400 MHz, CDCl$_3$): δ=1.35 (s, 9H), 1.41 (s, 9H), 6.54 (s, 1H), 7.30 (d, 1H), 7.38 (s, 1H), 9.89 (d, 1H)

Example 2 Preparation of 2-methoxy-4-tert-butyl-5-hydroxybenzaldehyde (2a)

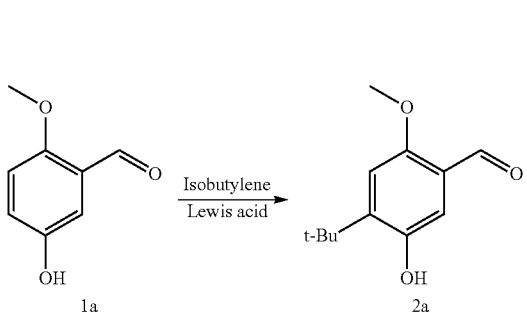

The preparation of compound 2a was similar to that of compound 2. 20 g of compound 1a was added, and 26.3 g of a yellow solid was produced as compound 2a (96% yield).

$^1$H NMR (400 MHz, CDCl$_3$): δ=1.39 (s, 9H), 3.89 (s, 3H), 6.62 (s, 1H), 6.96 (s, 1H), 7.36 (d, 1H).

Example 3 Preparation of 1,5-bis(2, 4-di-tert-butyl-5-hydroxyphenyl)-1, 4-pentadien-3-one (3)

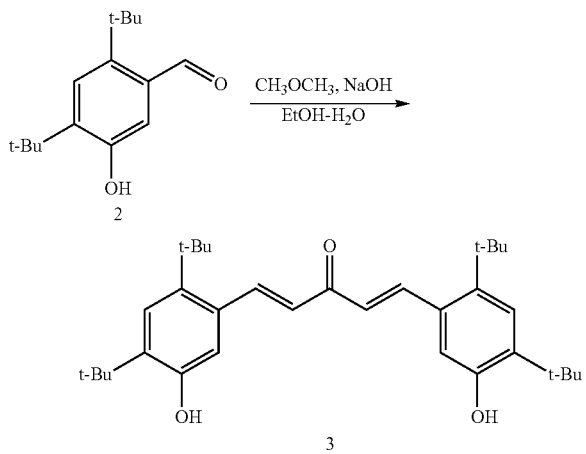 [SMILES: "EtOH-H2O" ; CC(C)(C)c1cc(C(C)(C)C)c(C=O)cc1O ; CC(C)(C)c1cc(C(C)(C)C)c(/C=C/C(=O)/C=C/c2cc(O)c(C(C)(C)C)cc2C(C)(C)C)cc1O]

To a 500 mL two-necked flask were added compound 2 (20.0 g, 85.3 mmol), acetone (3.1 mL, 42.7 mmol) and 125 mL of ethanol. The reaction mixture was transferred to a 200 mL dropping funnel, to which 400 mL of an ethanol-water solution of sodium hydroxide (19.0 g NaOH, EtOH-H$_2$O: 65%) was slowly added dropwise. Then the reaction mixture was stirred at room temperature for 2 h. The organic phase was collected, diluted with dichloromethane, washed with water, dried with anhydrous sodium sulfate and separated by column chromatography to obtain 19.3 g of pale-yellow oily product as compound 3 (92% yield), which was subjected to standing for solidification.

$^1$H NMR (400 MHz, CDCl$_3$): δ=1.31 (s, 18H), 1.38 (s, 18H), 6.60 (s, 2H), 6.70-6.83 (m, 4H), 7.35 (s, 2H), 7.75 (d, 2H).

Example 4 Preparation of 1, 5-bis(2-methoxy-4-tert-butyl-5-hydroxyphenyl)-1, 4-pentadien-3-one (3a)

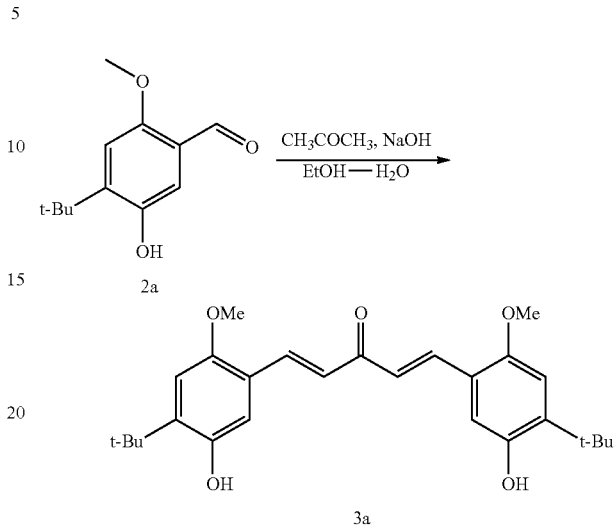

The preparation of compound 3a was similar to that of compound 3. 20 g of compound 2a was added, and 19.6 g of a yellow oily product was produced as compound 3a (95% yield).

$^1$H NMR (400 MHz, CDCl$_3$): δ=1.43 (s, 18H), 3.88 (s, 6H), 6.69-7.01 (m, 8H), 7.82 (d, 2H).

Example 5 Preparation of 1,5-bis(2,4-di-tert-butyl-5-hydroxyphenyl)-3-pentanone (4)

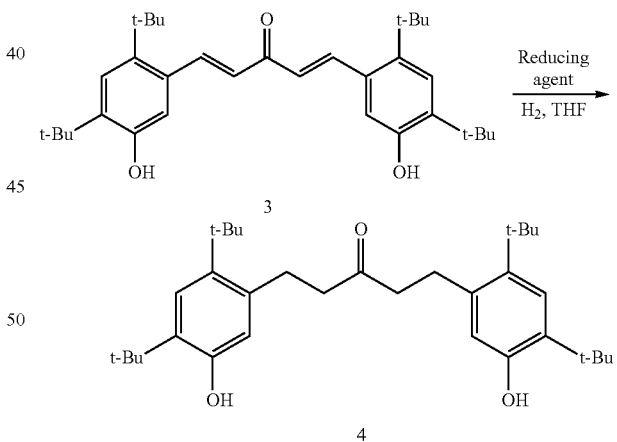

To a 500 mL round-bottomed flask were sequentially added compound 3 (15.0 g, 30.6 mmol), 200 mL of acetone and 60 g of Raney nickel. A hydrogen bag was provided, and the reaction mixture was reacted under stirring under hydrogen atmosphere. When the reaction was confirmed by TLC to be completed, the reaction mixture was filtered to remove the catalyst, which was further washed by acetone. The filtrate was dried under reduced pressure to obtain 14.97 g of a colorless oily product as compound 4 (99% yield).

$^1$H NMR (400 MHz, CDCl$_3$): δ=1.36 (d, 36H), 2.71-3.03 (m, 8H), 6.07 (s, 2H), 6.54 (t, 2H), 7.15 (s, 2H).

Example 6 Preparation of 1, 5-bis(2-methoxy-4-tert-butyl-5-hydroxyphenyl)-3-pentanone (4a)

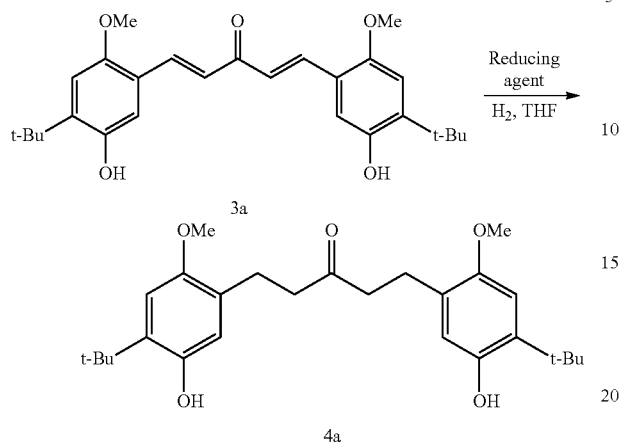

The preparation of compound 4a was similar to that of compound 4. 15 g of compound 3a was added, and 14.7 g of a yellow oily product was obtained as compound 4a (97% yield).

$^1$H NMR (400 MHz, CDCl$_3$): δ=1.43 (s, 18H), 2.75-2.91 (m, 8H), 3.73 (s, 6H), 6.03 (s, 2H), 6.42 (t, 2H), 6.77 (s, 2H).

Example 7 Preparation of 4, 4', 6, 6'-tetra-tert-butyl-1, 1'-spirobiindane-7, 7'-diol (5)

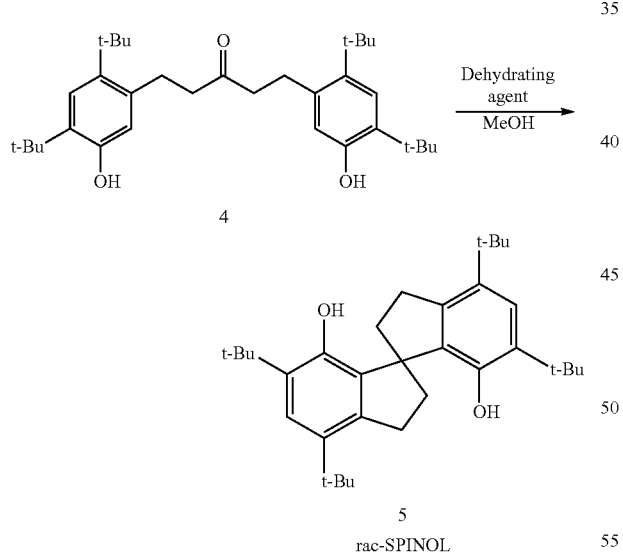

To a 500 mL round-bottomed flask were sequentially added compound 4 (11.0 g, 22.2 mmol), 105 g of polyphosphoric acid. The reaction mixture was heated to 120° C. and reacted under stirring for 6 h. Then the reaction mixture was subjected to washing with water, extraction with ethyl acetate to obtain an organic phase, which was evaporated under reduced pressure to obtain a crude product. The crude product was purified by column chromatography and crystallization with n-hexane to obtain 22.8 g of compound 5 (78% yield).

$^1$H NMR (400 MHz, CDCl$_3$): δ=1.37 (d, 36H), 2.31 (m, 4H), 3.04-3.27 (m, 4H), 5.44 (s, 2H), 7.09 (s, 2H).

Example 8 Preparation of 4, 4'-dimethoxy-6, 6'-di-tert-butyl-1, 1'-spirobiindane-7, 7'-diol (5a)

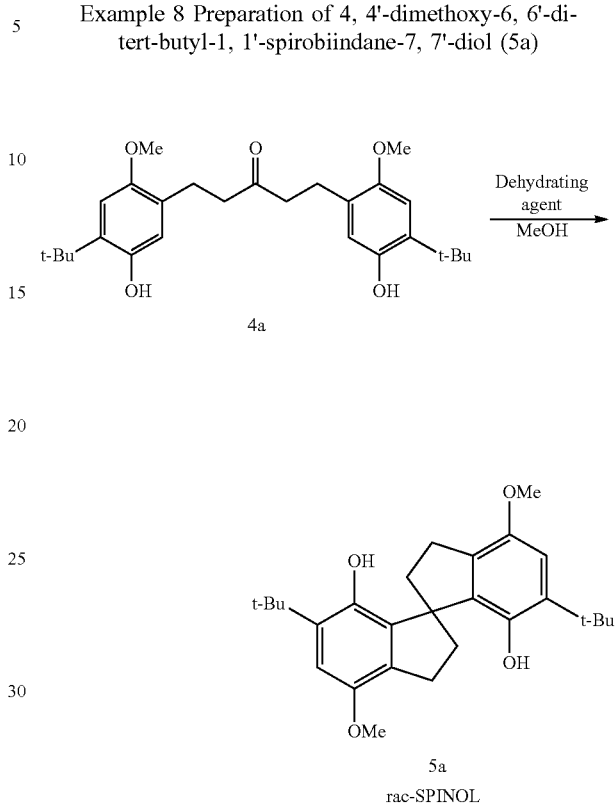

The preparation of compound 5a was similar to that of compound 5. 11.0 g of compound 4a was added, and 14.7 g of compound 5a was obtained (81% yield).

$^1$H NMR (400 MHz, CDCl$_3$): δ=1.44 (s, 18H), 2.52-2.18 (m, 4H), 2.91-3.11 (m, 4H), 3.79 (s, 6H), 5.25 (s, 2H), 6.66 (s, 2H).

Example 9 Preparation of 7, 7'-bis[(1, 1'-biphenyl-2, 2'-diyl)phosphite]-4, 4', 6, 6'-tetra-tert-butyl-1, 1'-spirobiindane (6-L4)

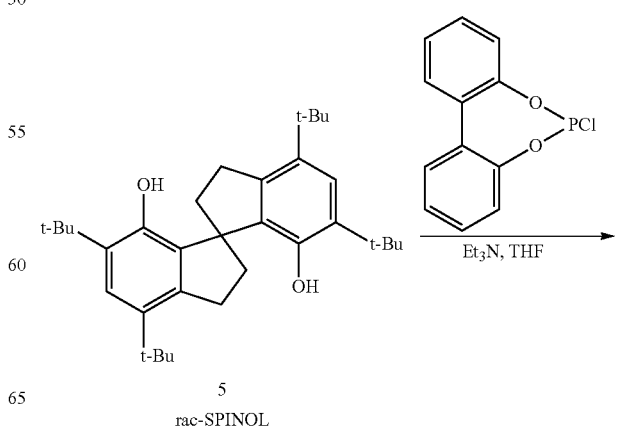

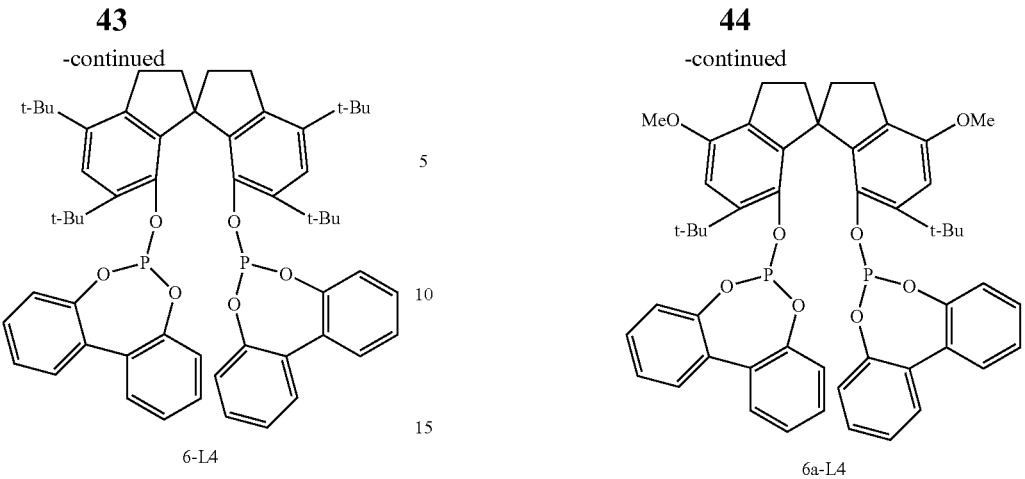

6-L4

6a-L4

To a dry 500 mL Schlenk flask were added compound 5 (5.0 g, 10.5 mmol), anhydrous triethylamine (21.9 mL, 157.5 mmol, 15 eq.) and 80 mL of anhydrous tetrahydrofuran under nitrogen atmosphere. The reaction mixture was cooled to −40° C., dropwise added with 60 mL of a solution of 1,1'-dioxyphosphine chloride (6.6 g, 26.3 mmol, 2.5 equiv.) in anhydrous tetrahydrofuran and reacted at room temperature for 24 h. The reaction mixture was concentrated under nitrogen atmosphere, separated by column chromatography and recrystallized with acetonitrile to obtain 5.6 g of compound 6-L4 (59% yield).

Figure 2:
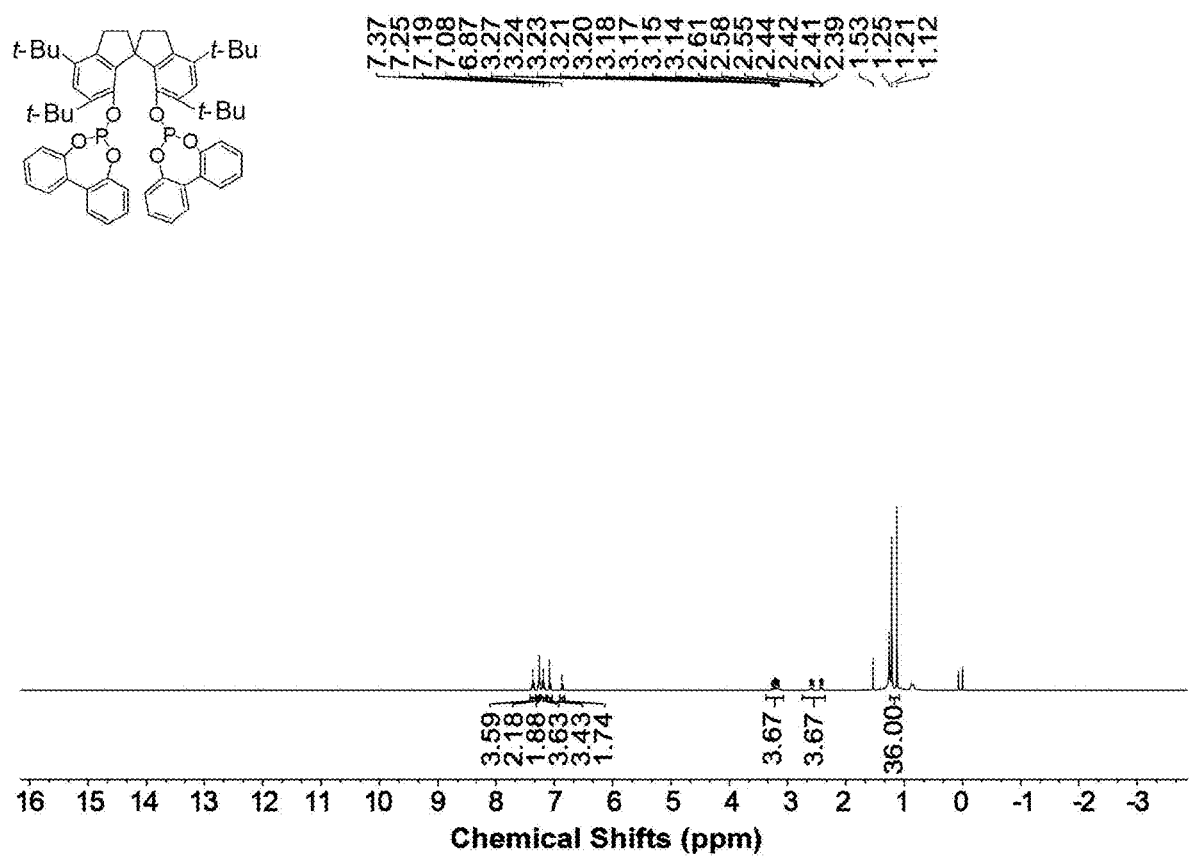
FIG. 2 shows a $^1$H NMR spectrum of 7, 7'-bis[(1, 1'-biphenyl-2, 2'-diyl)phosphite]-4, 4', 6, 6'-tetra-tert-butyl-1, 1'-spirobiindane prepared in Example 9.
Figure 3:
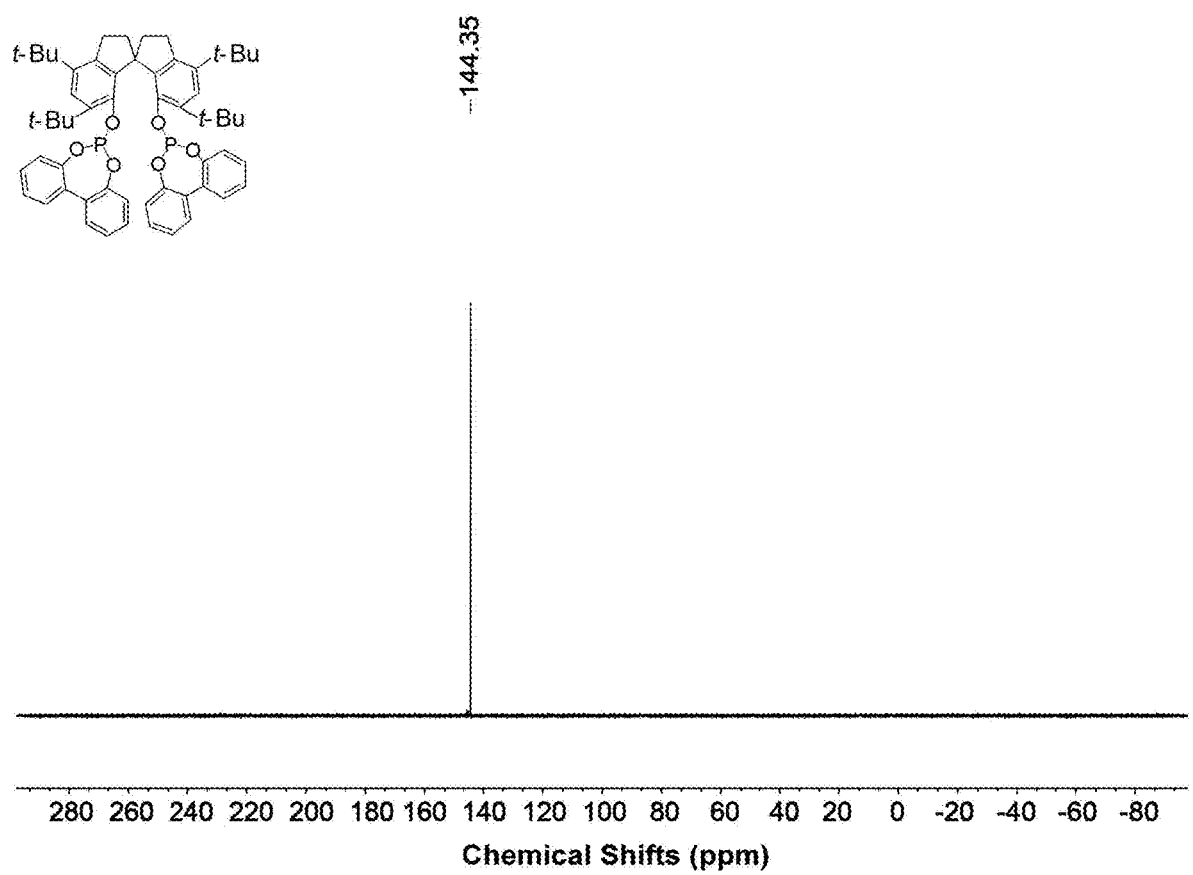
FIG. 3 shows a $^{31}$P NMR spectrum of 7, 7'-bis[(1, 1'-biphenyl-2, 2'-diyl)phosphite]-4, 4', 6, 6'-tetra-tert-butyl-1, 1'-spirobiindane prepared in Example 9.

$^1$H NMR (600 MHz, CDCl$_3$): δ=1.17 (d, 36H), 2.35-2.74 (m, 4H), 3.07-3.36 (m, 4H), 6.87 (s, 2H), 7.08 (s, 3H), 7.19 (s, 4H), 7.25 (s, 2H), 7.26-7.31 (m, 2H), 7.37 (s, 4H) (FIG. 2); and $^{31}$P NMR (243 MHz, CDCl$_3$): δ=144.35 (FIG. 3).

Example 10 Preparation of 7, 7'-bis[(1, 1'-biphenyl-2, 2'-diyl)phosphite]-4, 4'-dimethoxy-6, 6'-di-tert-butyl-1, 1'-spirobiindane (6a-L4)

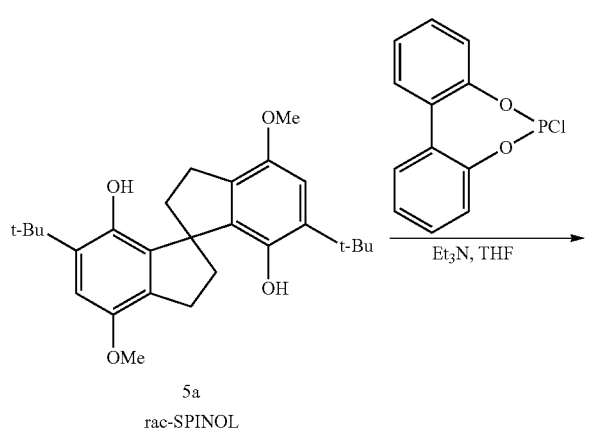

5a
rac-SPINOL

The preparation of compound 6a-L4 was similar to that of compound 6-L4. 5.0 g of compound 5a was added, and 4.6 g of compound 6a-L4 was obtained (46% yield).

$^1$H NMR (600 MHz, CDCl$_3$): δ=1.45 (s, 18H), 2.37 (m, 4H), 3.02 (m, 4H), 3.78 (s, 6H), 6.70 (s, 2H), 6.97-7.13 (m, 8H), 7.30 (td, 4H), 7.69 (dd, 4H); and $^{31}$P NMR (243 MHz, CDCl$_3$): δ=140.59.

Example 11 Preparation of 2-bromo-5-hydroxybenzaldehyde (2")

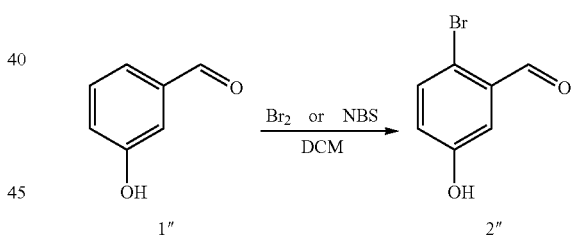

To a 2 L two-necked flask were sequentially added compound 1" (100 g, 819 mmol) and 1.0 L of dichloromethane. To a dropping funnel loaded with 800 mL of dichloromethane was added bromine (42 mL, 819 mmol). The reaction mixture was dropwise added with the bromine solution and then reacted under stirring for 1.5 h. After that, the reaction mixture was subjected to filtration by means of a sand core funnel, and a filter cake was collected, dried with hexane and further dried under reduced pressure overnight to obtain 91.7 g of a white solid as compound 2" (56% yield), which can be directly applied without purification.

$^1$H NMR (400 MHz, CDCl$_3$): δ=5.75 (br. s, 1H), 7.00 (dd, 1H), 7.42 (d, 1H), 7.50 (d, 1H), 10.27 (s, H).

Example 12 Preparation of 1, 5-bis(3-methoxyphenyl)-1, 4-pentadien-3-one (2')

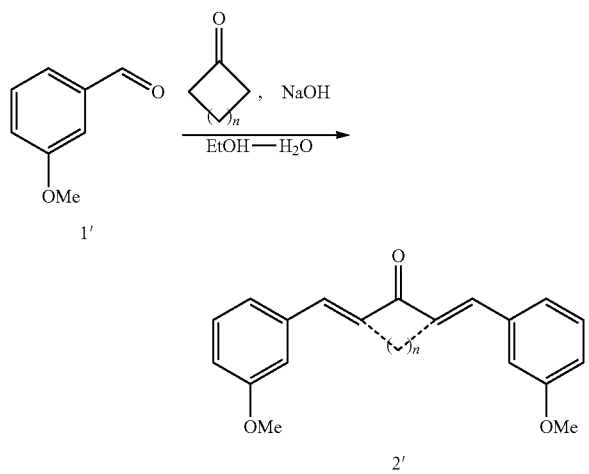

To a 200 mL two-necked flask were added compound 1' (10.0 g, 73.4 mmol), acetone (n=0, 2.70 mL, 36.8 mmol) and 50 mL of ethanol to obtain a mixed solution. The mixed solution was transferred to a 200 mL dropping funnel, to which 150 mL of an ethanol-water solution of sodium hydroxide (7.5 g NaOH, EtOH-H$_2$O: 50%) was slowly added dropwise. The reaction mixture was reacted under stirring at room temperature for 2 h. The organic phase was collected, diluted with dichloromethane, washed with water, dried with anhydrous sodium sulfate and separated by column chromatography to obtain 6.66 g of a yellow oily product as compound 2' (62% yield), which was subjected to standing for solidification.

$^1$H NMR (400 MHz, CDCl$_3$): δ=3.83 (s, 6H), 6.97 (dd, 2H), 7.07 (d, 2H), 7.14 (m, 2H), 7.22 (br. d, 2H), 7.34 (t, 2H), 7.71 (d, 2H).

Example 13 Preparation of 1, 5-bis(2-bromo-3-hydroxyphenyl)-1, 4-pentadien-3-one (3")

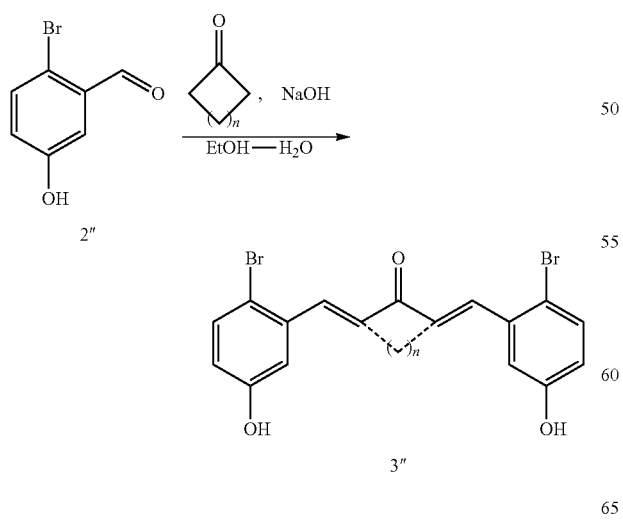

To a 500 mL two-necked flask were added compound 2" (50.0 g, 248.8 mmol), acetone (n=0, 9.2 mL, 124.4 mmol) and 250 mL of ethanol to obtain a mixed solution. The mixed solution was transferred to a 500 mL dropping funnel, to which 800 mL of an ethanol-water solution of sodium hydroxide (38.0 g NaOH, EtOH-H$_2$O: 50%) was slowly added dropwise. The reaction mixture was reacted under stirring at room temperature for 2 h. The organic phase was collected, diluted with dichloromethane, washed with water, dried with anhydrous sodium sulfate and separated by column chromatography to obtain 27.1 g of pale-yellow oily product as compound 3" (51.7% yield), which was subjected to standing for solidification.

$^1$H NMR (400 MHz, DMSO): δ=6.58 (m, 4H), 6.86 (d, 2H), 7.32 (d, 2H), 8.09 (d, 2H), 9.45 (br. s, 2H).

Example 14 Preparation of 1, 5-bis(2-bromo-3-methoxyphenyl)-1, 4-pentadien-3-one (3')

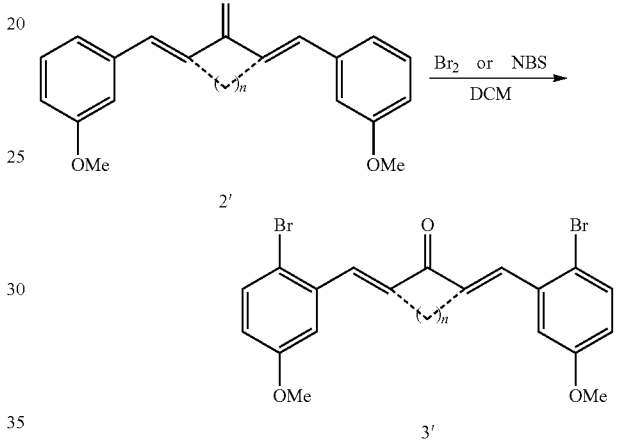

10.0 g of compound 2' was dissolved in 50 mL of dichloromethane in a 500 mL round-bottomed flask, to which pyridine (10 mL, 120 mmol) was added. The reaction mixture was cooled to −10° C. and dropwise added with a solution of bromine in dichloromethane (10% v/v, 44 mL, 86 mmol). After that, the reaction mixture was restored to room temperature, stirred for 4 h and added with an aqueous NaHSO$_3$ solution to remove excess bromine. Then the reaction mixture was washed with dilute hydrochloric acid and water, dried with anhydrous sodium sulfate and evaporated under reduced pressure to obtain 14.8 g of a light-yellow oily product as compound 3' (95% yield).

$^1$H NMR (400 MHz, CDCl$_3$): δ=2.74 (t, 4H), 2.96 (t, 4H), 3.81 (s, 6H), 6.63 (dd, 2H), 6.78 (d, 2H), 7.39 (d, 2H).

Example 15 Preparation of 1, 5-bis(2-bromo-3-methoxyphenyl)-3-pentanone (4') or 1, 5-bis(2-bromo-3-hydroxyphenyl)-3-pentanone (4")

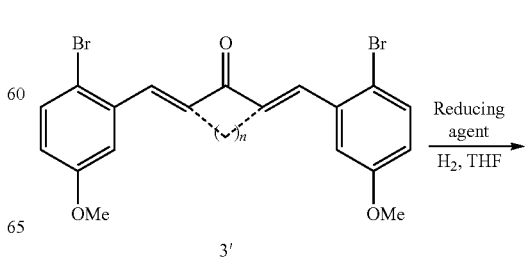

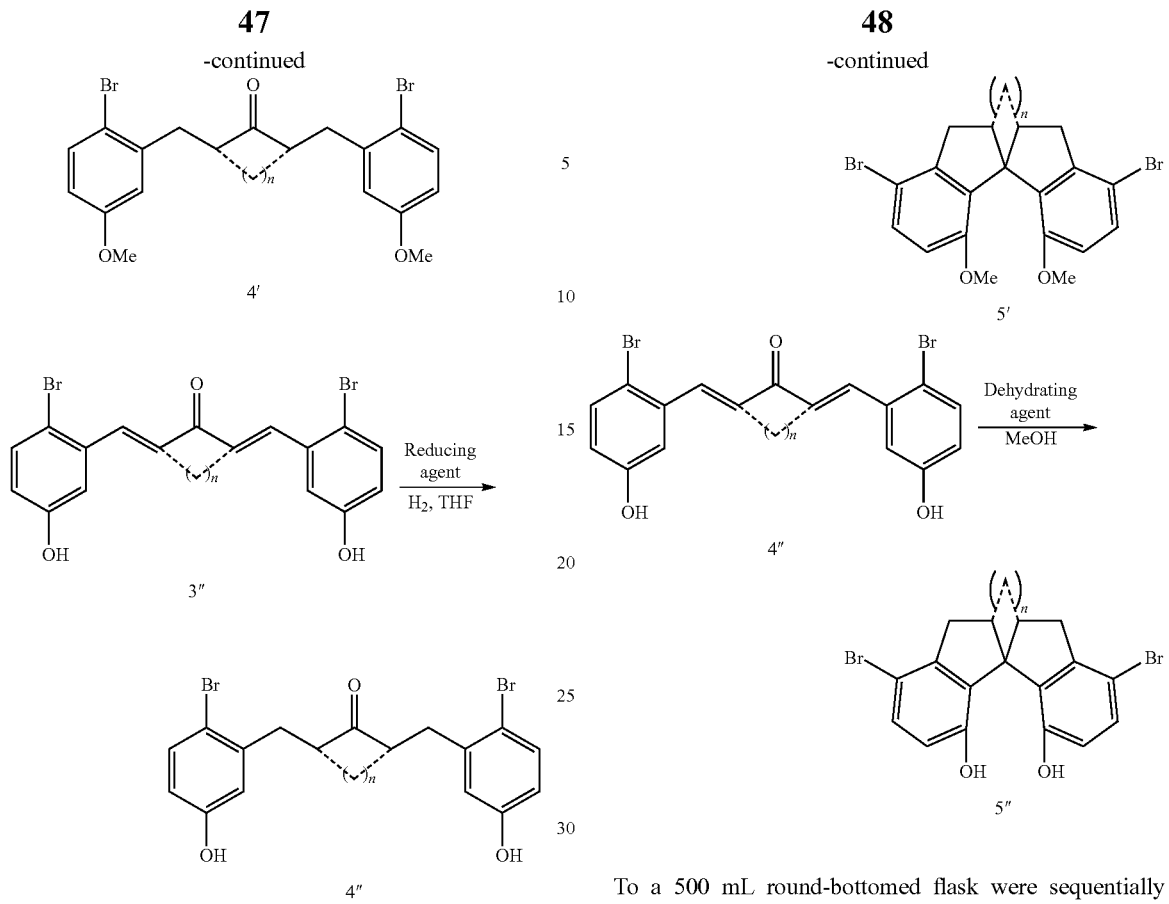

To a 200 mL round-bottomed flask were sequentially added compound 3' or compound 3" (5.0 g, 17.0 mmol), 70 mL of acetone and 20 g of Raney nickel. A hydrogen bag was provided, and the reaction mixture was reacted under stirring under hydrogen atmosphere. After the reaction was confirmed by TLC to be completed, the reaction mixture was filtered to remove the catalyst, which was further washed by acetone. The filtrate was dried under reduced pressure to obtain 4.93 g of colorless oily compound 4' (97% yield) or 4.82 g of compound 4" (95% yield).

Compound 4': $^1$H NMR (400 MHz, CDCl$_3$): δ=2.71 (t, 4H), 2.86 (t, 4H), 3.78 (s, 6H), 6.73 (m, 4H), 7.19 (t, 2H).

Compound 4": $^1$H NMR (400 MHz, CDCl$_3$): δ=2.78-2.80 (m, 4H), 6.60-6.63 (m, 4H), 7.38 (d, 2H), 9.29 (s, 2H).

Example 16 Preparation of 4, 4'-dibromo-7, 7'-dimethoxy-1, 1'-spirobiindane (5') or 4, 4'-dibromo-7, 7'-dihydroxy-1, 1'-spirobiindane (5")

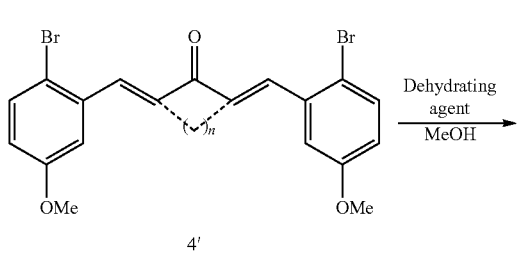

To a 500 mL round-bottomed flask were sequentially added compound 4' or 4" (32.0 g, 74.7 mmol) and 260 g of polyphosphoric acid. The reaction mixture was heated to 60° C. and reacted under stirring for 6 h. After that, the reaction mixture was subjected to washing with water and extraction with ethyl acetate. The organic phase was collected, and evaporated under reduced pressure to obtain a crude product, which was then subjected to separation by column chromatography and crystallization with n-hexane to obtain 22.8 g of compound 5' (67% yield) or 26.9 g of compound 5" (75% yield).

Compound 5': $^1$H NMR (400 MHz, CDCl$_3$): δ=2.16 (m, 2H), 2.31 (m, 2H), 2.96 (m, 2H), 3.05 (m, 2H), 3.52 (s, 6H), 6.52 (d, 2H), 7.26 (d, 2H).

Compound 5": $^1$H NMR (400 MHz, CDCl$_3$): δ=2.14 (m, 2H), 2.27 (m, 2H), 3.11-3.16 (m, 4H), 6.55 (d, 2H), 7.15 (d, 2H), 9.68 (d, 2H).

Example 17 Preparation of 7, 7'-dimethoxy-1, 1'-spirobiindane (6')

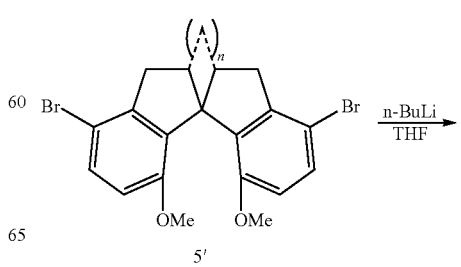

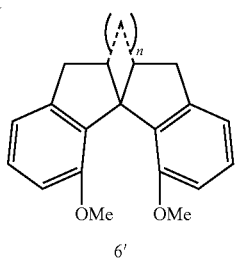

6'

To a dry 200 mL Schlenk flask were added compound 5' (2.5 g, 5.5 mmol) and 60 mL of tetrahydrofuran, and the atmosphere in the Schlenk flask was replaced with nitrogen atmosphere. The reaction mixture was cooled to −78° C., dropwise added with 2.5 M n-butyllithium (9.0 mL, 4.0 eq) and reacted for 1 h. After that, the reaction mixture was quenched with 2.5 mL of ethanol, washed with water and subjected to extraction with dichloromethane. The organic phase was collected, dried with anhydrous sodium sulfate and evaporated under reduced pressure to obtain a crude product. The crude product was recrystallized with hexane to obtain 1.5 g of compound 6' (93% yield).

$^1$H NMR (400 MHz, CDCl$_3$): δ=2.16 (m, 2H), 2.32 (m, 2H), 2.99 (m, 2H), 3.03 (m, 2H), 3.52 (s, 6H), 6.62 (d, 2H), 6.85 (d, 2H), 7.12 (t, 2H).

Example 18 Preparation of 1, 1'-spirobiindane-7, 7'-diol (6")

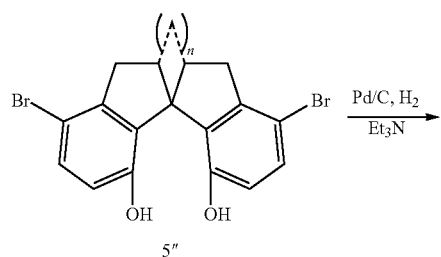

6"

To a 1 L round-bottomed flask were sequentially added compound 5" (24 g, 58.5 mmol), 160 mL of ethyl acetate, 50 mL of deionized water, 160 mL of triethylamine (1.16 mol) and 2.3 g of a catalyst (10% Pd/C). A hydrogen bag was provided, and the reaction mixture was reacted. After the reaction was confirmed by HPLC to be completed, the reaction mixture was filtered with diatomite to obtain a filtrate. The filtrate was subjected to washing with 5% hydrochloric acid aqueous solution, and an organic phase was collected, dried with anhydrous sodium sulfate, filtered, evaporated under reduced pressure and separated by column chromatography to obtain 10.6 g of a white solid as compound 6" (72% yield).

$^1$H NMR (400 MHz, CDCl$_3$): δ=2.19 (m, 2H), 2.30 (m, 2H), 3.03 (m, 4H), 4.61 (s, 2H), 6.68 (d, 2H), 6.89 (d, 2H), 7.17 (t, 2H).

Example 19 Preparation of 1, 1'-spirobiindane-7, 7'-diol (7')

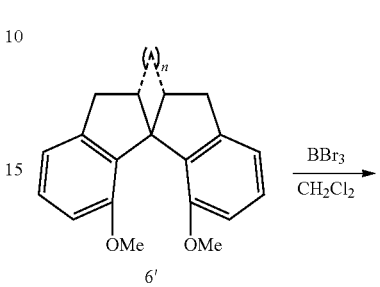

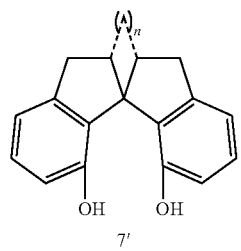

7'

To a dry 500 mL Schlenk flask were added compound 6' (7.6 g, 27.1 mmol) and 120 mL of dichloromethane, and then the atmosphere in the flask was replaced with nitrogen. The reaction mixture was cooled to −78° C., dropwise added with 62.0 mL of a solution of boron tribromide in dichloromethane (1 M), restored to room temperature and kept overnight. The reaction mixture was quenched by water, and subjected to extraction with dichloromethane, and an organic phase was collected, dried with anhydrous sodium sulfate and evaporated under reduced pressure to obtain a crude product. The crude product was recrystallized with hexane to obtain 6.0 g of compound 7' (85% yield).

$^1$H NMR (400 MHz, CDCl$_3$): δ=2.19 (m, 2H), 2.30 (m, 2H), 3.03 (m, 4H), 4.61 (s, 2H), 6.68 (d, 2H), 6.89 (d, 2H), 7.17 (t, 2H).

Example 20 Preparation of 4, 4', 6, 6'-tetra-tert-butyl-1, 1'-spirobiindane-7, 7'-diol (8', rac-SPINOL)

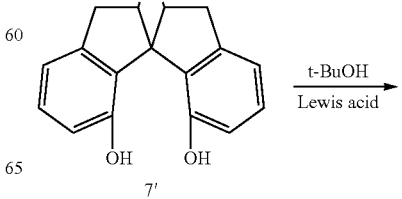

7'

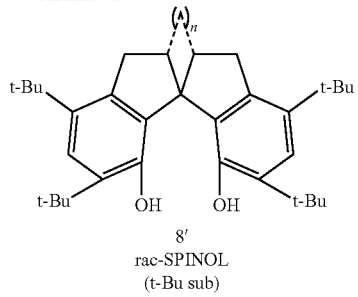

8'
rac-SPINOL
(t-Bu sub)

To a 2 L three-necked flask were sequentially added 70 g of compound 7', 125 g of tert-butanol and 85 g of concentrated sulfuric acid. The reaction mixture was heated and reacted under reflux in a nitrogen atmosphere for 24 h. The reaction mixture was evaporated under reduced pressure, added with 400 mL of water, and subjected to extraction with ethyl acetate. The organic phase was collected, dried with anhydrous sodium sulfate, evaporated under reduced pressure and separated by column chromatography to obtain 119 g of compound 8' (92% yield).

$^1$H NMR (400 MHz, CDCl$_3$): δ=1.37 (d, 36H), 2.31 (m, 4H), 3.04-3.27 (m, 4H), 5.44 (s, 2H), 7.09 (s, 2H).

Example 21 Preparation of 7, 7'-bis[(1, 1'-biphenyl-2, 2'-diyl)phosphite]-4, 4', 6, 6'-tetra-tert-butyl-1, 1'-spirobiindane (9'-L4)

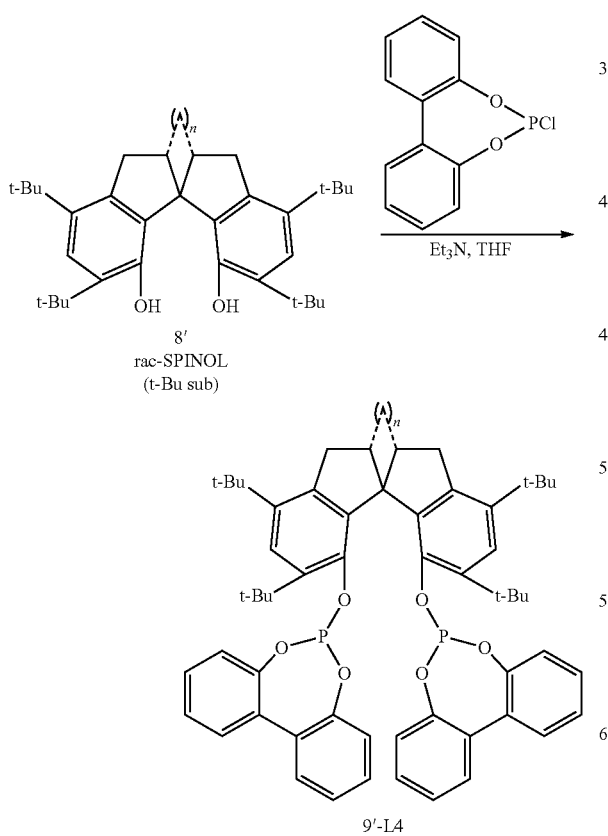

To a dry 500 mL Schlenk flask were added 3.2 g of rac-SPINOL (6.7 mmol), anhydrous triethylamine (14.0 mL, 100.5 mmol, 15 eq.) and 80 mL of anhydrous tetrahydrofuran under nitrogen atmosphere. The reaction mixture was cooled to −40° C., dropwise added with 60 mL of a solution of 1,1'-dioxyphosphine chloride (4.2 g, 16.78 mmol, 2.5 equiv.) in anhydrous tetrahydrofuran and reacted at room temperature for 24 h. The reaction mixture was concentrated under nitrogen atmosphere, separated by column chromatography and recrystallized with acetonitrile to obtain 3.5 g of compound 9'-L4 (57% yield). The $^1$H NMR spectrum of the compound 9'-L4 was basically same with that of Example 9.

Example 22 Preparation of Asymmetric spiro-bisphosphite ligand (rac-L33)

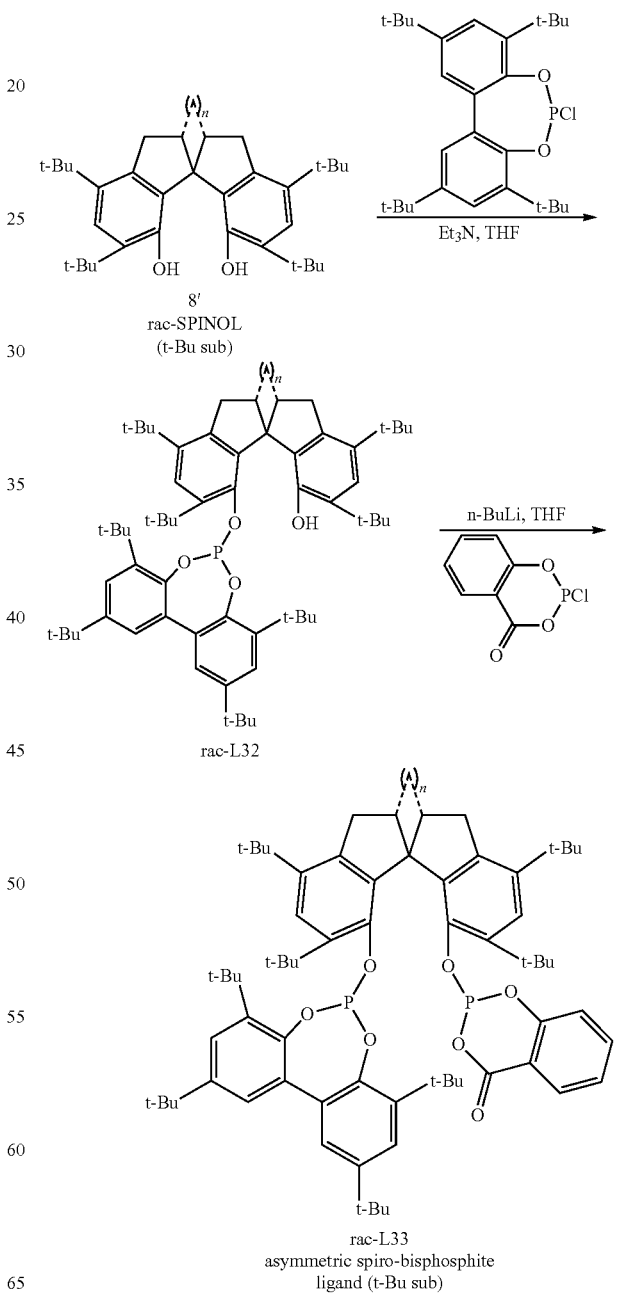

To a dry 500 mL Schlenk flask were added 3.2 g of rac-SPINOL (6.7 mmol), anhydrous triethylamine (7.0 mL, 50.3 mmol, 7.5 eq.) and 80 mL of anhydrous tetrahydrofuran under nitrogen atmosphere. The reaction mixture was cooled to −40° C., dropwise added with 60 mL of a solution of 3, 3', 5, 5'-tetra-tert-butyl-1, 1'-biphenyl-2, 2'-dioxyphosphine chloride (3.8 g, 8.0 mmol, 1.2 equiv.) in anhydrous tetrahydrofuran and reacted at room temperature for 24 h. The reaction mixture was concentrated under nitrogen atmosphere, separated by column chromatography and recrystallized with acetonitrile to obtain 5.3 g of rac-L32 (87% yield).

To a dry 500 mL Schlenk flask were added the rac-L32 (5.3 g, 5.8 mmol), 100 mL of anhydrous tetrahydrofuran under nitrogen atmosphere. The reaction mixture was cooled to −20° C., dropwise added with 2.5 M n-butyllithium (2.3 mL, 5.8 mmol, 1.0 eq.). The reaction mixture was restored to room temperature and reacted under reflux for 1 h. Then the reaction mixture was added dropwise into 20 mL of a solution of 2-chloro-1,3,2-benzodioxaphosphorin-4-one (1.4 g, 7.0 mmol, 1.2 equiv.) in anhydrous tetrahydrofuran at −40° C., and reacted at room temperature for 24 h. The reaction mixture was concentrated under nitrogen atmosphere and separated by column chromatography to obtain 2.6 g of rac-L33 (42% yield).

$^1$H NMR (600 MHz, CDCl$_3$): δ=1.10-1.65 (m, 72H), 2.07-2.49 (m, 4H), 2.95-3.39 (m, 4H), 6.89-7.59 (m, 9H), 7.93 (dd, 1H); and $^{31}$P NMR (243 MHz, CDCl$_3$): δ=121.15, 139.31.

Example 23 Preparation of (R,R)-7, 7'-bis[(1, 1'-biphenyl-2, 2'-diyl)phosphite]-4, 4', 6, 6'-tetra-tert-butyl-(R)-1, 1'-spirobiindane ((R,R,R)-L17)

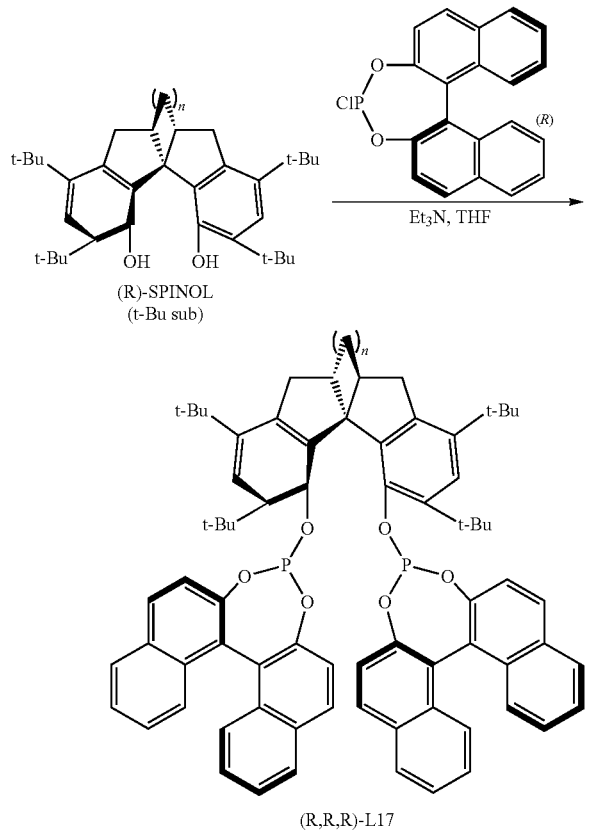

To a dry 500 mL Schlenk flask were sequentially added 2.4 g of (R)-4, 4', 6, 6'-tetra-tert-butyl-1, 1'-spirobiindane-7, 7'-diol (5.0 mmol), anhydrous triethylamine (17.4 mL, 125 mmol, 25 eq.) and 100 mL of anhydrous tetrahydrofuran under nitrogen atmosphere. The reaction mixture was cooled to −40° C., dropwise added with 100 mL of a solution of (R)-(1, 1'-binaphthyl-2, 2'-dioxy)chlorophosphine (3.9 g, 11.0 mmol, 2.2 equiv.) in anhydrous tetrahydrofuran and reacted at room temperature for 24 h. The reaction mixture was concentrated under nitrogen atmosphere, separated by column chromatography and crystallized with acetonitrile to obtain 4.0 g of (R,R,R)-L17 (73% yield).

$^1$H NMR (600 MHz, CDCl$_3$): δ=1.39 (s, 18H), 1.45 (s, 18H), 2.25-2.46 (m, 4H), 3.22 (m, 4H), 7.16 (s, 2H), 7.24-7.46 (m, 16H), 7.84 (d, 4H), 7.89-7.99 (d, 4H); and $^{31}$P NMR (243 MHz, CDCl$_3$): δ=142.72.

It should be noted that other spiro-bisphosphite ligands among L1-L31 of formula (I) and formula (II) can be prepared through the above process by using the corresponding chlorophosphite derivative.

Preparations of O-spiro-bisphosphite compounds with large steric hindrance were described below.

Example 24 Preparation of 2, 4-di-tert-butyl-5-methoxyphenol (2-2 or 2-3)

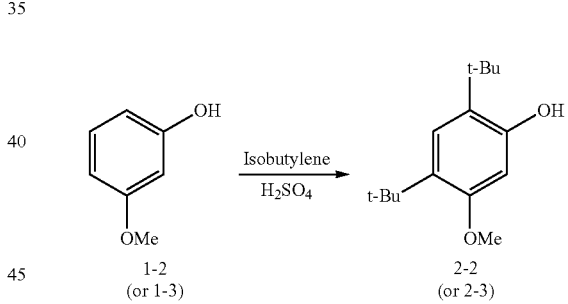

To a 2 L two-necked flask was added compound 1-2 or compound 1-3 (30.0 g, 241.7 mmol). Then 200 mL of tetrahydrofuran and 3.9 g of concentrated sulfuric acid were added at 25° C. under a nitrogen atmosphere, and 1.5 atmospheres of isobutylene was continuously fed to the two-necked flask. The reaction mixture was heated to 100° C., reacted for 12 h, and quenched with water. After that, the reaction mixture was added with 300 mL of water and subjected to extraction with ethyl acetate. An organic phase was collected, dried with anhydrous sodium sulfate and evaporated under reduced pressure to obtain 54.8 g of a pale-yellow solid as compound 2-2 or compound 2-3 (96% yield).

$^1$H NMR (400 MHz, CDCl$_3$): δ=1.39 (s, 9H), 1.44 (s, 9H), 3.84 (s, 3H), 6.32 (s, 1H), 6.72 (s, 1H), 7.17 (s, 1H).

Example 25 Preparation of 1, 5-bis(3-methoxyphenoxy)-2-propanol (2-1), 2, 4-di-tert-butyl-1, 5-bis(3-methoxyphenoxy)-2-propanol (3-2) or 2, 4-di-tert-butyl-1, 5-bis(3-methoxyphenoxy)-2-propyl dioxolane (3-3)

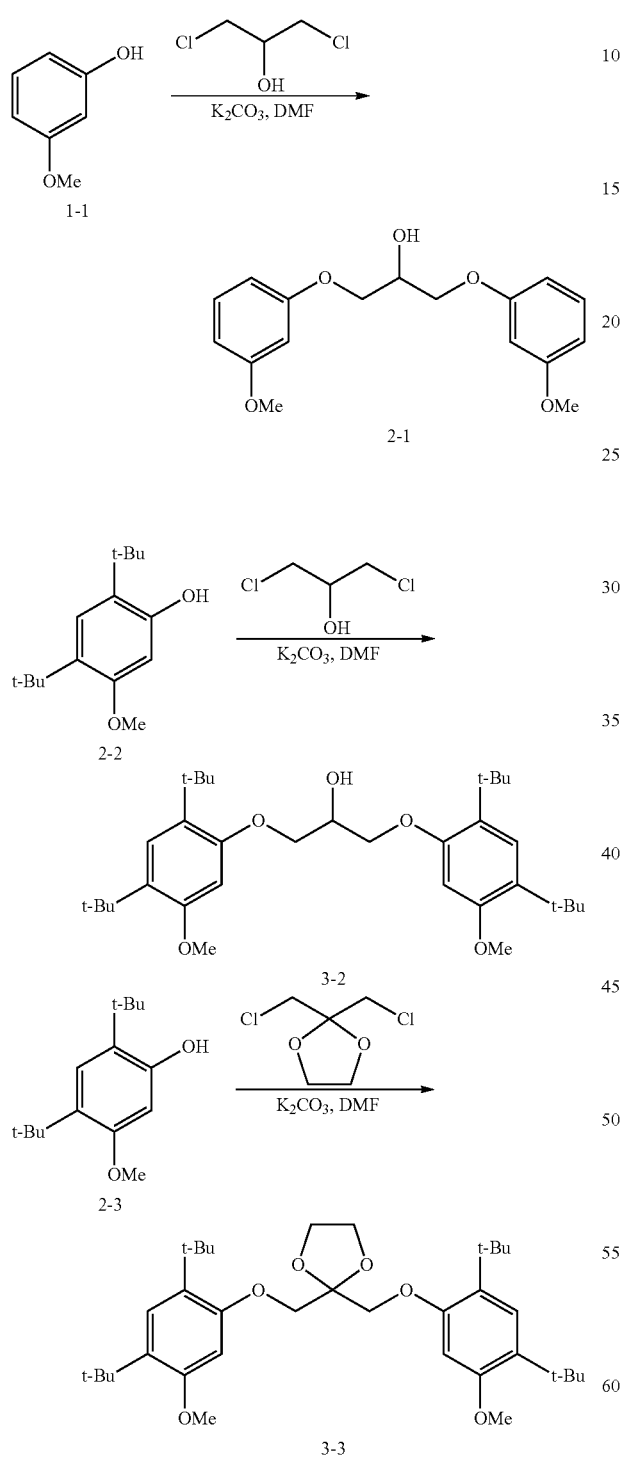

To a 5 L two-necked flask were added 100 g of compound 1-1 (or compound 2-2 or compound 2-3), 1, 3-dichloro-2-propanol (or 2, 2-bis(chloromethyl)-1, 3-dioxolane), potassium carbonate and dimethylformamide. The reaction mixture was reacted at 140° C. for 10 h and filtered to collect a filtrate, which was dried with anhydrous sodium sulfate and evaporated under reduced pressure to obtain 74.8 g of compound 2-1 with a yield of 61% (or 64.9 g of compound 3-2 with 58% yield, or 62.8 g of compound 3-3 with 52% yield).

Compound 2-1: $^1$H NMR (400 MHz, CDCl$_3$): δ=3.54 (d, 1H), 3.78 (s, 6H), 4.04-4.17 (m, 4H), 4.31 (m, 1H), 6.42 (t, 2H), 6.62 (m, 2H), 6.80 (m, 2H), 7.19 (t, 2H).

Compound 3-2: $^1$H NMR (400 MHz, CDCl$_3$): δ=1.37 (d, 36H), 3.28 (d, 1H), 3.81 (s, 6H), 4.03-4.18 (m, 4H), 4.27 (m, 1H), 6.49 (s, 2H), 7.27 (s, 2H).

Compound 3-3: $^1$H NMR (400 MHz, CDCl$_3$): δ=1.38 (d, 36H), 3.84 (s, 6H), 3.92 (s, 4H), 4.41 (s, 4H), 6.43 (s, 2H), 7.25 (s, 2H).

Example 26 Preparation of 1, 5-bis(3-methoxyphenoxy)-acetone (3-1) or 2, 4-di-tert-butyl-1, 5-bis(3-methoxyphenoxy)-acetone (4-2)

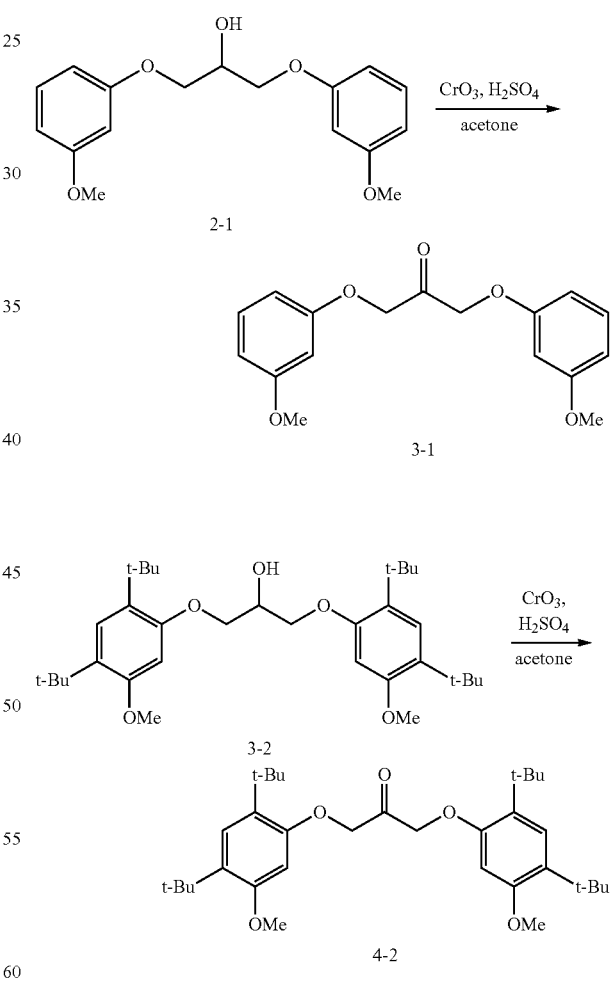

To a 500 mL round-bottomed flask were added 30 g of compound 2-1 or compound 3-2, 9.0 g of chromium trioxide, 7.5 mL of concentrated sulfuric acid and 200 mL of acetone. The reaction mixture was stirred evenly, continuously reacted at room temperature for 6 h and filtered to obtain a filtrate, which was washed with water, dried with anhydrous sodium sulfate and evaporated under reduced pressure to obtain 25.8 g of compound 3-1 with 87% yield or 27.3 g of compound 4-2 with 91% yield.

Compound 3-1: $^1$H NMR (400 MHz, CDCl$_3$): δ=3.78 (s, 6H), 4.97 (s, 4H), 6.50 (t, 2H), 6.70 (m, 2H), 6.80 (m, 2H), 7.20 (t, 2H).

Compound 4-2: $^1$H NMR (400 MHz, CDCl$_3$): δ=1.38 (s, 18H), 1.42 (s, 18H), 3.84 (s, 6H), 4.99 (s, 4H), 6.50 (s, 2H), 7.27 (s, 2H).

Example 27 Preparation of 1, 5-bis(2-bromo-3-methoxyphenoxy)-acetone (4-1)

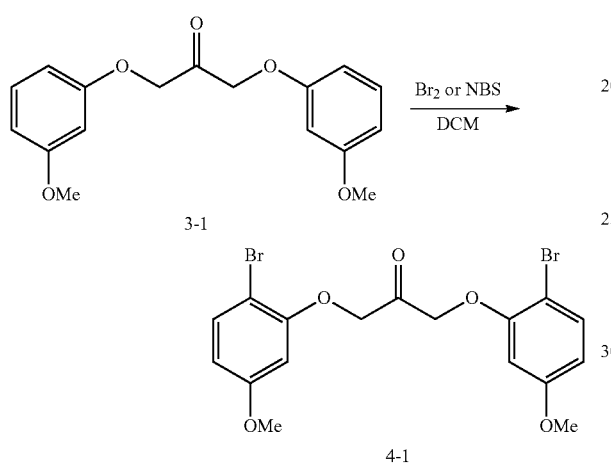

To a 500 mL two-necked flask were sequentially added compound 3-1 (20.0 g, 66.2 mmol) and 200 mL of dichloromethane. The reaction mixture was stirred evenly, dropwise added with a solution of 2.0 mol/L bromine (40 mL, 79.4 mmol) in dichloromethane and reacted under stirring for 4 h. Then the reaction mixture was filtered, and the filtrate was dried with anhydrous sodium sulfate and evaporated under reduced pressure to obtain a crude product, which was separated by column chromatography to obtain 21.9 g of compound 4-1 (72% yield).

$^1$H NMR (400 MHz, CDCl$_3$): δ=3.81 (s, 6H), 5.02 (s, 4H), 6.53 (dd, 2H), 6.77 (d, 2H), 7.52 (d, 2H).

Example 28 Preparation of 4, 4', 6, 6'-tetra-tert-butyl-1, 1'-spirobiindane-7, 7'-diol (5-1) or 4, 4'-dimethoxy-6, 6'-di-tert-butyl-1, 1'-spirobiindane-7, 7'-diol (5-2 or 4-3)

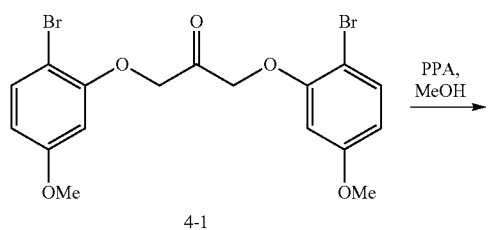

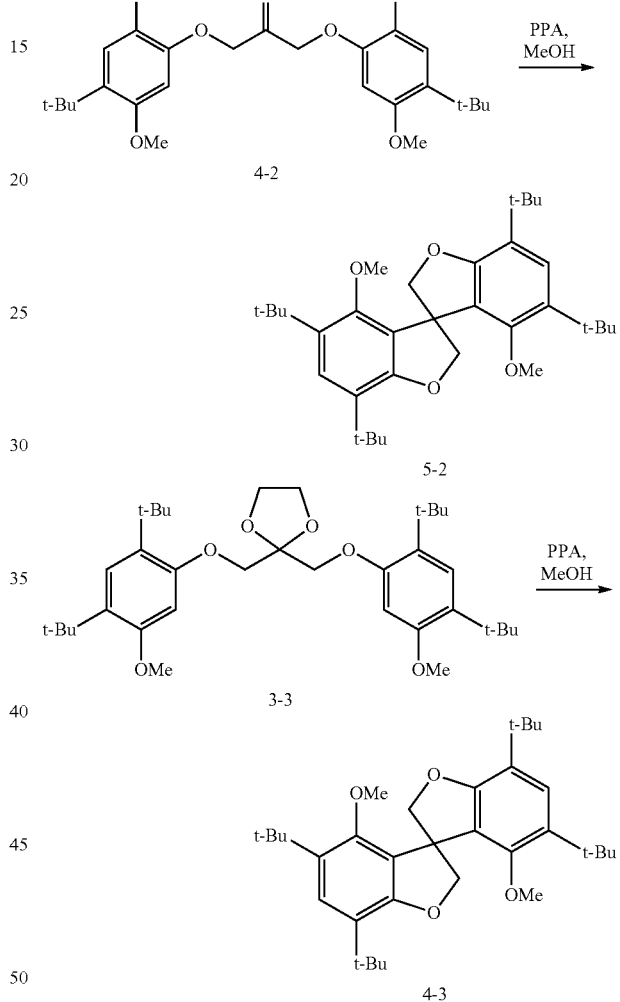

To a 500 mL round-bottomed flask were sequentially added compound 4-1 (20.0 g, 43.5 mmol) (or 20.0 g (38.0 mmol) of compound 4-2, or 20.0 g (35.0 mmol) of compound 3-3), polyphosphoric acid and methanol. The reaction mixture was heated to 60° C. and reacted under stirring for 6 h. After that, the reaction mixture was subjected to washing with water and extraction with ethyl acetate. An organic phase was collected, dried with anhydrous sodium sulfate and evaporated under reduced pressure to obtain a crude product, which was subjected to separation by column chromatography and crystallization with n-hexane to obtain 13.7 g of compound 5-1 (71% yield), 12.6 g of compound 5-2 (65% yield) or 10.1 g of compound 4-3 (57% yield).

Compound 5-1: $^1$H NMR (400 MHz, CDCl$_3$): δ=3.82 (s, 6H), 4.49 (d, 2H), 4.66 (d, 2H), 6.58 (d, 2H), 7.40 (d, 2H).

Compound 5-2 or 4-3: ¹H NMR (400 MHz, CDCl₃): δ=1.39 (s, 18H), 1.42 (s, 18H), 3.77 (s, 6H), 4.46 (d, 2H), 4.61 (d, 2H), 7.28 (s, 2H).

Example 29 Preparation of 7, 7'-dimethoxy-1, 1'-spirodihydrobenzofuran (6-1)

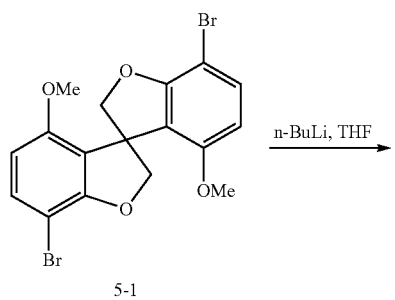

5-1

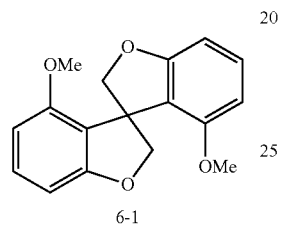

6-1

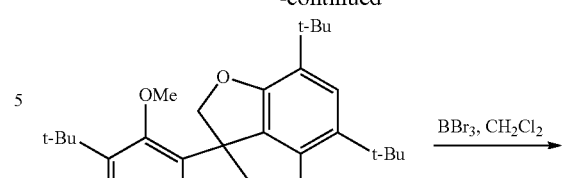

5-2 (or 4-3)

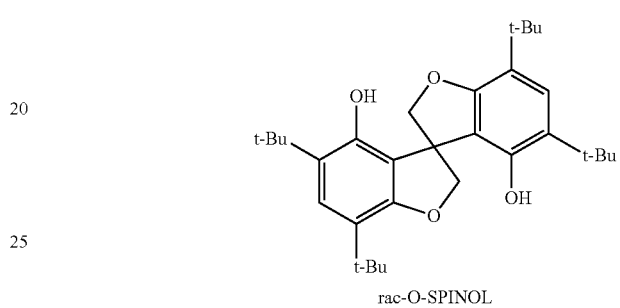

rac-O-SPINOL

To a dry 250 mL Schlenk flask were added compound 5-1 (5.0 g, 11.3 mmol) and 80 mL of tetrahydrofuran, and the atmosphere in the flask was replaced with nitrogen atmosphere. The reaction mixture was cooled to −78° C., dropwise added with 2.5 M n-butyllithium (18.1 mL, 4.0 eq) and reacted for 1 h. After that, the reaction mixture was quenched with 6.0 mL of ethanol, washed with water, and subjected to extraction with dichloromethane. An organic phase was collected, dried with anhydrous sodium sulfate and evaporated under reduced pressure to obtain a crude product, which was crystallized with hexane to obtain 3.1 g of compound 6-1 (95% yield).

¹H NMR (400 MHz, CDCl₃): δ=3.80 (s, 6H), 4.45 (d, 2H), 4.62 (d, 2H), 6.64-6.74 (dd, 4H), 7.07 (t, 2H).

Example 30 Preparation of 1, 1'-spirodihydrobenzofuran-7, 7'-diol (7-1) or 4, 4', 6, 6'-tetra-tert-butyl-1, 1'-spirodihydrobenzofuran-7, 7'-diol (rac-O-SPINOL)

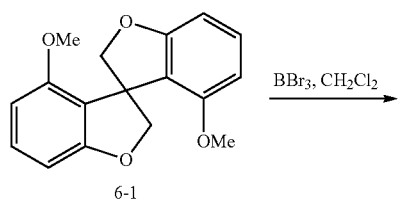

6-1

To a dry 500 mL Schlenk flask were added compound 6-1 (5.0 g, 17.6 mmol) or compound 5-2 (or 4-3) (5.0 g, 9.8 mmol) and 100 mL of dichloromethane, and the atmosphere in the flask was replaced with nitrogen. The reaction mixture was cooled to −78° C., dropwise added with a solution of 2.0 mol/L boron tribromide in dichloromethane, restored to room temperature and reacted overnight. Then the reaction mixture was quenched with water and subjected to extraction with dichloromethane. An organic phase was collected, dried with anhydrous sodium sulfate, evaporated under reduced pressure to obtain a crude product, which was crystallized with hexane to obtain 4.2 g of compound 7-1 (94% yield) or 4.3 g of (rac)-O-SPINOL (6-2 or 5-3) (92% yield).

Compound 7-1: ¹H NMR (400 MHz, DMSO): δ=4.50 (d, 2H), 4.58 (d, 2H), 6.23-6.27 (m, 4H), 6.92 (dd, 2H), 6.78-6.80 (m, 4H), 7.06-7.09 (m, 8H).

(rac)-O-SPINOL (6-2 or 5-3): ¹H NMR (400 MHz, CDCl₃): δ=1.40 (d, 36H), 4.53 (d, 2H), 4.69 (d, 2H), 6.75 (s, 2H), 7.14 (s, 2H).

Example 31 Preparation of 4, 4', 6, 6'-tetra-tert-butyl-1, 1'-spirodihydrobenzofuran-7, 7'-diol (8-1, rac-O-SPINOL)

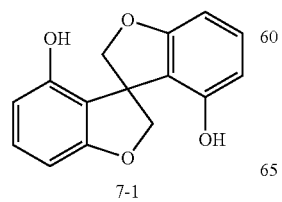

7-1

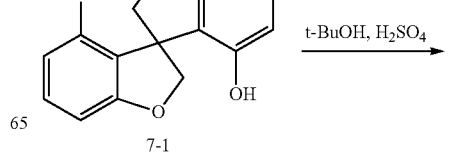

7-1

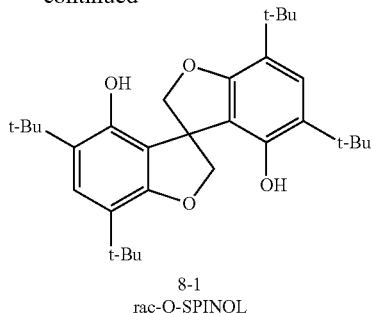

8-1
rac-O-SPINOL

To a 200 mL three-necked flask were added with compound 7-1 (2.0 g, 7.8 mol), tert-butanol (3.7 g, 49.5 mmol) and concentrated sulfuric acid (2.4 g, 24.7 mmol), and the atmosphere in the flask was replaced with nitrogen atmosphere. Then the reaction mixture was heated and reacted under reflux for 24 h. The reaction mixture was subjected to rotary evaporation under reduced pressure, added with 50 mL of water, and subjected to extraction with ethyl acetate. An organic phase was collected, dried with anhydrous sodium sulfate, evaporated under reduced pressure and separated by column chromatography to obtain 3.7 g of compound 8-1 (98% yield).

$^1$H NMR (400 MHz, CDCl$_3$): δ=1.42 (d, 36H), 4.54 (d, 2H), 4.71 (d, 2H), 6.76 (s, 2H), 7.15 (s, 2H).

Example 32 Preparation of 7, 7'-bis[(1, 1'-biphenyl-2, 2'-diyl)phosphite]-4, 4', 6, 6'-tetra-tert-butyl-1, 1'-spirodihydrobenzofuran (9-1-L4)

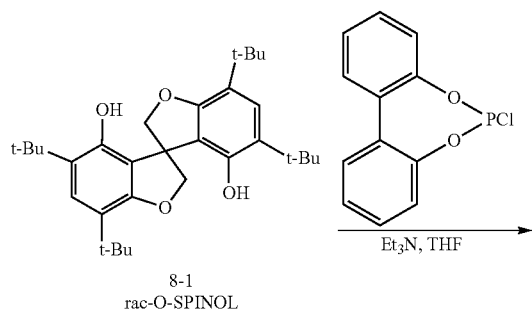

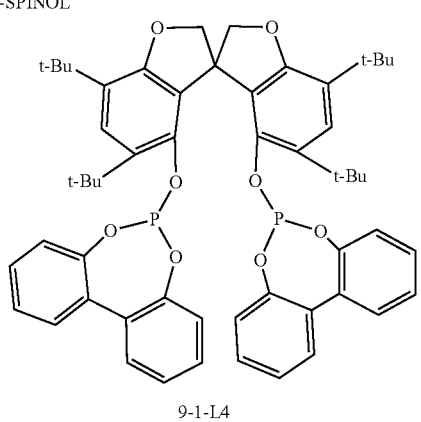

9-1-L4

To a dry 200 mL Schlenk flask were added 2.0 g (4.2 mmol) of rac-O-SPINOL, anhydrous triethylamine (8.8 mL, 63.0 mmol, 15 eq.) and 40 mL of anhydrous tetrahydrofuran under a nitrogen atmosphere. The reaction mixture was cooled to −40° C., dropwise added with 30 mL of a solution of 1,1'-dioxyphosphine chloride (2.6 g, 10.5 mmol, 2.5 equiv.) in anhydrous tetrahydrofuran and reacted at room temperature for 24 h. The reaction mixture was concentrated under nitrogen atmosphere, separated by column chromatography and recrystallized with acetonitrile to obtain 2.9 g of compound 9-1-L4 (75% yield).

Figure 4:
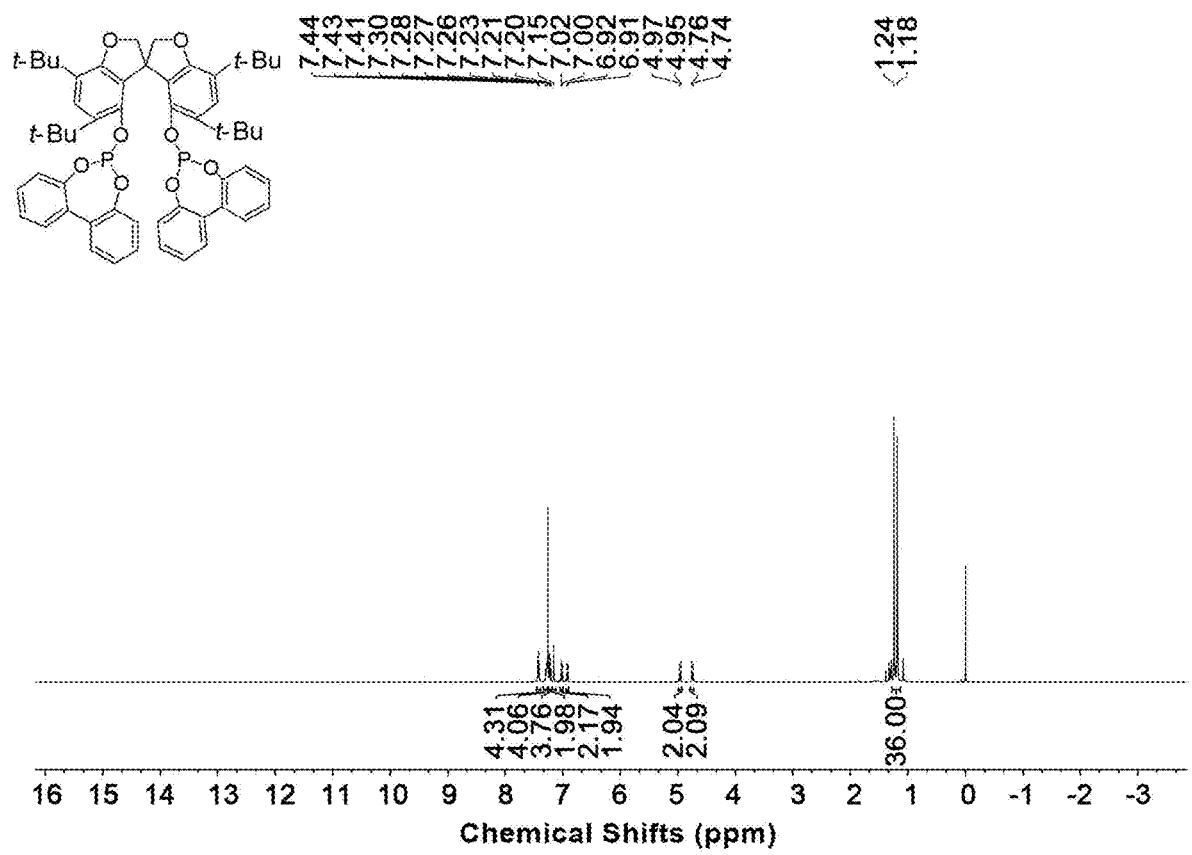
FIG. 4 shows a $^1$H NMR spectrum of 7, 7'-bis[(1, 1'-biphenyl-2, 2'-diyl)phosphite]-4, 4', 6, 6'-tetra-tert-butyl-1, 1'-spirodihydrobenzofuran prepared in Example 32.
Figure 5:
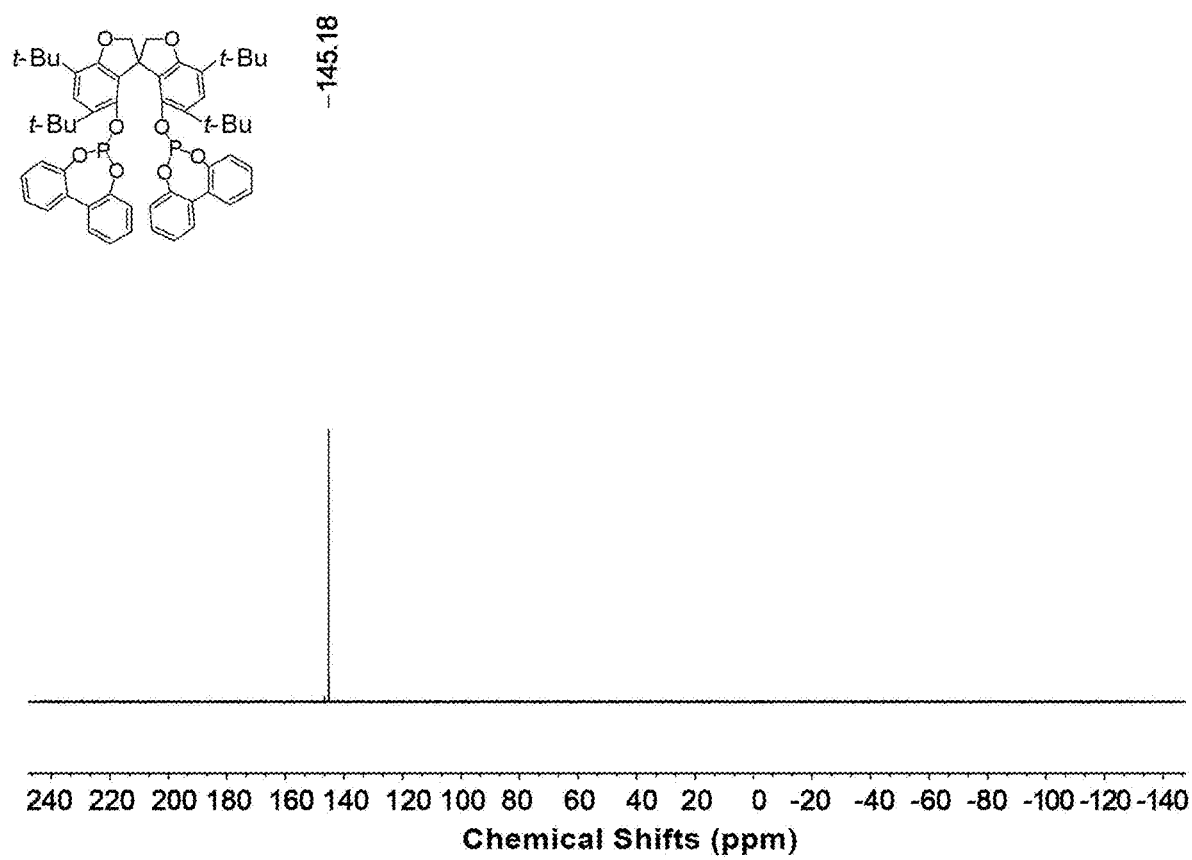
FIG. 5 shows a $^{31}$P NMR spectrum of 7, 7'-bis[(1, 1'-biphenyl-2, 2'-diyl)phosphite]-4, 4', 6, 6'-tetra-tert-butyl-1,1'-spirodihydrobenzofuran prepared in Example 32.

$^1$H NMR (600 MHz, CDCl$_3$): δ=1.18-1.24 (d, 36H), 4.75 (d, 2H), 4.96 (d, 2H), 6.91-7.23 (m, 10H), 7.27-7.30 (m, 4H), 7.41-7.44 (m, 4H) (FIG. 4); and $^{31}$P NMR (243 MHz, CDCl$_3$): δ=145.18 (FIG. 5).

Example 33 Preparation of 1, 1-bis(2, 6-difluorophenyl)-1, 2-ethanediol (3-i)

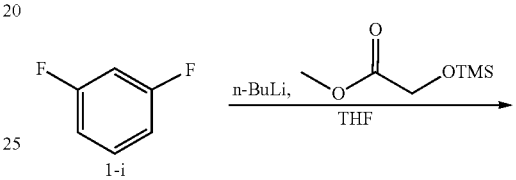

1-i

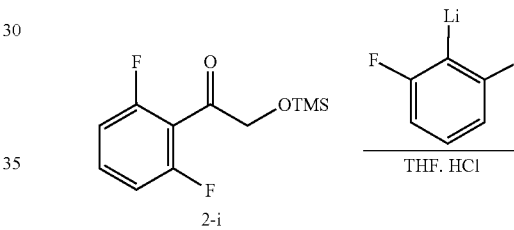

2-i

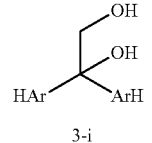

3-i

Ar = 1, 3-difluorobenzene

To a dry 1 L Schlenk flask were added compound 1-i (50.0 g, 437 mmol) and 300 mL of anhydrous tetrahydrofuran, and the atmosphere in the flask was replaced with nitrogen atmosphere. The reaction mixture was cooled to −78° C., dropwise added with a solution of 2.5 M n-butyllithium in hexane (176 mL, 1.005 eq.), stirred at −78° C. for 1 h and slowly added with methyl trimethylsilylglycolate (34.77 g, 214 mmol). The reaction mixture was cooled to +30° C., stirred for 8 h and then restored to room temperature for reaction. After that, the reaction mixture was quenched with dilute hydrochloric acid at +20° C., and subjected to TMS deprotection and extraction with diethyl ether and dichloromethane. Organic phases were combined and evaporated under reduced pressure to obtain 41.9 g of compound 3-i (65% yield).

$^1$H NMR (400 MHz, CDCl$_3$): δ=3.54-3.70 (m, 1H), 4.55 (d, 2H), 4.73 (s, 1H), 6.96 (m, 4H), 7.44 (m, 2H).

Example 34 Preparation of 1, 1-bis(2, 6-difluorophenyl)-acetaldehyde (4-i)

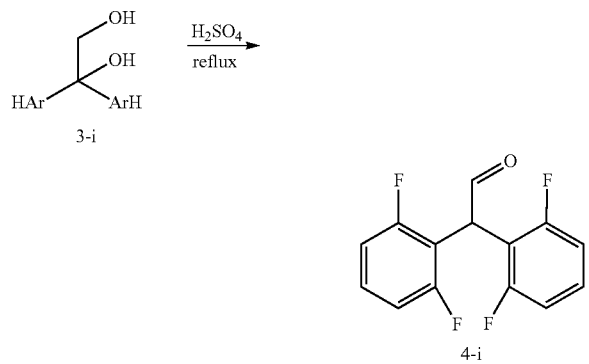

Ar = 1, 3-difluorobenzene

To a 1 L two-necked flask were added compound 3-i (20.0 g, 69.9 mmol) and 110 mL of a 26 wt % sulfuric acid solution. The reaction mixture was reacted under reflux at 100° C. for 4 h, cooled to room temperature and subjected to extraction with dichloromethane. An organic phase was collected, dried with anhydrous sodium sulfate, evaporated under reduced pressure to obtain a crude product, which was subjected to separation by column chromatography to obtain 17.1 g of compound 4-i (92% yield).

$^1$H NMR (400 MHz, CDCl$_3$): δ=5.30 (s, 1H), 6.72-6.85 (m, 4H), 7.12-7.20 (m, 2H), 9.84 (m, 1H).

Example 35 Preparation of 1, 1-bis(2, 6-difluorophenyl)-1, 3-propanediol (6-i)

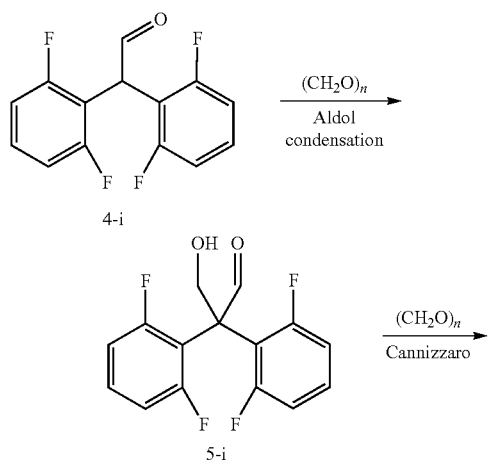

To a 500 mL two-necked flask were added compound 4-i (13.4 g, 50 mmol), lithium hydroxide (24.0 g, 1000 mmol), paraformaldehyde (30.0 g, 1000 mmol) and 120 mL of anhydrous dioxane, and the atmosphere in the flask was replaced with nitrogen atmosphere. The reaction mixture was reacted at 80° C. for 10 h, quenched with dilute hydrochloric acid and subjected to extraction respectively with diethyl ether and dichloromethane. Organic phases were combined and subjected to rotary evaporation under reduced pressure to obtain a crude product, which was subjected to separation by column chromatography to obtain 13.5 g of compound 6-i (90% yield).

$^1$H NMR (400 MHz, CDCl$_3$): δ=2.34 (br, 2H), 4.52 (s, 4H), 6.75-6.79 (m, 4H), 7.10-7.20 (m, 2H).

Example 36 Preparation of 1, 1'-spirodihydrobenzofuran-7, 7'-difluoro (7-i)

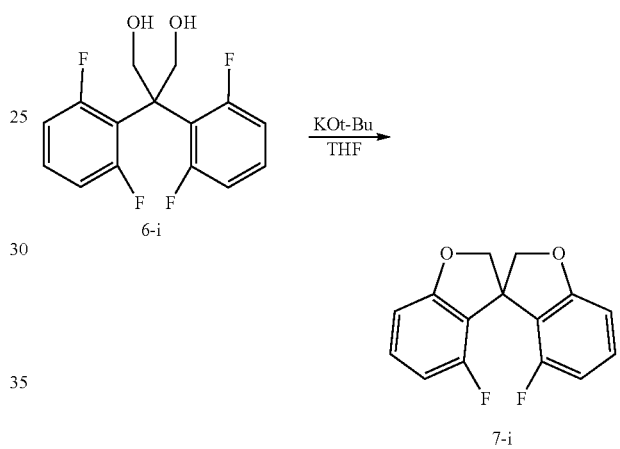

To a 250 mL two-necked flask were added compound 6-i (5.0 g, 16.7 mmol) and potassium tert-butoxide (5.6 g, 50.0 mmol), and the atmosphere in the flask was replaced with nitrogen atmosphere. The reaction mixture was cooled to 0° C., added with 80 mL of anhydrous tetrahydrofuran and then restored to room temperature. The reaction mixture was reacted at 60° C. for 7 h, quenched with dilute hydrochloric acid, and subjected to extraction with dichloromethane. An organic phase was collected, dried with anhydrous sodium sulfate and evaporated under reduced pressure to obtain 4.2 g of compound 7-i (97% yield).

$^1$H NMR (400 MHz, CDCl$_3$): δ=4.64 (d, 2H), 4.79 (d, 2H), 6.57-6.61 (m, 2H), 6.68 (d, 2H), 7.15-7.20 (m, 2H).

Example 37 Preparation of 1, 1'-spirodihydrobenzofuran-7, 7'-dibenzyl ether (8-i)

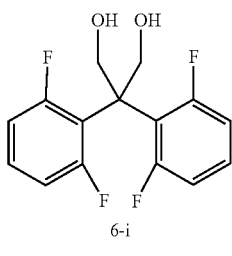

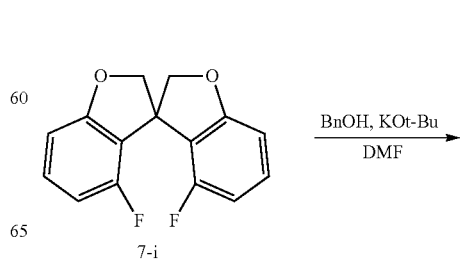

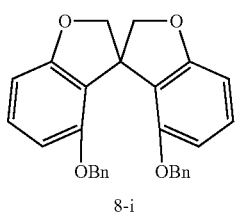

8-i

To a 200 mL two-necked flask were added compound 7-i (4.0 g, 15.4 mmol) and potassium tert-butoxide (10.3 g, 61.5 mmol), and the atmosphere in the flask was replaced with nitrogen atmosphere. The reaction mixture was added with benzyl alcohol (6.6 g, 61.5 mmol) and 100 ml of anhydrous N,N-dimethylformamide and then reacted at 100° C. for 8 h. After reaction, the reaction mixture was cooled to room temperature, added with a large amount of water to precipitate white solid and filtered to obtain 6.6 g of compound 8-i (99% yield).

$^1$H NMR (400 MHz, CDCl$_3$): δ=4.50 (d, 2H), 4.78 (d, 2H), 4.80 (d, 2H), 4.86 (d, 2H), 6.39 (d, 2H), 6.43 (dd, 2H), 6.78-6.80 (m, 4H), 7.06-7.09 (m, 8H).

Example 38 Preparation of 1, 1'-spirodihydrobenzofuran-7, 7'-diol (9-i)

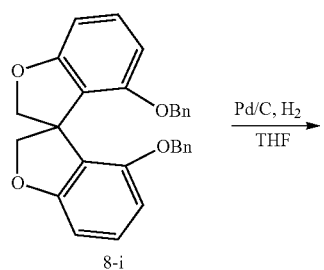

To a 100 mL high pressure reactor were sequentially added compound 8-i (6.0 g, 13.8 mmol), 300 mg of catalyst (10% Pd/C) and 50 mL of tetrahydrofuran. The high pressure reactor was fed with 4 MPa hydrogen to react at room temperature for 20 h. Then, the reaction mixture was subjected to rotary evaporation under reduced pressure to obtain a crude product, which was subjected to separation by column chromatography to obtain 3.5 g of white solid product, that was compound 9-i (99% yield).

$^1$H NMR (400 MHz, DMSO): δ=4.50 (d, 2H), 4.58 (d, 2H), 6.23-6.27 (m, 4H), 6.92 (dd, 2H), 6.78-6.80 (m, 4H), 7.06-7.09 (m, 8H).

Example 39 Preparation of 4, 4', 6, 6'-tetra-tert-butyl-1, 1'-spirodihydrobenzofuran-7, 7'-diol (10-i, rac-O-SPINOL)

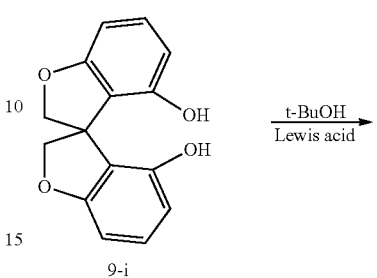

9-i

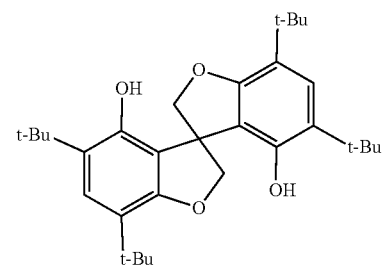

10-i
rac-O-SPINOL
(t-Bu sub)

To a 200 mL three-necked flask were sequentially added compound 9-i (3.0 g, 11.7 mmol), tert-butanol (5.5 g, 74.2 mmol) and concentrated sulfuric acid (3.6 g, 37.1 mmol), and the atmosphere in the flask was replaced with nitrogen atmosphere. Then the reaction mixture was heated and reacted under reflux for reaction for 24 h. The reaction mixture was subjected to rotary evaporation under reduced pressure, added with 50 mL of water, and subjected to extraction with ethyl acetate. An organic phase was collected, dried with anhydrous sodium sulfate, evaporated under reduced pressure and separated by column chromatography to obtain 5.4 g of compound 10-i (96% yield).

$^1$H NMR (400 MHz, CDCl$_3$): δ=1.40 (d, 36H), 4.53 (d, 2H), 4.69 (d, 2H), 6.75 (s, 2H), 7.14 (s, 2H).

Example 40 Splitting of 4, 4', 6, 6'-tetra-tert-butyl-1, 1'-spirodihydrobenzofuran-7, 7'-diol (rac-O-SPINOL)

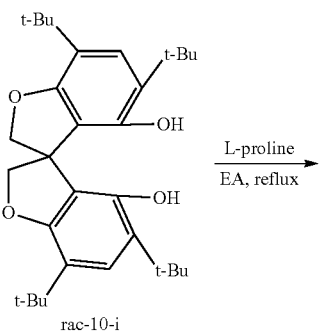

rac-10-i

-continued

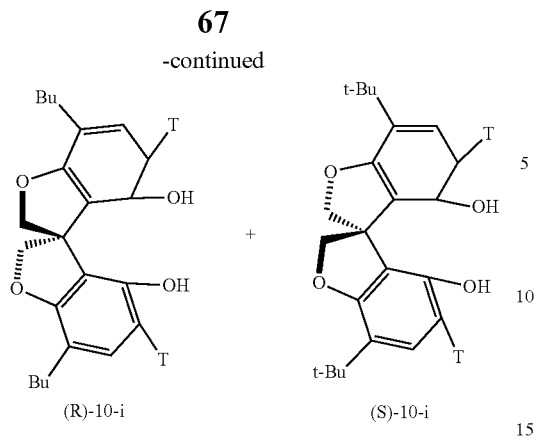

(R)-10-i    (S)-10-i

To a 250 mL round-bottomed flask were sequentially added rac-10-i (12.8 g, 50 mmol), L-proline (2.9 g, 25 mmol) and 100 mL of ethyl acetate. The reaction mixture was stirred at 80° C. for 8 h with precipitation of a white solid. The reaction mixture was cooled to room temperature to collect the white solid. The white solid was subjected to ultrasound for dissolution in a solvent mixture of ethyl acetate and water The reaction mixture was subjected to extraction with ethyl acetate. An organic phase was dried with anhydrous sodium sulfate, evaporated under reduced pressure and subjected to crystallization with ethyl acetate to obtain an optically pure (S)-10-i (>99% ee). Similarly, an optically pure (R)-10-i (>99% ee) was obtain by the same method.

Example 41 Preparation of Asymmetric O-spiro-bisphosphite ligand (12-i-L43)

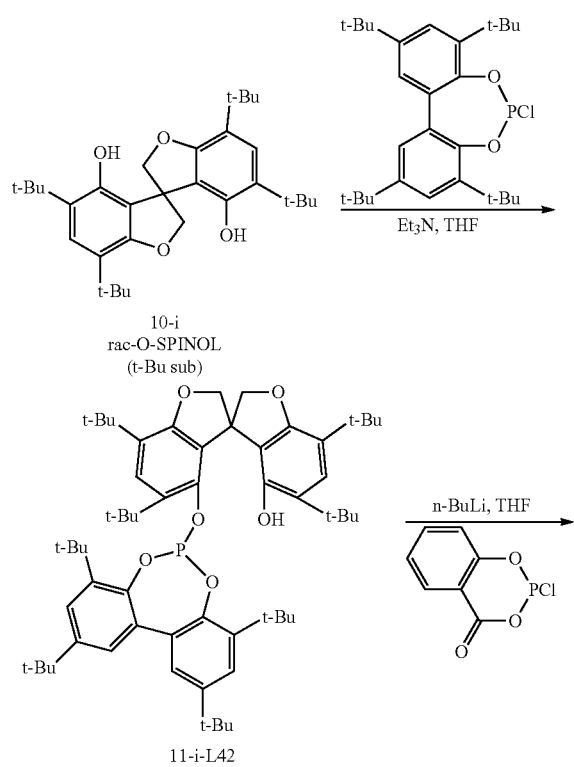

-continued 12-i-L43
asymmetric O-spiro-biphosphite ligand (t-Bu sub)

To a dry 500 mL Schlenk flask were added rac-10-i (4.0 g, 8.3 mmol), anhydrous triethylamine (8.7 mL, 62.4 mmol, 7.5 eq.) and 100 mL of anhydrous tetrahydrofuran under a nitrogen atmosphere. The reaction mixture was cooled to −20° C., dropwise added with 70 mL of a solution of 3,3',5,5'-tetra-tert-butyl-1,1'-biphenyl-2,2'-dioxychlorophosphine (4.7 g, 10.0 mmol, 1.2 equiv.) in anhydrous tetrahydrofuran and reacted at room temperature for 24 h. The reaction mixture was concentrated under a nitrogen atmosphere, separated by column chromatography and crystallized with acetonitrile to obtain 6.3 g of compound 11-i-L42 (82% yield).

To a dry 500 mL Schlenk flask were sequentially added compound 11-i-L42 (6.3 g, 6.9 mmol), 100 mL of anhydrous tetrahydrofuran. The reaction mixture was cooled to −20° C. and dropwise added with 2.5 M n-butyllithium (2.8 mL, 6.9 mmol, 1.0 eq.). The reaction mixture was restored to room temperature and then reacted under reflux for 1 h. After reflux, the reaction mixture was dropwise added to 20 mL of a solution of 2-chloro-1,3,2-benzodioxaphosphinan-4-one (1.68 g, 8.3 mmol, 1.2 equiv.) in anhydrous tetrahydrofuran at −40° C. and then reacted at room temperature for 24 h. The reaction mixture was concentrated under a nitrogen atmosphere and separated by column chromatography to obtain 3.8 g of compound 12-i-L43 (51% yield).

$^1$H NMR (600 MHz, CDCl$_3$): δ=1.34-1.38 (m, 36H), 1.45-1.46 (m, 36H), 4.45-4.75 (m, 4H), 7.03-7.47 (m, 9H), 7.93 (dd, 1H); and $^{31}$P NMR (243 MHz, CDCl$_3$): δ=123.41, 140.36.

Example 42 Preparation of (R,R)-7, 7'-bis[(1, 1'-biphenyl-2, 2'-diyl)phosphite]-4, 4', 6, 6'-tetra-tert-butyl-(R)-1, 1'-spirodihydrobenzofuran ((R,R,R)-11-i-L17)

Example 43 Preparation of 2, 2'-bis[(dipyrrolylphosphino)oxo]-4, 4', 6, 6'-tetra-tert-butyl-1, 1'-spirodihydrobenzofuran (O-L32)

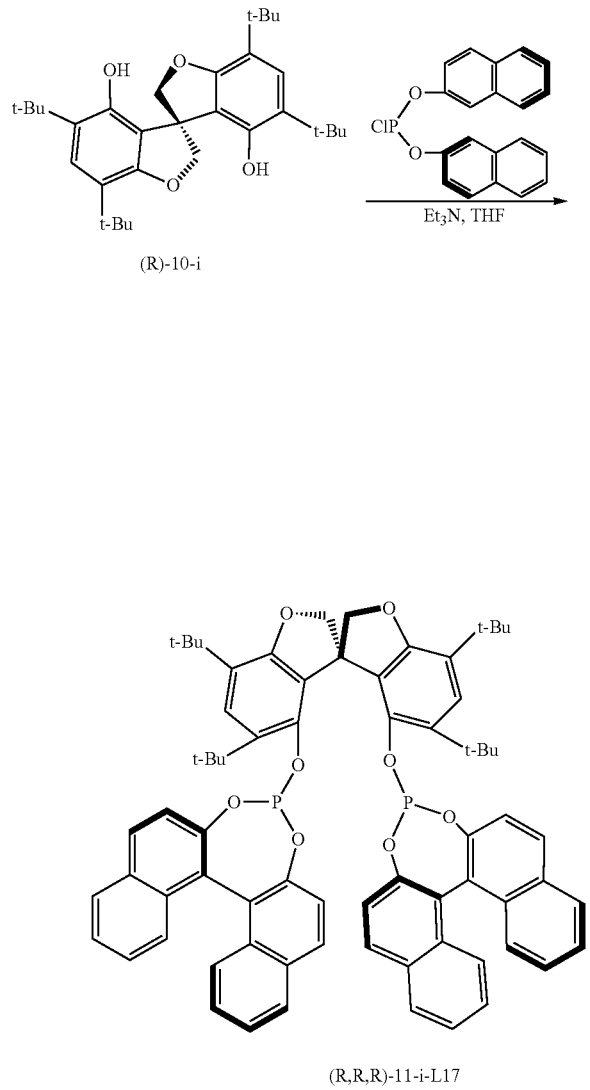

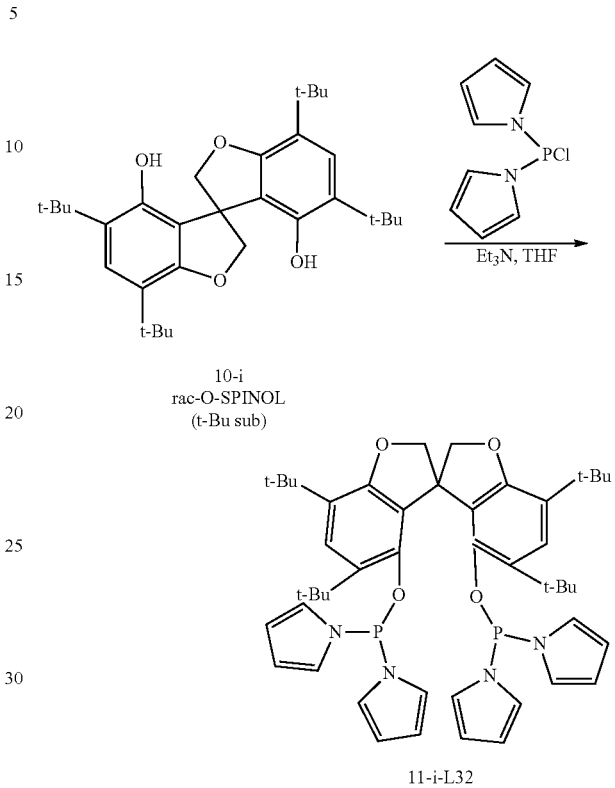

To a dry 500 mL Schlenk flask were sequentially added (R)-10-i (4.0 g, 8.3 mmol), anhydrous triethylamine (17.3 mL, 124.8 mmol, 15.0 eq.) and 100 mL of anhydrous tetrahydrofuran under a nitrogen atmosphere. The reaction mixture was cooled to −40° C., dropwise added with 100 mL of a solution of (R)-(1,1'-binaphthyl-2,2'-dioxy)chlorophosphine (7.6 g, 21.6 mmol, 2.6 equiv.) in anhydrous tetrahydrofuran and then reacted at room temperature for 24 h. The reaction mixture was concentrated under a nitrogen atmosphere, separated by column chromatography and recrystallized with acetonitrile to obtain 9.2 g of compound (R,R,R)-11-i-L17 (92% yield).

$^1$H NMR (600 MHz, CDCl$_3$): δ=1.37-1.45 (d, 36H), 4.52-4.66 (dd, 4H), 7.05 (s, 2H), 7.30-7.43 (m, 16H), 7.87-7.94 (m, 8H); and $^{31}$P NMR (243 MHz, CDCl$_3$): δ=143.08.

To a dry 500 mL Schlenk flask were sequentially added rac-10-i (4.0 g, 8.3 mmol), anhydrous triethylamine (17.3 mL, 124.8 mmol, 15.0 eq.) and 100 mL of anhydrous tetrahydrofuran under a nitrogen atmosphere. The reaction mixture was cooled to −30° C., dropwise added with 50 mL of a solution of 1,1'-(chlorophosphoranediyl)bis(1H-pyrrole) (4.0 g, 19.9 mmol, 2.4 equiv.) in anhydrous tetrahydrofuran and then reacted at room temperature for 24 h. The reaction mixture was concentrated under a nitrogen atmosphere, separated by column chromatography and recrystallized with acetonitrile to obtain 5.1 g of compound 11-i-L32 (77% yield).

$^1$H NMR (600 MHz, CDCl$_3$): δ=1.45 (d, 36H), 4.45-4.73 (dd, 4H), 6.25 (t, 8H), 6.91 (t, 8H), 7.21 (s, 2H); $^{31}$P NMR (243 MHz, CDCl$_3$): δ=125.93.

It should be noted that other O-spiro-bisphosphorous ligands among L1-L41 of formula (III) can be prepared by using the corresponding chlorophosphite or phosphoramidite derivative.

A batch reactor (shown in FIG. 1) was employed to simulate the industrial hydroformylation of mixed/etherified C4 to test the spiro-bisphosphite ligands and the O-spiro-bisphosphite ligands obtained above, where two kinds of C4 materials were used, respectively etherified C4 and MTO C4. The etherified C4 consisted of isobutane (52.1 w/w %), 1-butene (16.6 w/w %), cis-2-butene (15.3 w/w %) and trans-2-butene (16.0 w/w %), and the MTO C4 consisted of n-butane (6.0 w/w %), 1-butene (0.7 w/w %), cis-2-butene (34.7 w/w %) and trans-2-butene (58.6 w/w %).

In order to ensure the ligand activity and protect aldehyde products from being oxidized, the above-mentioned materials were preprocessed to remove water, oxygen, sulfur-contain substances (sulfide), chlorine-containing substances (halide) and nitrogen-containing compounds (e.g., HCN), as well as those inhibiting the rhodium catalysts, such as carboxylic acids, butadiene, propadiene, and alkynes. In order to evaluate the catalytic reactivity of these novel sterically-hindered O-spiro-bisphosphorous ligands in the hydroformylation of etherified C4/MTO C4, other commercially-available and previously-reported ligands were tested under nearly identical reaction conditions for comparison. Ligands 1-15 used below were structurally expressed as follows:

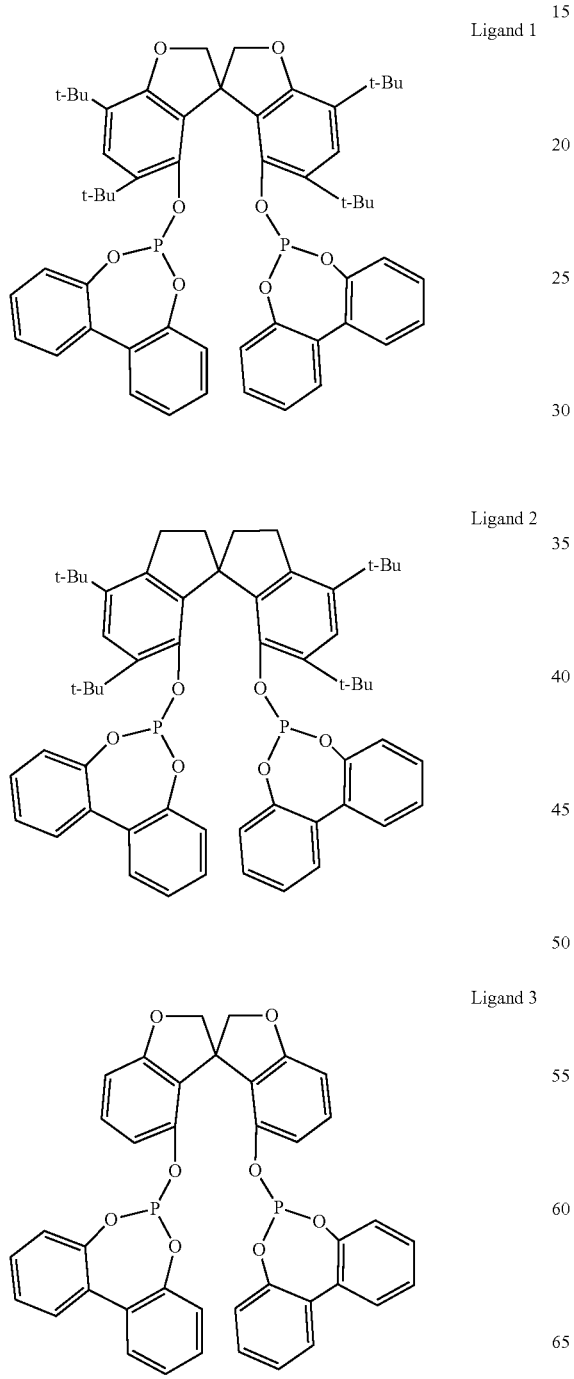

Ligand 1

Ligand 2

Ligand 3

-continued

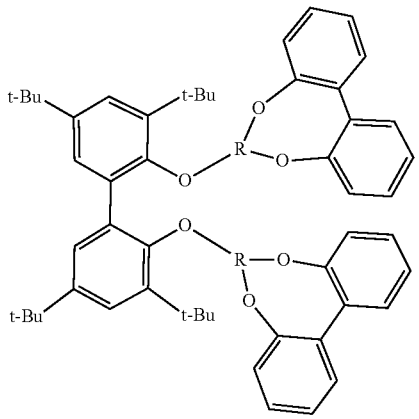

Ligand 4

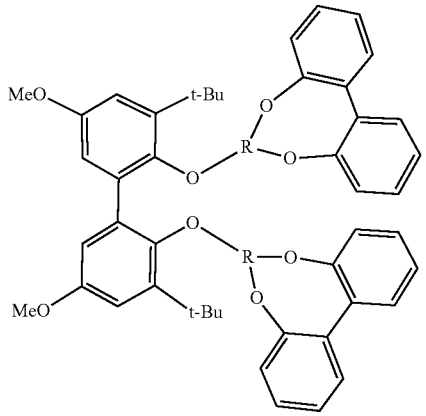

Ligand 5

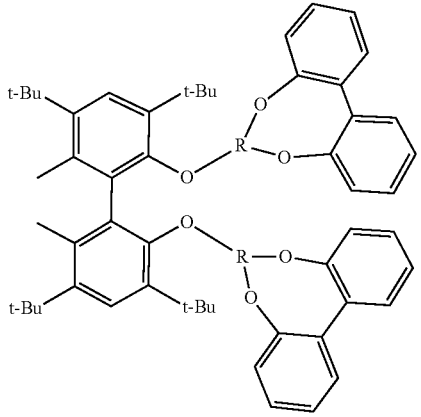

Ligand 6

Ligand 7
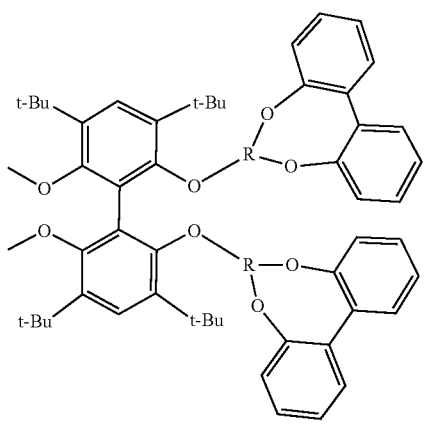
Ligand 8
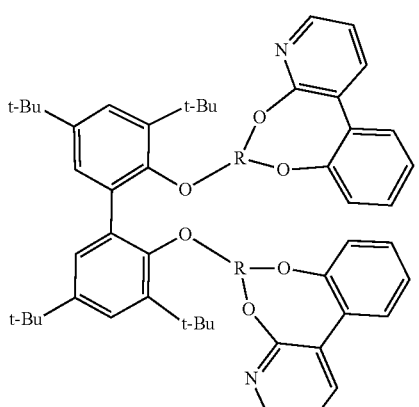
Ligand 9
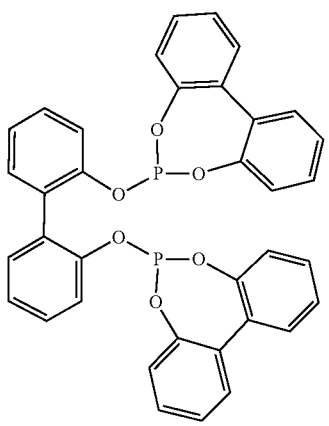
Ligand 10
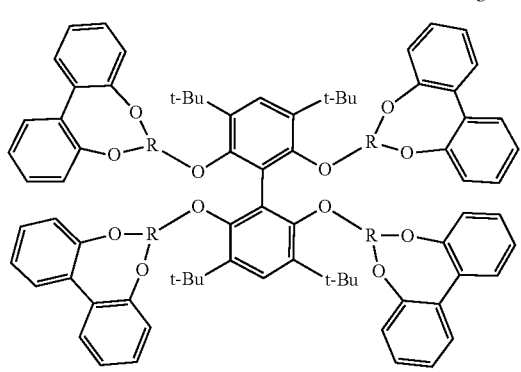
Ligand 11
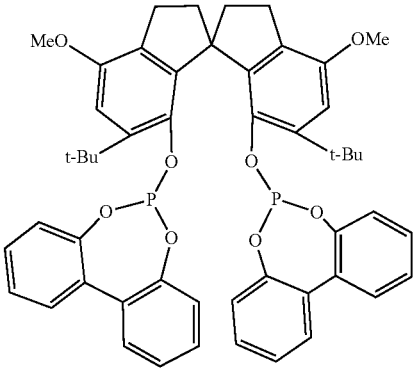
Ligand 12
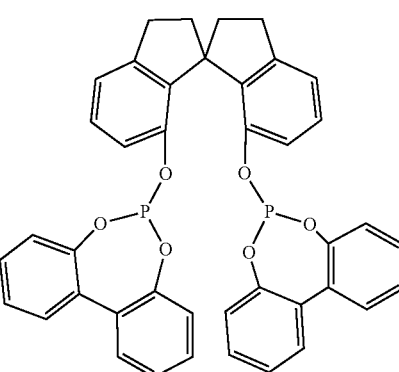
Ligand 13
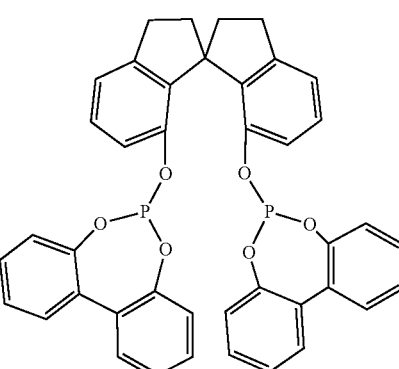
Ligand 14
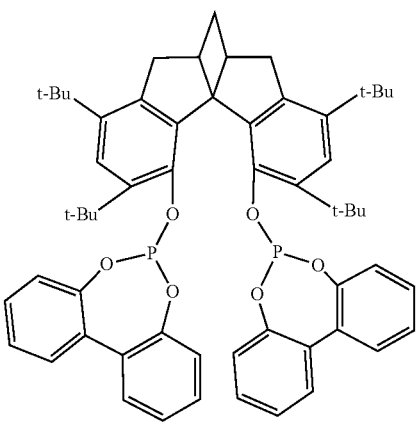

Ligand 15

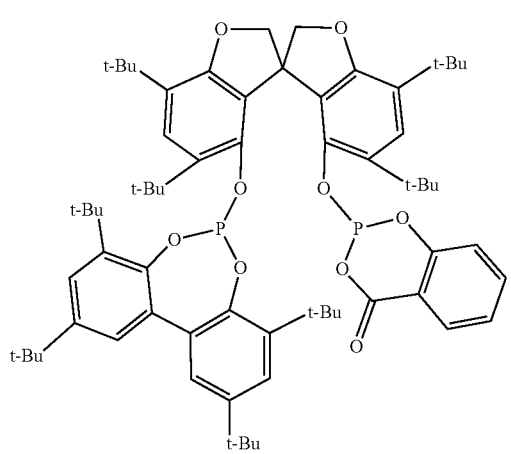

Comparative Example 1

The above-mentioned spiro-bisphosphorous compounds and O-spiro-bisphosphorous compounds were used as ligands of the transition metal to catalyze the hydroformylation of olefins. Specifically, to a 200 mL stainless-steel high-pressure reactor equipped with a pressure sensor, a temperature probe, a sampling port and a safety relief valve were added Rh(acac)(CO)$_2$ (0.01 mmol, 2.6 mg), Ligands 1-15 (0.03-0.04 mmol), toluene and n-decane (internal standard) under an argon atmosphere. The reaction mixture was magnetically stirred for 30 min to produce a rhodium-ligand catalytic complex. Subsequently, a N$_2$ or Ar gas pipeline is connected to purge the reactor thoroughly. Under the switching of a two-position four-way valve, a certain proportion of liquified etherified C4 was introduced by means of a metering syringe pump such that a concentration of the rhodium catalyst was controlled at around 159 ppm. The reaction mixture was stirred uniformly at room temperature for 5-10 min. After that, the reactor was charged with a syngas (CO/H$_2$=1:1) to a total pressure of 1.0 MPa and heated to 70° C. by an electric heating jacket. The reaction mixture was reacted under a constant total pressure of 1.0 MPa for 2-4 h, and cooled to room temperature by a −40° C. electric cooling jacket. Then the reaction mixture was sampled through the sampling port without opening the high-pressure reactor, diluted with HPLC-grade ethyl acetate and analyzed by gas chromatograph (GC) for the l/b ratio (a ratio of n-pentanal/2-methylbutyraldehyde). The remaining pressure in the reactor was carefully released in a fume hood. The reaction mixture was sampled and weighed. The analysis results were shown in Table 1.

TABLE 1

Reaction parameters and summarized results

| Entry | Ligand | L/Rh | T [° C.] | Time [h] | Conv. [%] | l/b [%] | Linearity [%] | TOF [h$^{-1}$] |
|---|---|---|---|---|---|---|---|---|
| 1 | Ligand 1 | 4 | 70 | 3 | 96.0 | 99.0 | 99.0 | 1280 |
| 2 | Ligand 2 | 4 | 70 | 4 | 94.2 | 54.6 | 98.2 | 942 |
| 3 | Ligand 3 | 4 | 70 | 4 | 75.4 | 24.0 | 96.0 | 754 |
| 4 | Ligand 4 | 4 | 70 | 4 | 81.2 | 26.0 | 96.3 | 812 |
| 5 | Ligand 5 | 4 | 70 | 4 | 71.1 | 33.5 | 97.1 | 711 |
| 6 | Ligand 6 | 4 | 70 | 4 | 93.3 | 5.4 | 84.4 | 933 |
| 7 | Ligand 7 | 4 | 70 | 4 | 92.7 | 2.2 | 68.9 | 927 |
| 8 | Ligand 8 | 4 | 70 | 4 | 80.7 | 24.0 | 96.0 | 807 |
| 9 | Ligand 9 | 4 | 70 | 4 | 67.5 | 12.3 | 92.5 | 675 |
| 10 | Ligand 10 | 3 | 70 | 2 | 96.5 | 22.3 | 95.7 | 1930 |
| 11 | Ligand 11 | 4 | 70 | 4 | 75.6 | 75.9 | 98.7 | 756 |
| 12 | Ligand 12 | 4 | 70 | 4 | 67.5 | 20.7 | 95.4 | 675 |
| 13 | Ligand 13 | 4 | 70 | 2.5 | 97.3 | 82.3 | 98.8 | 1557 |
| 14 | Ligand 14 | 4 | 70 | 4 | 91.8 | 60.4 | 98.4 | 918 |
| 15 | Ligand 15 | 4 | 70 | 3 | 95.6 | 76.6 | 98.7 | 1275 |

Comparative Example 2

The above-mentioned spiro-bisphosphorous compounds and O-spiro-bisphosphorous compounds were used as ligands of the transition metal to catalyze the hydroformylation of olefins. Specifically, to a 200 mL stainless-steel high-pressure reactor equipped with a pressure sensor, a temperature probe, a sampling port and a safety relief valve were added Rh(acac)(CO)$_2$ (0.01 mmol, 2.6 mg), Ligands 1-15 (0.03-0.04 mmol), toluene and n-decane (internal standard) under an argon atmosphere. The reaction mixture was magnetically stirred for 30 min to produce a rhodium-ligand catalytic complex. Subsequently, a N$_2$ or Ar gas pipeline is connected to purge the reactor thoroughly. Under the switching of a two-position four-way valve, a certain proportion of liquified MTO C4 was introduced by means of a metering syringe pump such that a concentration of the rhodium catalyst was controlled at around 159 ppm. The reaction mixture was stirred uniformly at room temperature for 5-10 min. After that, the reactor was charged with a syngas (CO/H$_2$=1:1) to a total pressure of 1.0 MPa and heated to 70° C. by an electric heating jacket. The reaction mixture was reacted under a constant total pressure of 1.0 MPa for 2-4 h, and cooled to room temperature by a −40° C. electric cooling jacket. Then the reaction mixture was sampled through the sampling port without opening the high-pressure reactor, diluted with HPLC-grade ethyl acetate and analyzed by gas chromatograph (GC) for the l/b ratio (a ratio of n-pentanal/2-methylbutyraldehyde). The remaining pressure in the reactor was carefully released in a fume hood. The reaction mixture was sampled and weighed. The analysis results were shown in Table 2.

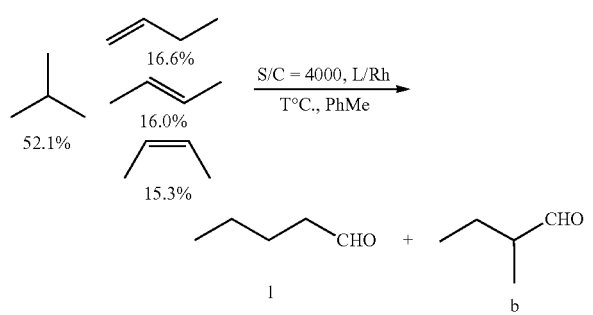

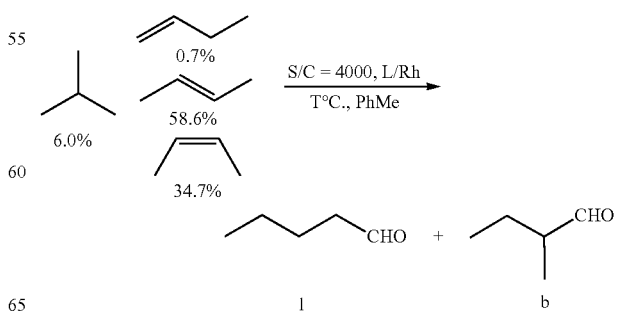

TABLE 2

Summarized results

| Entry | Ligand | L/Rh | T [°C.] | Time [h] | Conv. [%] | l/b [%] | Linearity [%] | TOF [h⁻¹] |
|---|---|---|---|---|---|---|---|---|
| 1 | Ligand 1 | 4 | 70 | 3 | 93.0 | 40.7 | 97.6 | 1240 |
| 2 | Ligand 2 | 4 | 70 | 4 | 91.0 | 37.5 | 97.4 | 910 |
| 3 | Ligand 3 | 4 | 70 | 4 | 70.2 | 18.2 | 94.8 | 702 |
| 4 | Ligand 4 | 4 | 70 | 4 | 75.7 | 21.2 | 95.5 | 757 |
| 5 | Ligand 5 | 4 | 70 | 4 | 66.8 | 25.3 | 96.2 | 668 |
| 6 | Ligand 6 | 4 | 70 | 4 | 89.4 | 4.1 | 80.7 | 894 |
| 7 | Ligand 7 | 4 | 70 | 4 | 86.2 | 1.0 | 49.6 | 862 |
| 8 | Ligand 8 | 4 | 70 | 4 | 74.9 | 22.8 | 95.8 | 749 |
| 9 | Ligand 9 | 4 | 70 | 4 | 57.3 | 6.8 | 87.1 | 573 |
| 10 | Ligand 10 | 3 | 70 | 2 | 92.6 | 21.7 | 95.6 | 1852 |
| 11 | Ligand 11 | 4 | 70 | 4 | 72.5 | 49.0 | 98.0 | 725 |
| 12 | Ligand 12 | 4 | 70 | 4 | 61.5 | 16.5 | 94.3 | 615 |
| 13 | Ligand 13 | 4 | 70 | 3 | 94.6 | 38.6 | 97.5 | 1261 |
| 14 | Ligand 14 | 4 | 70 | 4 | 87.1 | 34.4 | 97.2 | 871 |
| 15 | Ligand 15 | 4 | 70 | 3 | 89.2 | 42.0 | 97.7 | 1189 |

Mentioned above are merely preferred embodiments of this disclosure, which are not intended to limit the scope of the present disclosure. It should be understood that any changes, modifications, replacements and improvements made by those skilled in the art without departing from the spirit and scope of this disclosure should fall within the scope of the present disclosure defined by the appended claims.

What is claimed is:

1. A spiro-bisphosphorous compound of formula (I), formula (II) or formula (III)

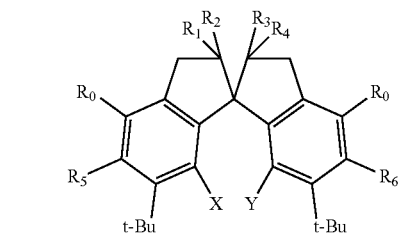
(I)

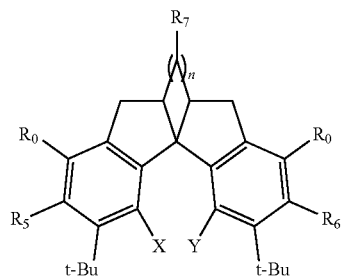
(II)

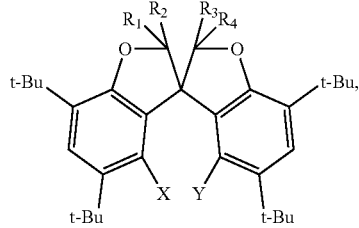
(III)

X = OH, OPR₉, PR₉, CH₂PR₉, NR₉
Y = OH, OPR₉, PR₉, CH₂PR₉, NR₉ wherein:

$R_0$ is methoxy or tert-butyl; $R_1$, $R_2$, $R_3$ and $R_4$ are independently selected from the group consisting of $C_1$-$C_{10}$ alkyl, alkoxy, aryl, aryloxy and hydrogen; and $R_5$, $R_6$ and $R_7$ are independently selected from the group consisting of $C_1$-$C_{10}$ alkyl, alkoxy, aryl, aryloxy and hydrogen; n is $C_1$-$C_{10}$ alkylene; and $PR_9$ is a chlorophosphite structure comprising an aryl group selected from the group consisting of a biphenyl, methylene diphenyl, binaphthyl, benzoyloxy, O-phenyl, phenyl, and naphthyl group; or a chlorophosphoramidite structure comprising pyrrolyl, imidazolyl, carbazolyl or pyridyl.

2. The spiro-bisphosphorous compound of claim 1, wherein the spiro-bisphosphorous compound is shown in formula (I-1):

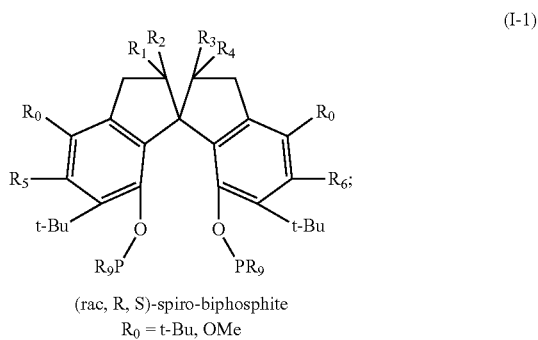
(I-1)

(rac, R, S)-spiro-biphosphite
$R_0$ = t-Bu, OMe or formula (II-1):

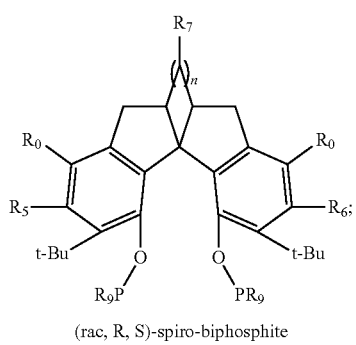
(II-1)

(rac, R, S)-spiro-biphosphite
$R_0$ = t-Bu, OMe wherein the PR₉ is selected from the group consisting of:

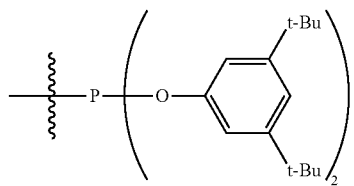
L1

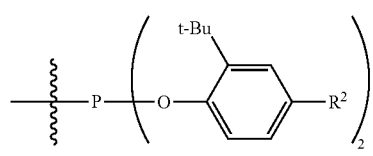
R² = t-Bu, H, Me, OMe, CF₃, Cl
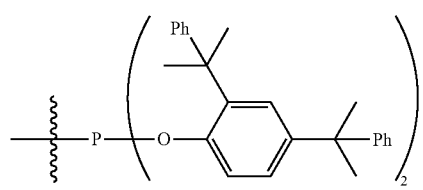
L4
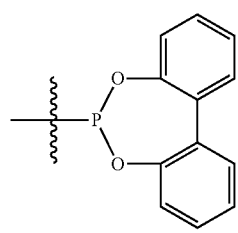
L5
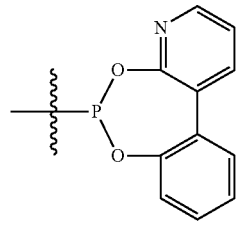
L6
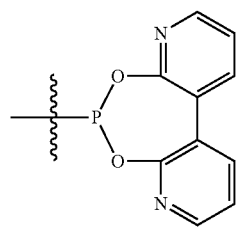
L7
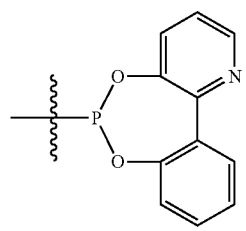
L8
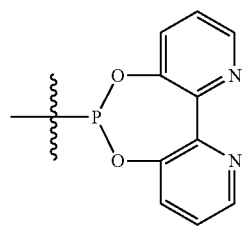
L9
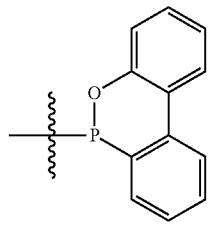
L10
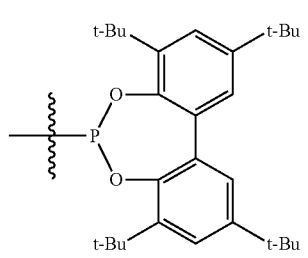
L11
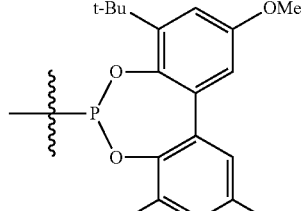
(R)-L12
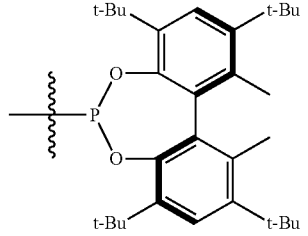
(S)-L12
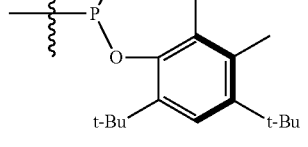
(R)-L13
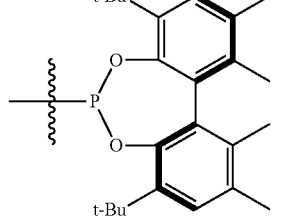

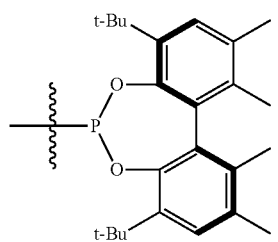
(S)-L13
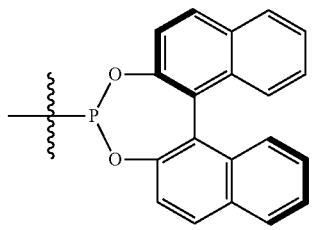
(S)-L17
L14
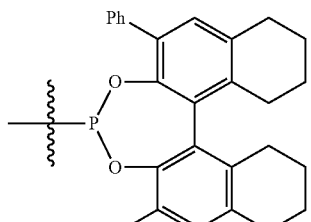
L18
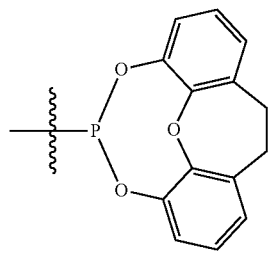
L15
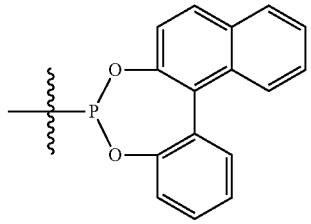
L19
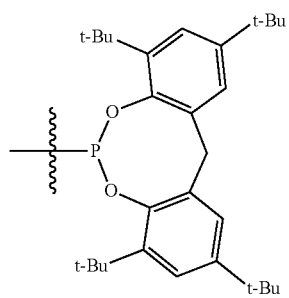
L16
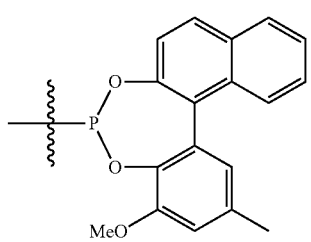
L20
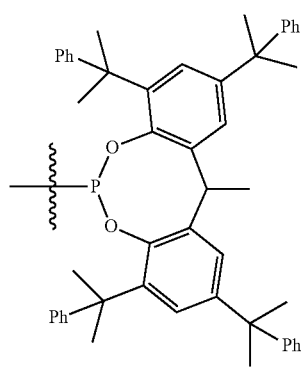
L17
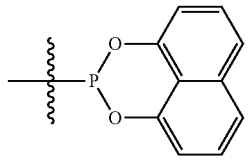
L21
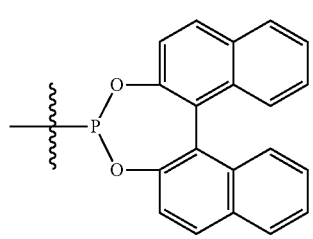
L22
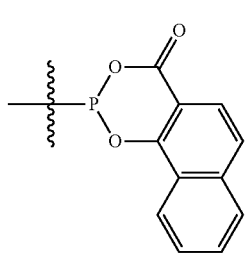
L23
(R)-L17
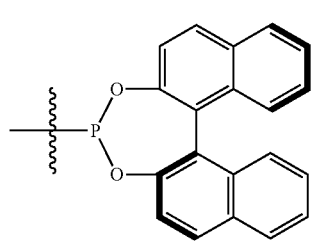

-continued
L24
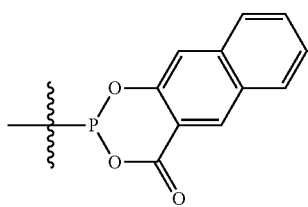
L25
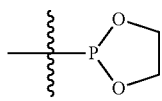
L26
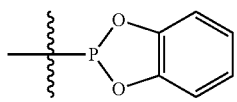
L27
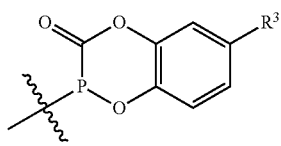
R³ = H, NO₂, Cl
L28
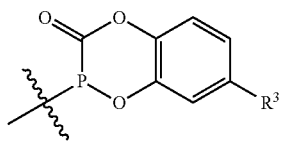
R³ = OMe, Cl
L29
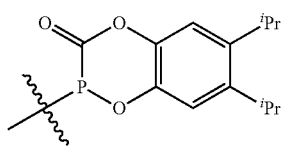
L30
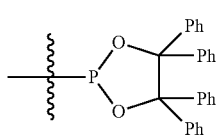
L31
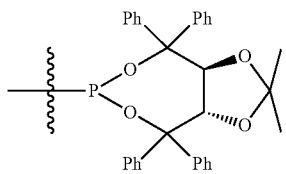
(R)-L31
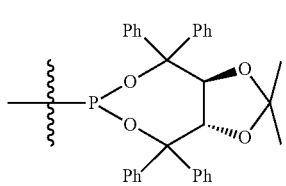
-continued
(S)-L31
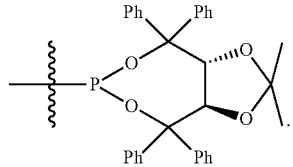
3. The spiro-bisphosphorous compound of claim 1, wherein the spiro-bisphosphorous compound is shown in formula (III-1):
(III-1)
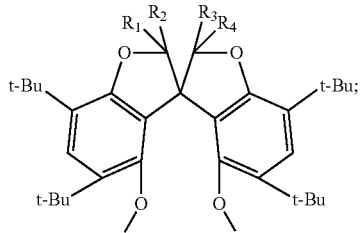
(rac, R, S)-O-spiro-biphosphite/
biphosphoramidite
(t-Bu sub)
wherein the PR₉ is selected from the group consisting of:
L1
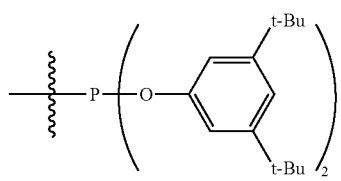
L2
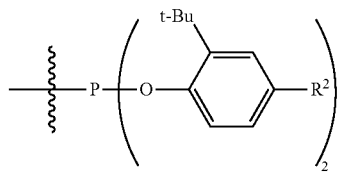
R² = t-Bu, H, Me, OMe, CF₃, Cl
L3
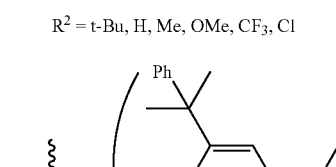
L4
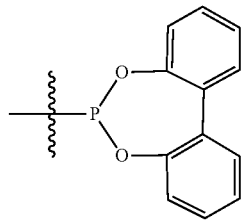

-continued
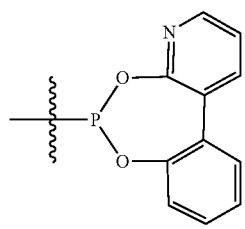
L5
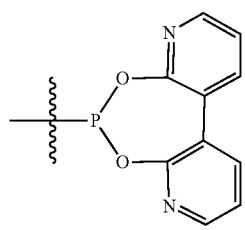
L6
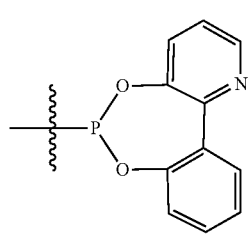
L7
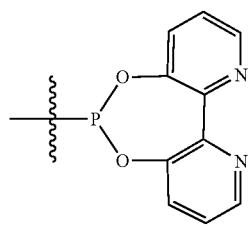
L8
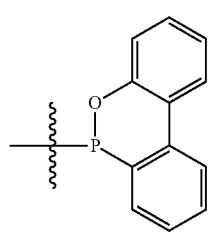
L9
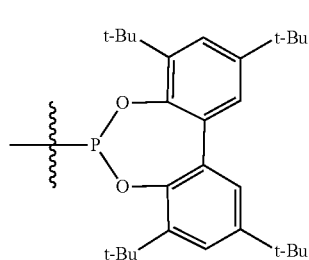
L10
-continued
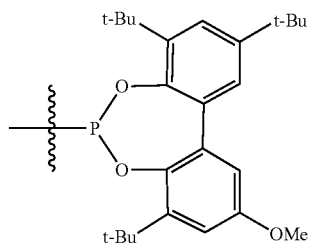
L11
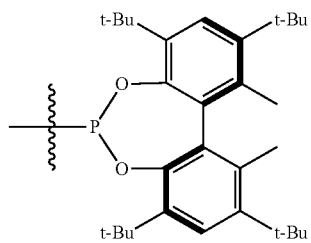
(R)-L12
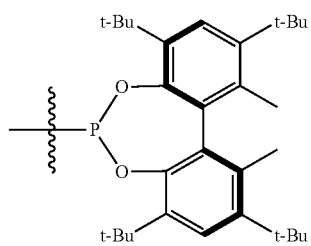
(S)-L12
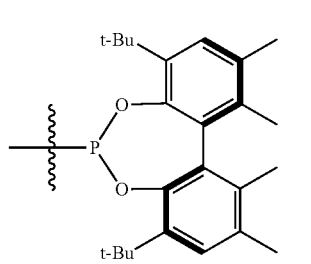
(R)-L13
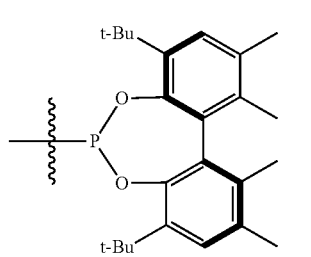
(S)-L13
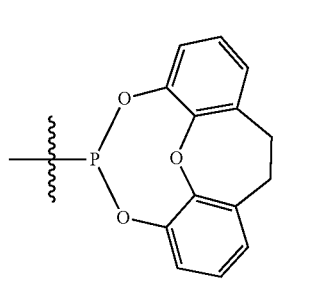
L14

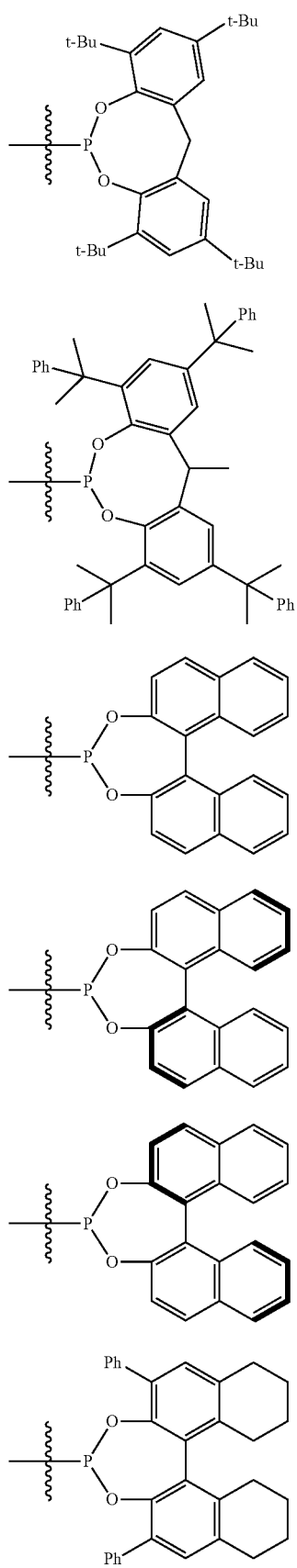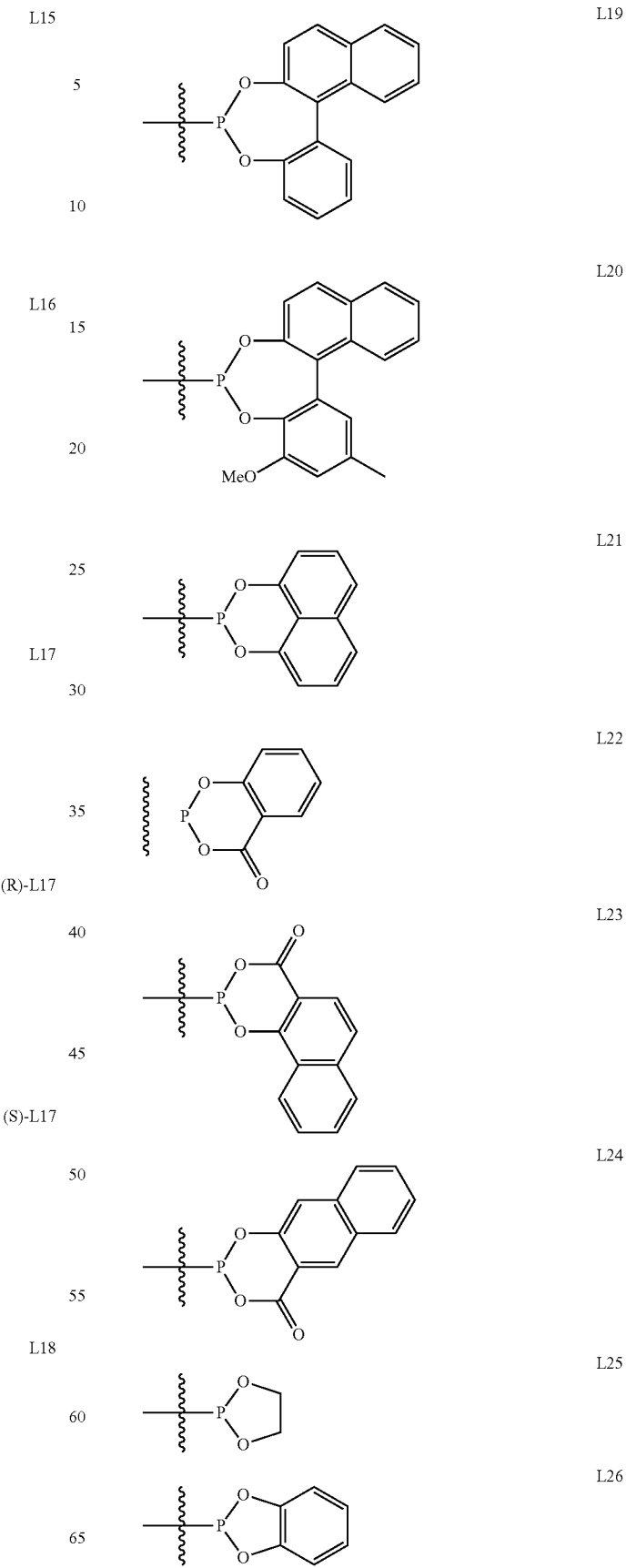

-continued
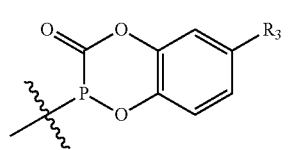
R³ = H, NO₂, Cl
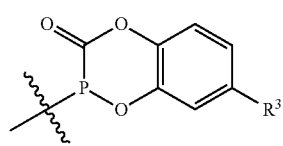
R³ = OMe, Cl
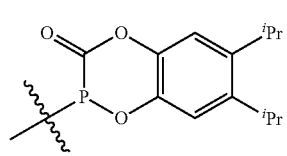
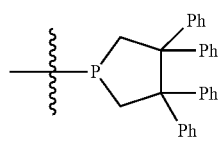
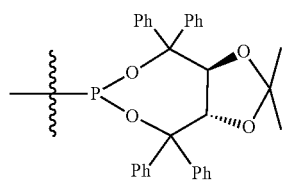
(R)-L31
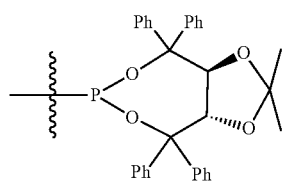
(S)-L31
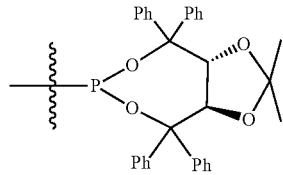
L32
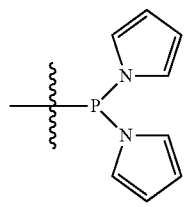
-continued
L27
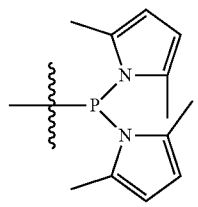
L28
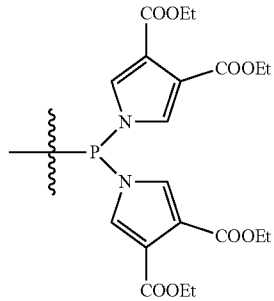
L29
L30
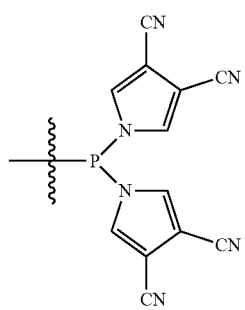
L31
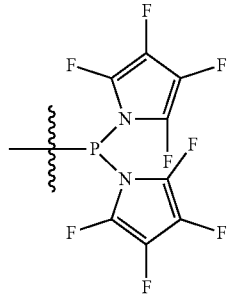
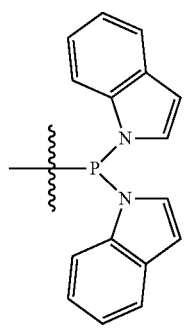
L33
L34
L35
L36
L37

-continued

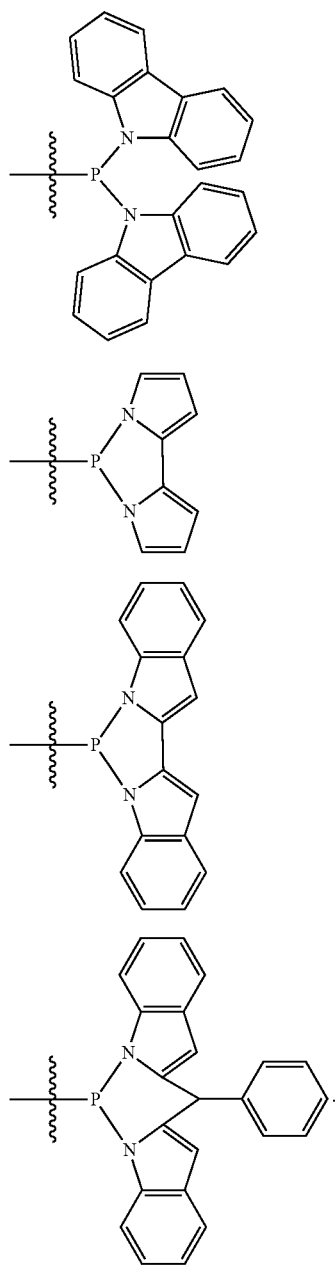

L38

L39

L40

L41

4. A method for preparing the spiro-bisphosphorous compound of claim 1, comprising:
subjecting 3-hydroxybenzaldehyde, 5-hydroxy-2-methoxybenzaldehyde, 3-methoxybenzaldehyde or 3-hydroxybenzaldehyde to alkylation, aldol condensation, hydrogenation and cyclodehydration in sequence to obtain 1,1'-spirobiindane-7,7'-diol; and subjecting the 1,1'-spirobiindane-7,7'-diol to esterification to obtain the spiro-bisphosphorous compound of formula (I) or (II);
subjecting 3-methoxyphenol to alkylation, nucleophilic substitution, oxidation, cyclodehydration and debromination in sequence to obtain 1,1'-spirobiindane-7,7'-diol; and subjecting the 1,1'-spirobiindane-7,7'-diol to esterification to obtain the spiro-bisphosphorous compound of formula (III); or
subjecting 1,3-dihalobenzene to lithiation, nucleophilic addition, dehydration, aldol condensation/Cannizzaro reaction, aromatic nucleophilic substitution, Pd/C-catalyzed debenzylation and alkylation in sequence to obtain 1,1'-spirobiindane-7,7'-diol; and subjecting the 1,1'-spirobiindane-7,7'-diol to esterification to obtain the spiro-bisphosphorous compound of formula (III).

5. The method of claim 4, wherein the spiro-bisphosphorous compound of formula (I) or (II) is prepared through steps of:
subjecting 3-hydroxybenzaldehyde to alkylation in the presence of a protonic acid or a Lewis acid to obtain 2, 4-di-tert-butyl-5-hydroxybenzaldehyde;
subjecting the 2, 4-di-tert-butyl-5-hydroxybenzaldehyde to aldol condensation with acetone in the presence of an alkali to obtain 1, 5-bis(2, 4-di-tert-butyl-5-hydroxyphenyl)-1, 4-pentadien-3-one;
subjecting the 1, 5-bis(2,4-di-tert-butyl-5-hydroxyphenyl)-1, 4-pentadien-3-one to hydrogenation in the presence of a reducing catalyst to obtain 1,5-bis(2,4-di-tert-butyl-5-hydroxyphenyl)-3-pentanone;
subjecting the 1,5-bis(2,4-di-tert-butyl-5-hydroxyphenyl)-3-pentanone to cyclization in the presence of a dehydrating agent to obtain 4,4',6,6'-tetra-tert-butyl-1, 1'-spirobiindane-7, 7'-diol;
sequentially adding the 4,4',6,6'-tetra-tert-butyl-1,1'-spirobiindane-7,7'-diol and an organic solvent to a reaction vessel under a nitrogen atmosphere to obtain a mixed solution; or sequentially adding the 4,4',6,6'-tetra-tert-butyl-1, 1'-spirobiindane-7, 7'-diol and an organic solvent to a reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and
dropwise adding, a mixture composed of a chlorophosphite compound and an acid-binding agent or an organic solution of a chlorinated form of a phosphite to the mixed solution of the 4,4',6,6'-tetra-tert-butyl-1, 1'-spirobiindane-7, 7'-diol and the organic solvent or the lithiation product, followed by esterification at room temperature, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

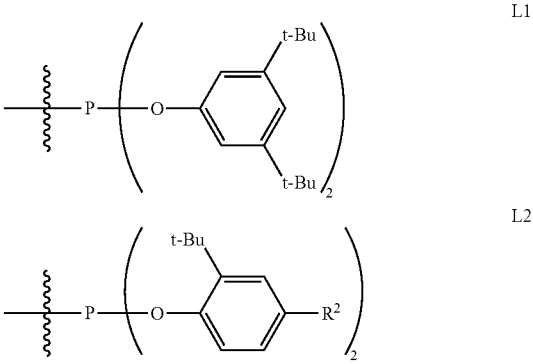

L1

L2

$R^2$ = t-Bu, H, Me, OMe, $CF_3$, Cl

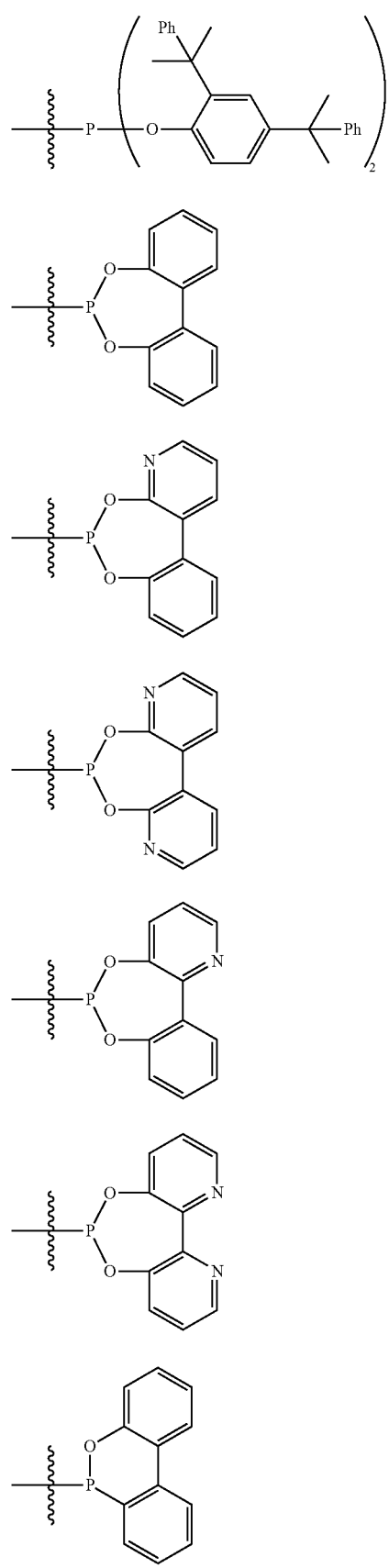
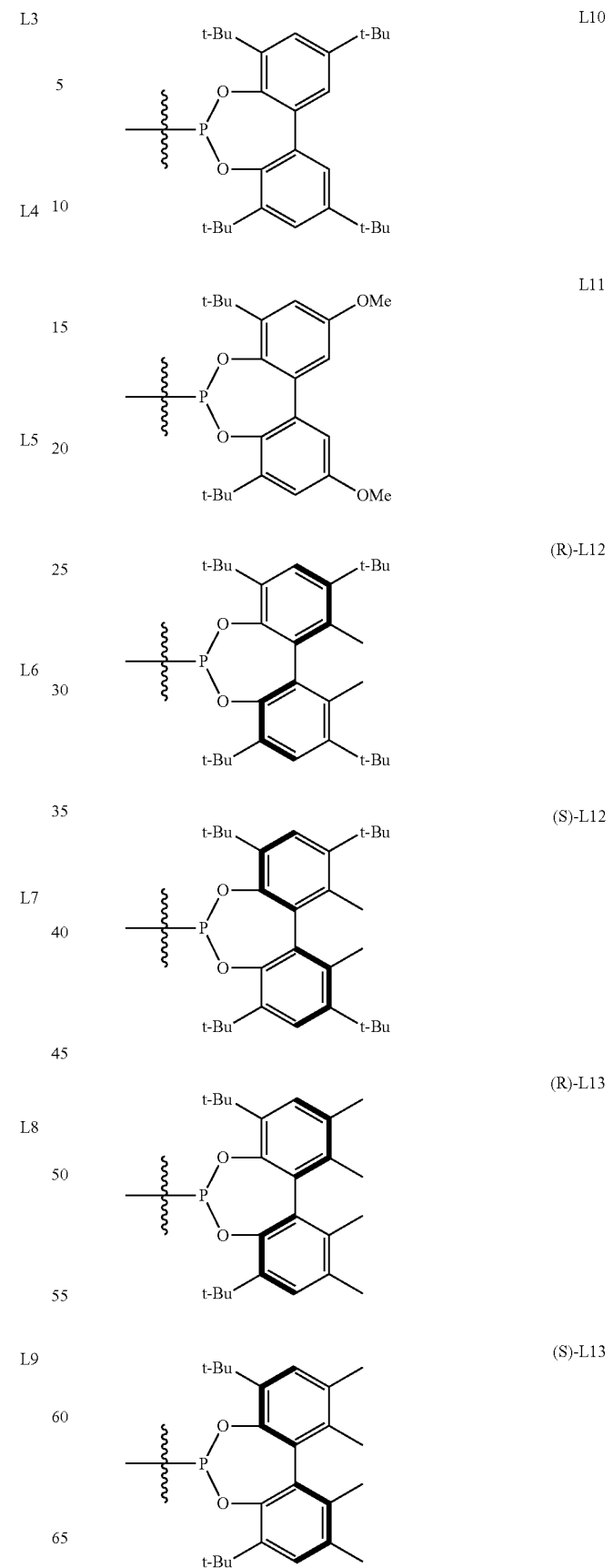

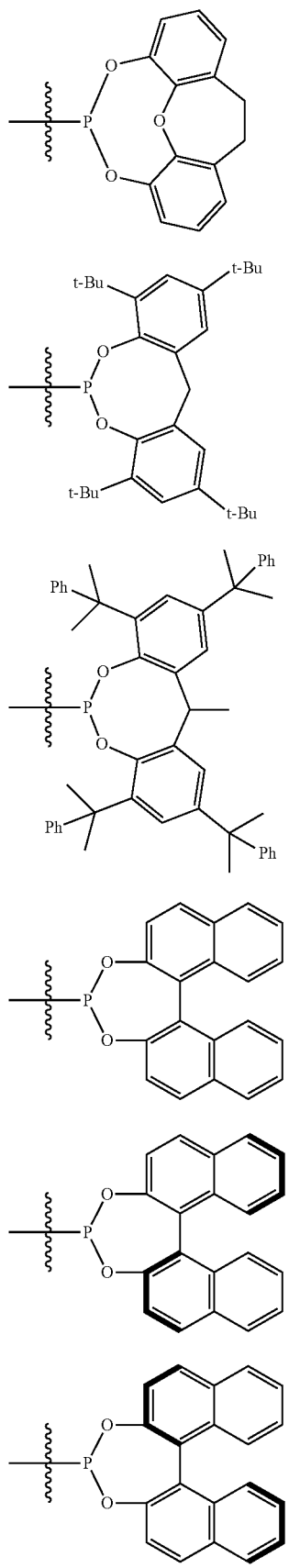
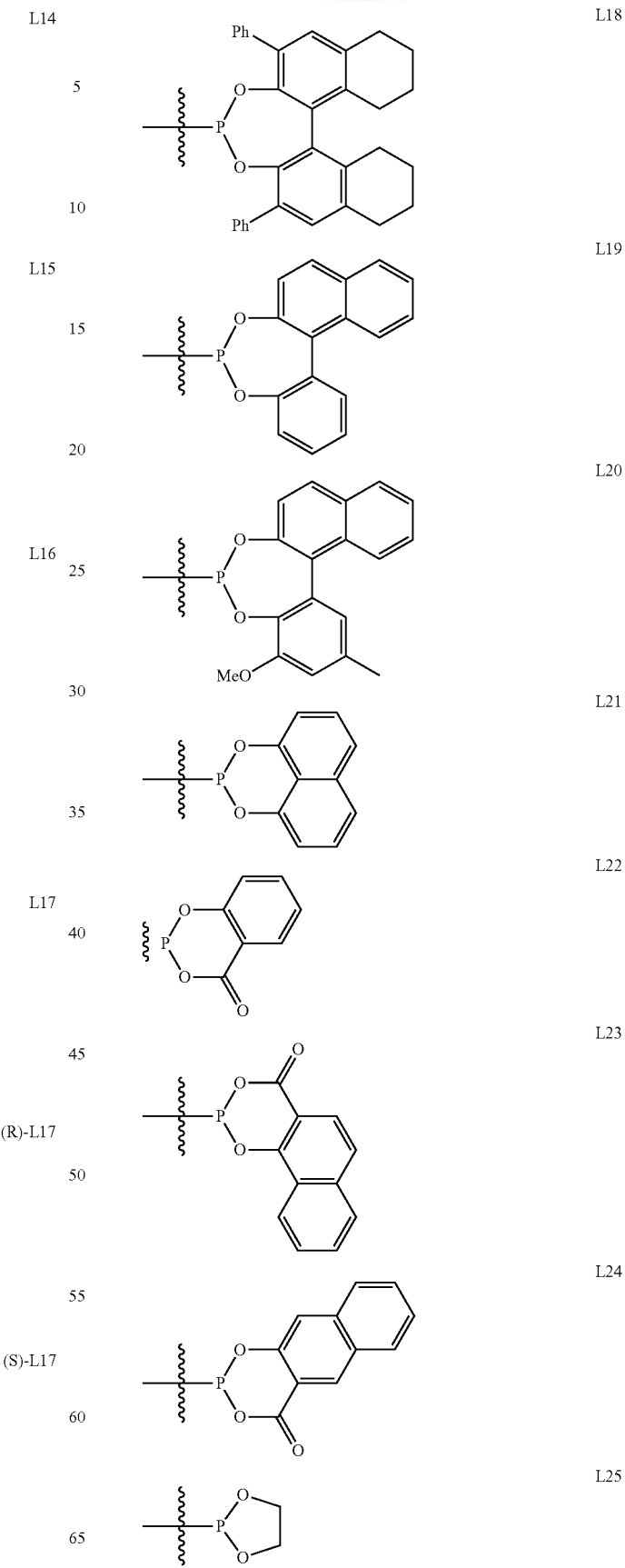

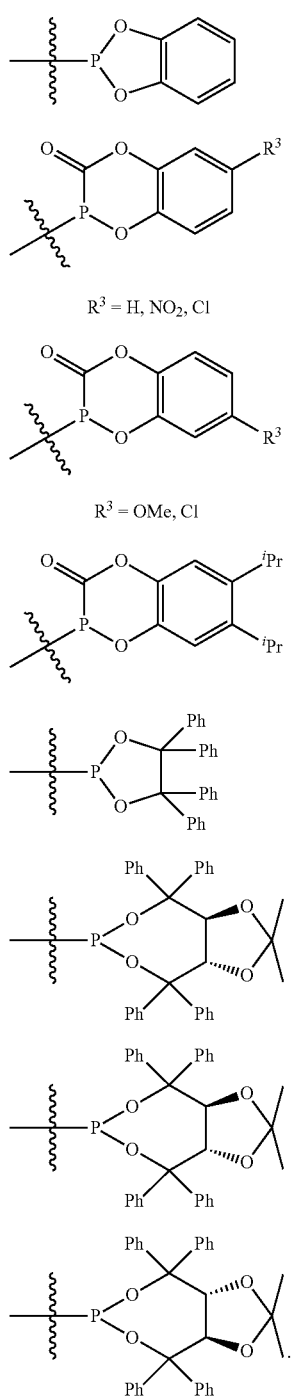

(R)-L31

(S)-L31

6. The method of claim 4, wherein the spiro-bisphosphorous compound of formula (I) or (II) is prepared through steps of:
subjecting 5-hydroxy-2-methoxybenzaldehyde to alkylation in the presence of a protonic acid or a Lewis acid to obtain 2-methoxy-4-tert-butyl-5-hydroxybenzaldehyde;
subjecting the 2-methoxy-4-tert-butyl-5-hydroxybenzaldehyde to aldol condensation with acetone in the presence of an alkali to obtain 1, 5-bis(2-methoxy-4-tert-butyl-5-hydroxyphenyl)-1, 4-pentadien-3-one;
subjecting the 1, 5-bis(2-methoxy-4-tert-butyl-5-hydroxyphenyl)-1, 4-pentadien-3-one to hydrogenation in the presence of a reducing catalyst to obtain 1, 5-bis(2-methoxy-4-tert-butyl-5-hydroxyphenyl)-3-pentanone;
subjecting the 1, 5-bis(2-methoxy-4-tert-butyl-5-hydroxyphenyl)-3-pentanone to cyclization in the presence of a dehydrating agent to obtain 4, 4'-dimethoxy-6, 6'-di-tert-butyl-1, 1'-spirobiindane-7, 7'-diol;
sequentially adding the 4, 4'-dimethoxy-6, 6'-di-tert-butyl-1, 1'-spirobiindane-7, 7'-diol and an organic solvent to a reaction vessel under a nitrogen atmosphere to obtain a mixed solution; or sequentially adding the 4, 4'-dimethoxy-6, 6'-di-tert-butyl-1, 1'-spirobiindane-7, 7'-diol and an organic solvent to the reaction vessel under a nitrogen atmosphere; dropwise adding n-butyllithium at −78∼−10° C. to obtain a reaction mixture; and restoring the reaction mixture to room temperature followed by reaction under reflux to obtain a lithiation product; and
dropwise adding, at a −78∼−10° C., a mixture composed of a chlorophosphite compound and an acid-binding agent or an organic solution of a chlorinated form of a phosphite to the mixed solution of the 4, 4'-dimethoxy-6, 6'-di-tert-butyl-1, 1'-spirobiindane-7, 7'-diol and the organic solvent or the lithiation product, followed by esterification at room temperature, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

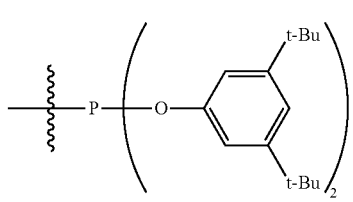

L1

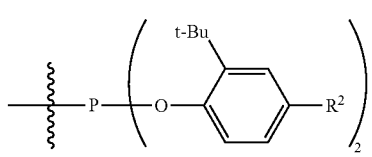

L2

$R^2$ = t-Bu, H, Me, OMe, $CF_3$, Cl

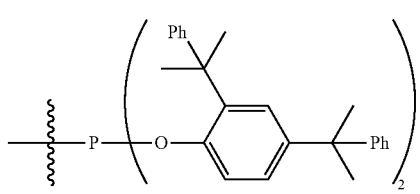

L3

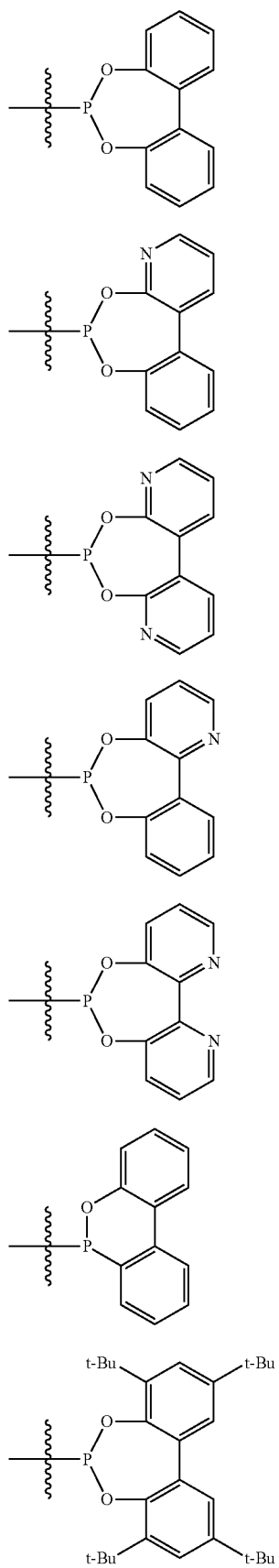
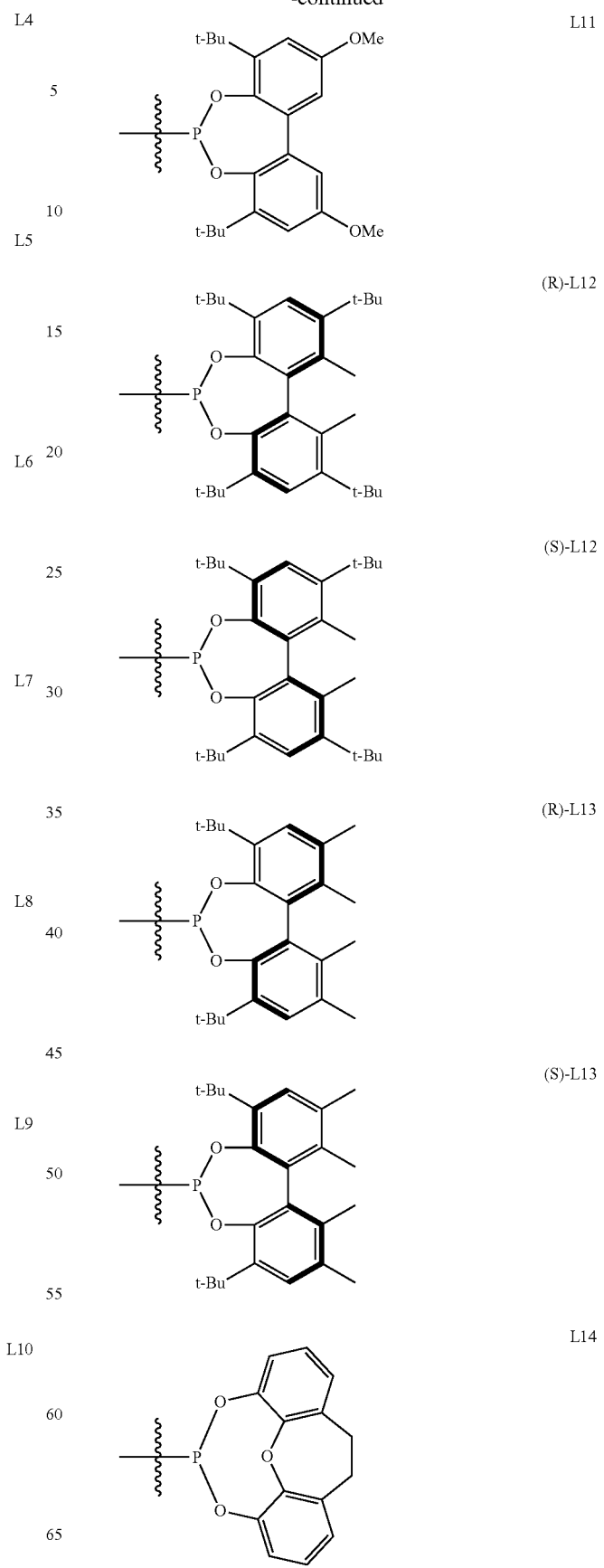

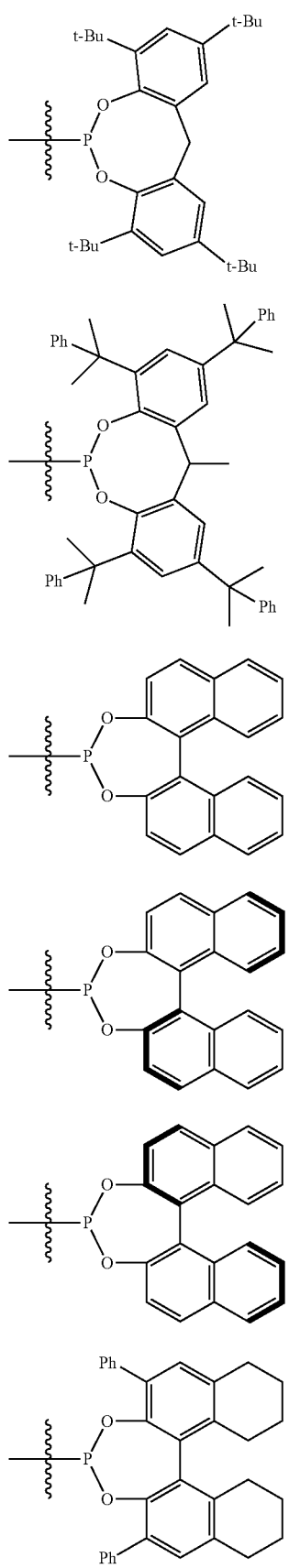
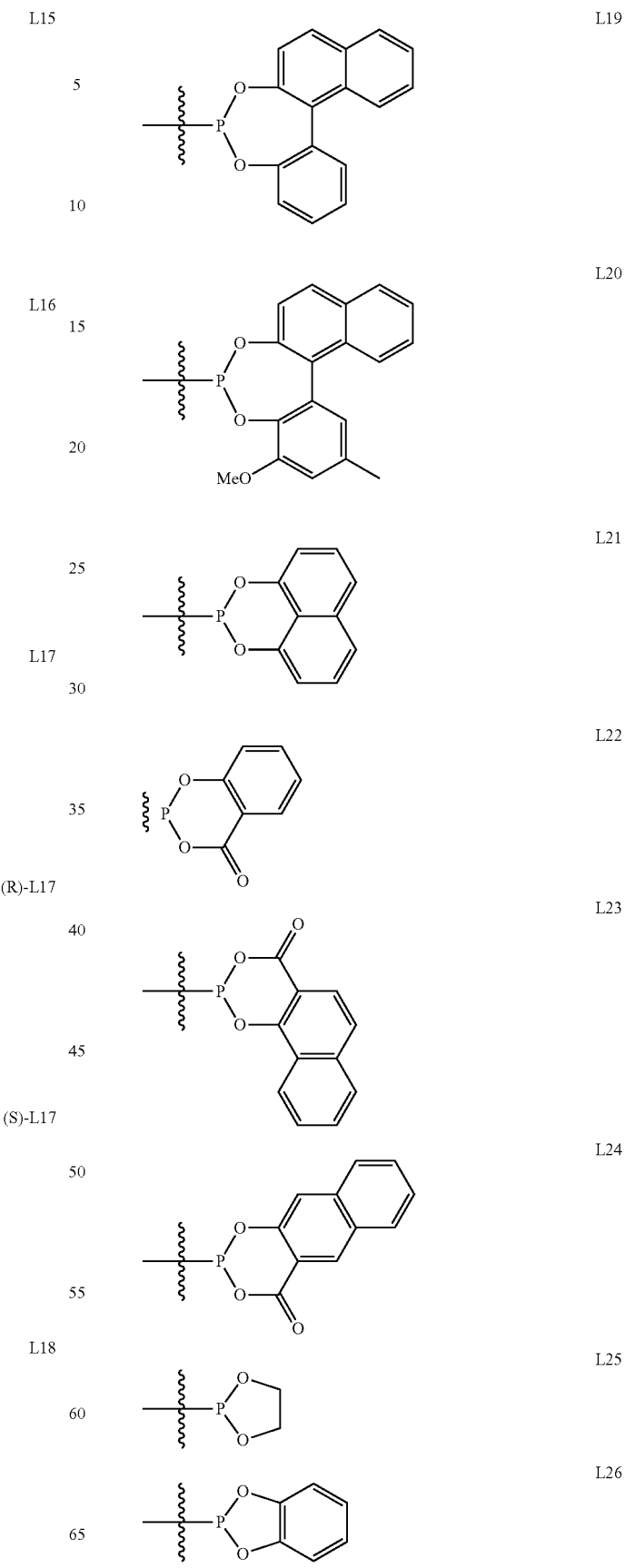

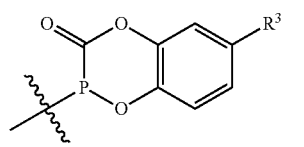

L27

R³ = H, NO₂, Cl

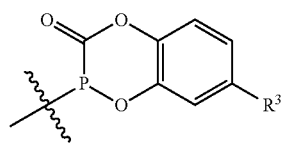

L28

R³ = OMe, Cl

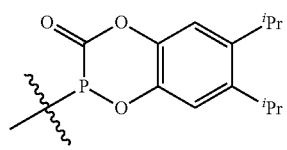

L29

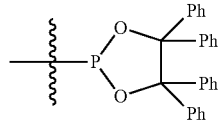

L30

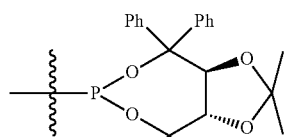

L31

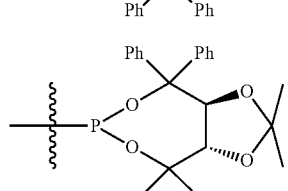

(R)-L31

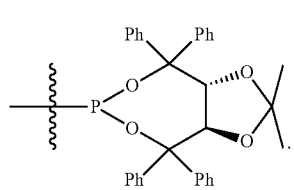

(S)-L31

7. The method of claim 4, wherein the spiro-bisphosphorous compound of formula (I) or (II) is prepared through steps of:

subjecting 3-methoxybenzaldehyde to aldol condensation with acetone to obtain 1, 5-bis(3-methoxyphenyl)-1, 4-pentadien-3-one; and subjecting the 1, 5-bis(3-methoxyphenyl)-1, 4-pentadien-3-one to halogenation with bromine or N-bromosuccinimide (NBS) to obtain 1, 5-bis(2-bromo-3-methoxyphenyl)-1, 4-pentadien-3-one;

subjecting the 1, 5-bis(2-bromo-3-methoxyphenyl)-1, 4-pentadien-3-one to hydrogenation in the catalysis of a metal catalyst to obtain 1, 5-bis(2-bromo-3-methoxyphenyl)-3-pentanone;

subjecting the 1, 5-bis(2-bromo-3-methoxyphenyl)-3-pentanone to cyclization in the presence of a dehydrating agent to obtain 4, 4'-dibromo-7, 7'-dimethoxy-1, 1'-spirobiindane;

subjecting the 4, 4'-dibromo-7, 7'-dimethoxy-1, 1'-spirobiindane to debromination in the presence of n-butyllithium to obtain 7, 7'-dimethoxy-1, 1'-spirobiindane;

subjecting the 7, 7'-dimethoxy-1, 1'-spirobiindane to demethylation in the presence of a demethylation agent to obtain 1, 1'-spirobiindane-7, 7'-diol;

subjecting the 1, 1'-spirobiindane-7, 7'-diol to alkylation with tert-butanol in the catalysis of a protonic acid or a Lewis acid to obtain 4,4',6,6'-tetra-tert-butyl-1, 1'-spirobiindane-7, 7'-diol;

sequentially adding the 4,4',6,6'-tetra-tert-butyl-1, 1'-spirobiindane-7, 7'-diol and an organic solvent to a reaction vessel under a nitrogen atmosphere to obtain a mixed solution; or sequentially adding the 4,4',6,6'-tetra-tert-butyl-1, 1'-spirobiindane-7, 7'-diol and an organic solvent to the reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and dropwise adding a mixture composed of a chlorophosphite compound and an acid-binding agent or an organic solution of a chlorinated form of a phosphite to the mixed solution of the 4,4',6,6'-tetra-tert-butyl-1, 1'-spirobiindane-7, 7'-diol and the organic solvent or the lithiation product, followed by esterification at room temperature, filtration to remove inorganic salts, concentration and crystallization to obtain the spirobisphosphorous compound, wherein the chlorophosphite compound comprises an aryl group selected from the group consisting of a biphenyl, methylene diphenyl, binaphthyl, benzoyloxy, o-phenyl, phenyl, or naphthyl group, and the phosphite is selected from the group consisting of:

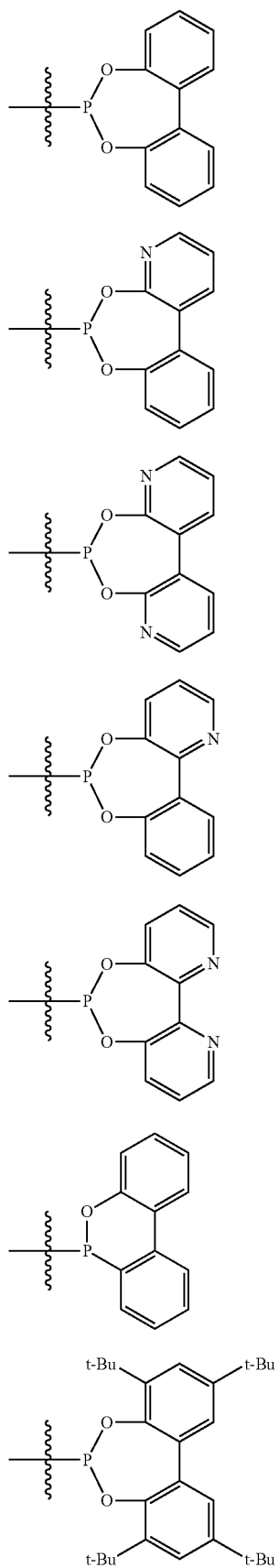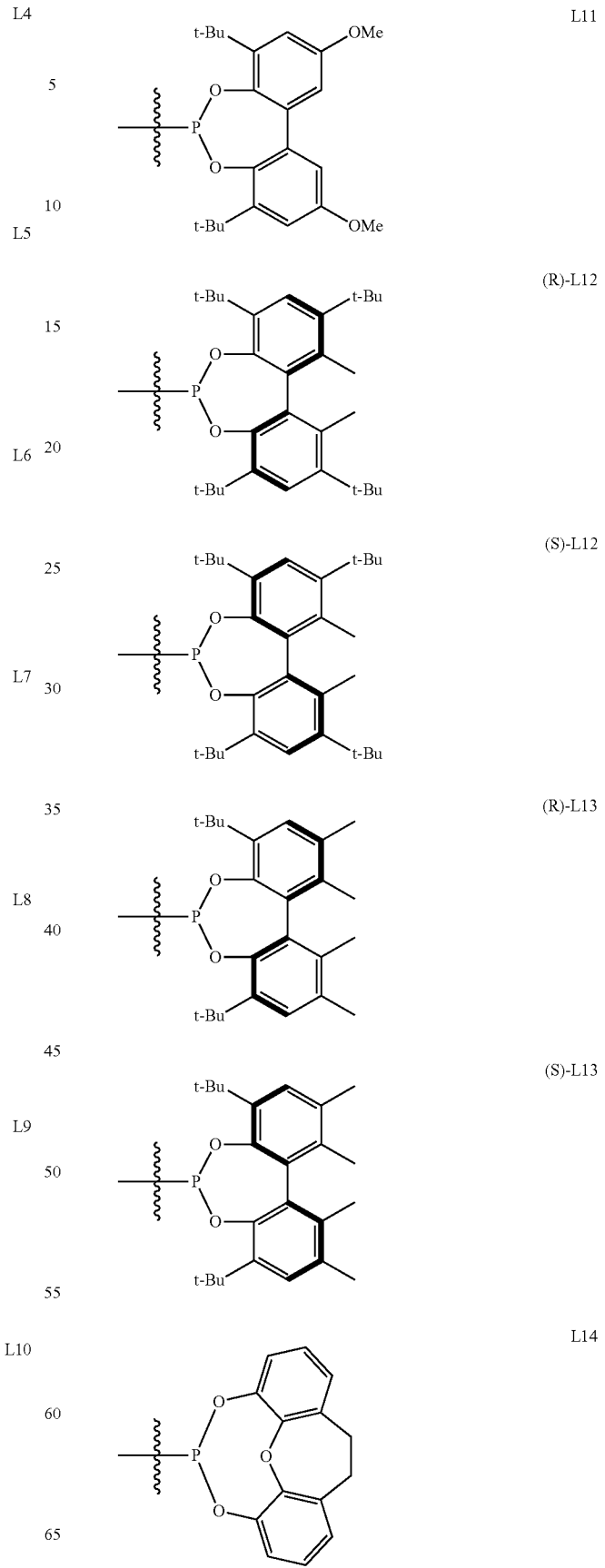

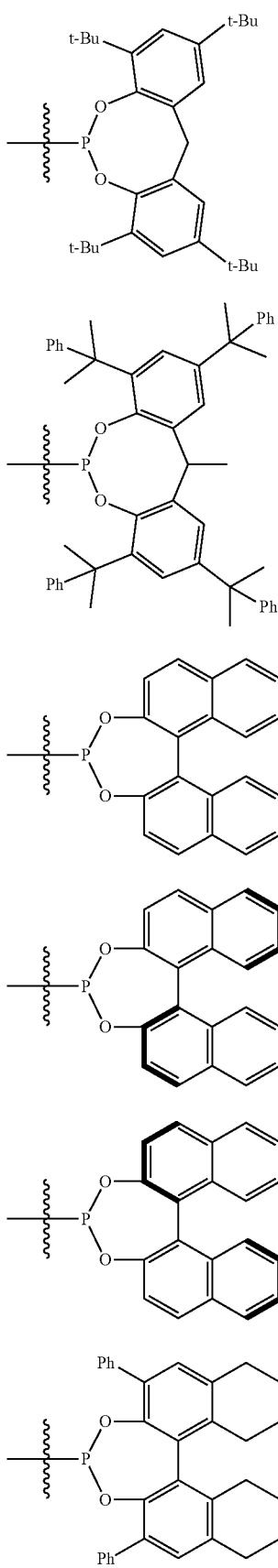
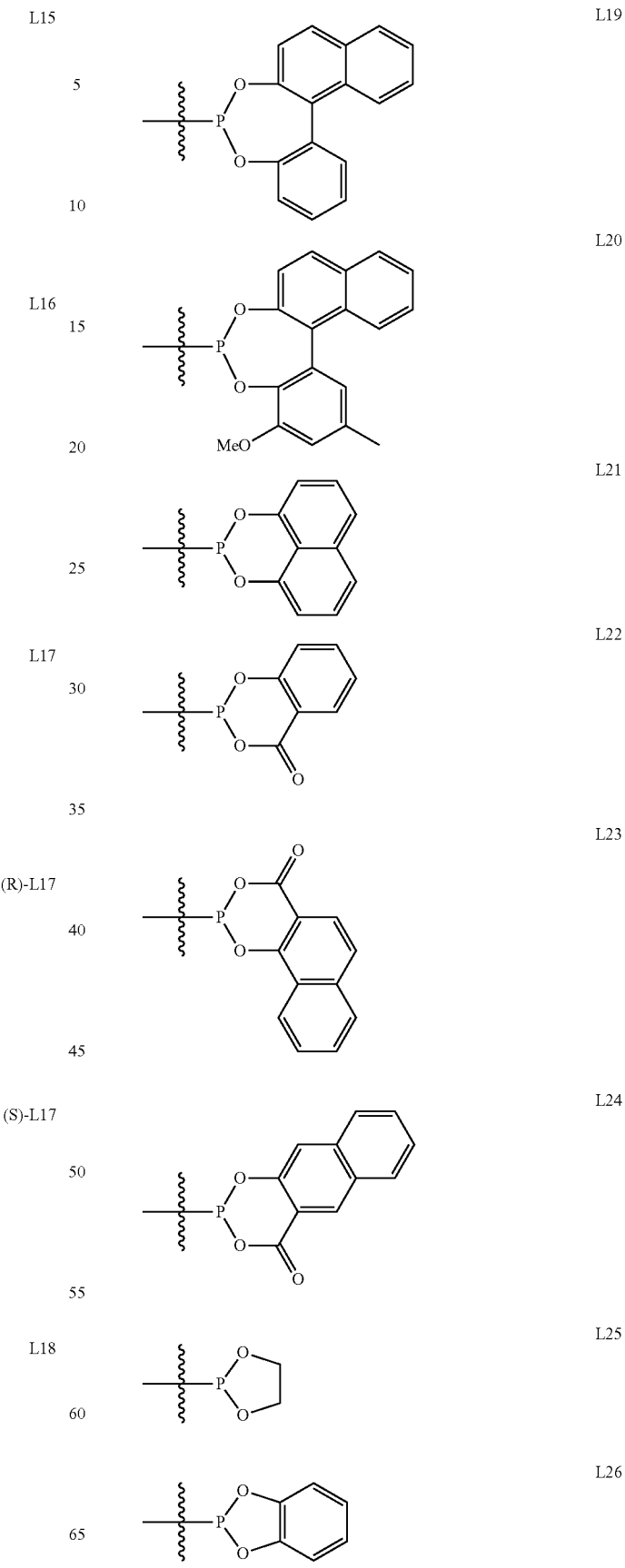

-continued

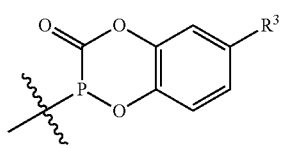

L27

R³ = H, NO₃, Cl

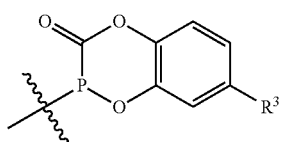

L28

R³ = OMe, Cl

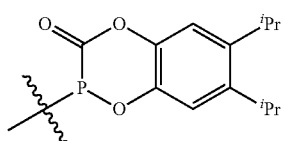

L29

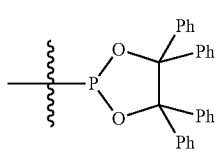

L30

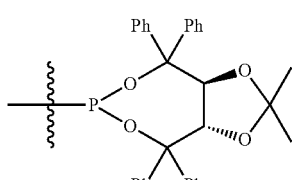

L31

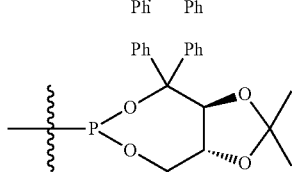

(R)-L31

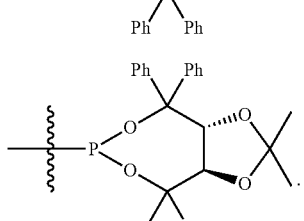

(S)-L31

8. The method of claim 4, wherein the spiro-bisphosphorous compound of formula (I) or (II) is prepared through steps of:

subjecting 3-hydroxybenzaldehyde to halogenation with bromine or NBS to obtain 2-bromo-5-hydroxybenzaldehyde; and subjecting the 2-bromo-5-hydroxybenzaldehyde to aldol condensation with acetone to obtain 1, 5-bis(2-bromo-3-hydroxyphenyl)-1, 4-pentadien-3-one;

subjecting the 1, 5-bis(2-bromo-3-hydroxyphenyl)-1, 4-pentadien-3-one to hydrogenation in the catalysis of a metal catalyst to obtain 1,5-bis(2-bromo-3-hydroxyphenyl)-3-pentanone;

subjecting the 1, 5-bis(2-bromo-3-hydroxyphenyl)-3-pentanone to cyclization in the presence of a dehydrating agent to obtain 4, 4'-dibromo-7, 7'-dihydroxy-1, 1'-spirobiindane;

subjecting the 4, 4'-dibromo-7, 7'-dihydroxy-1, 1'-spirobiindane to debromination in the presence of Pd/C to obtain 1,1'-spirobiindane-7,7'-diol;

sequentially adding the 1,1'-spirobiindane-7,7'-diol and an organic solvent to a reaction vessel under a nitrogen atmosphere to obtain a mixed solution; or sequentially adding the 1,1'-spirobiindane-7,7'-diol and an organic solvent to a reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and dropwise adding a mixture of a chlorophosphite compound and an acid-binding agent to the mixed solution of the 1,1'-spirobiindane-7,7'-diol and the organic solvent followed by esterification at room temperature, filtration to remove inorganic salts, concentration and crystallization to obtain the spiro-bisphosphorous compound; or dropwise adding an organic solution of a chlorinated form of a phosphite to the lithiation product followed by esterification, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

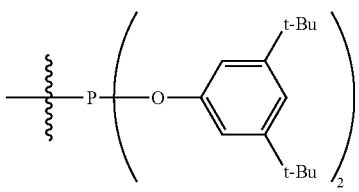

L1

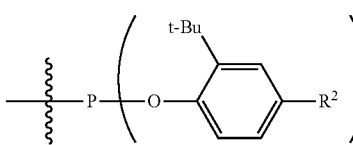

L2

R² = t-Bu, H, Me, OMe, CF₃, Cl

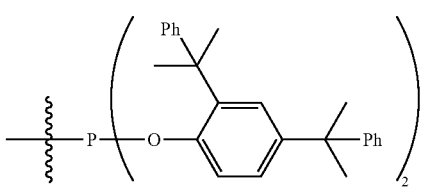

L3

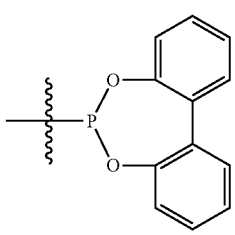

L4

L5
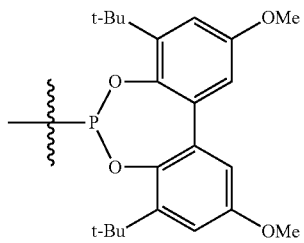
L6
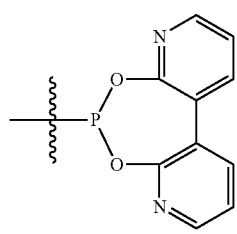
L7
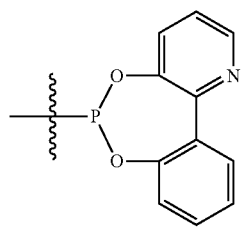
L8
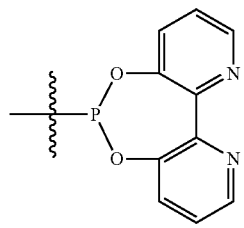
L9
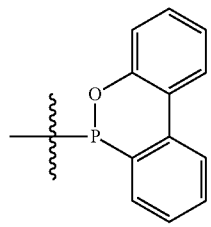
L10
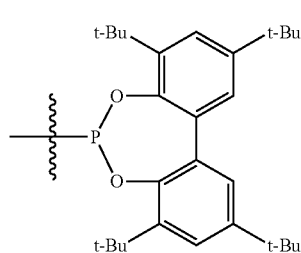
L11
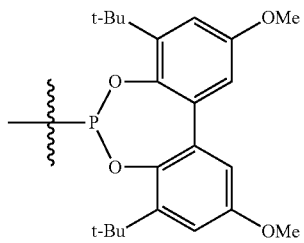
(R)-L12
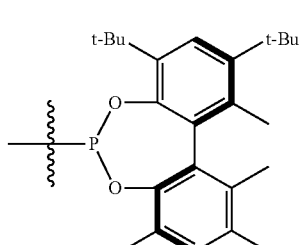
(S)-L12
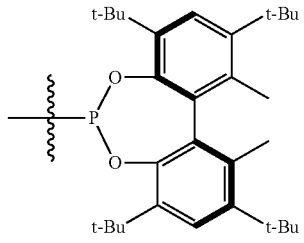
(R)-L13
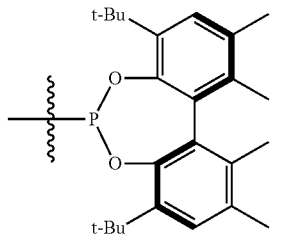
(S)-L13
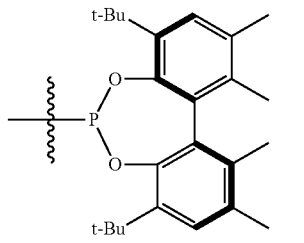
L14
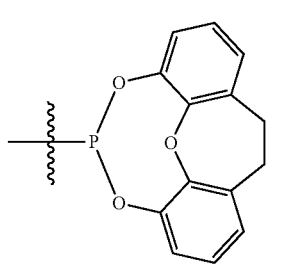

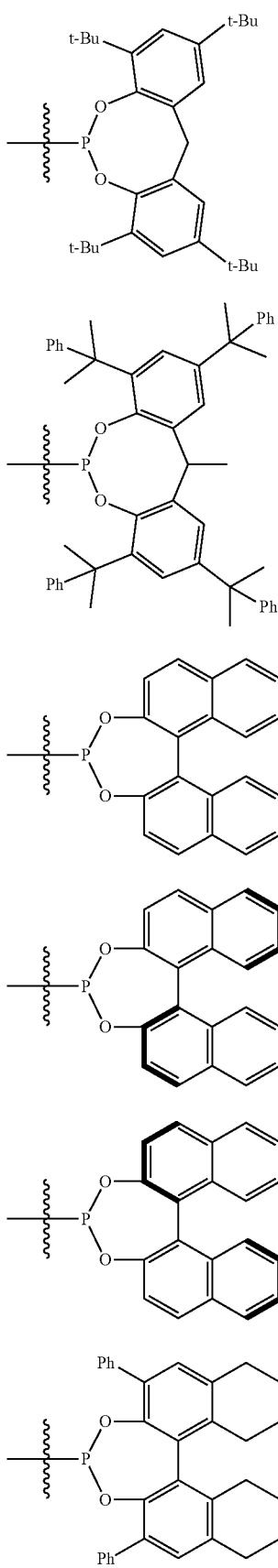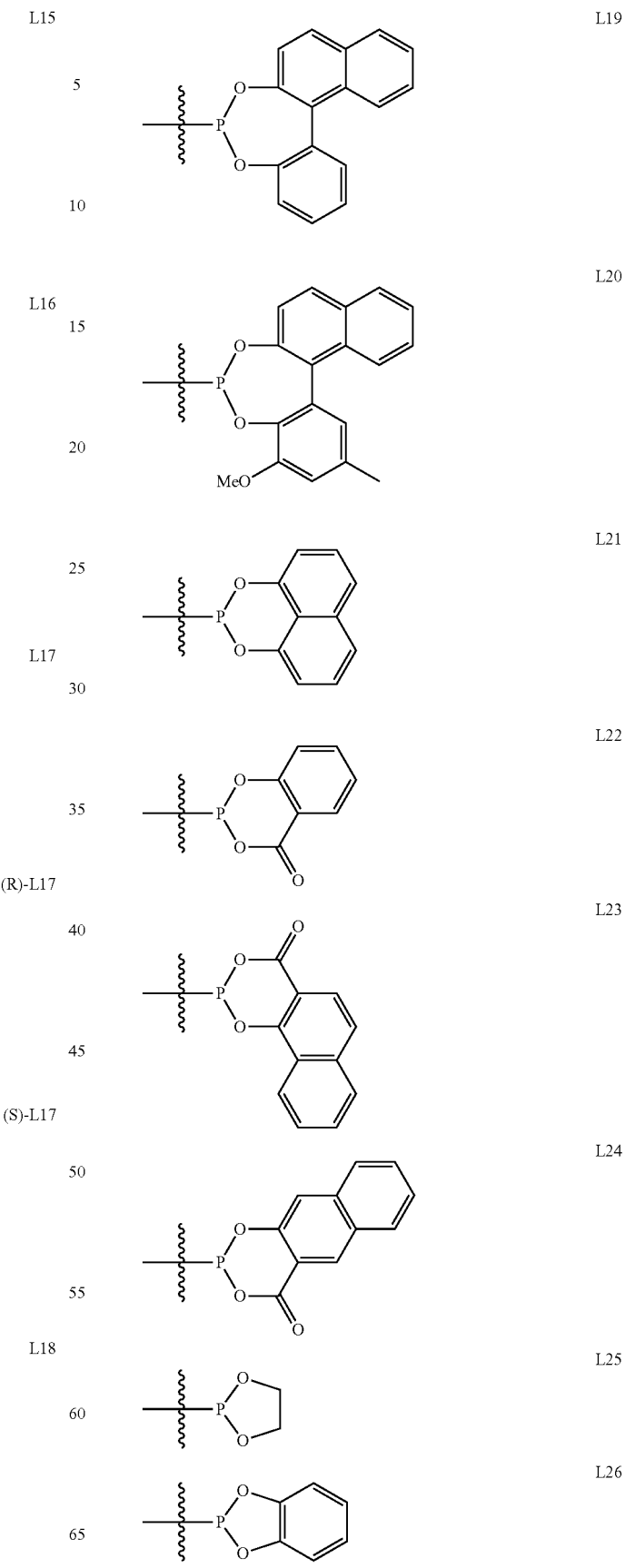

-continued

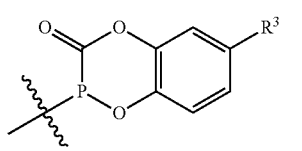

L27

R³ = H, NO₃, Cl

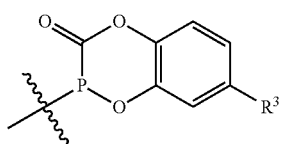

L28

R³ = OMe, Cl

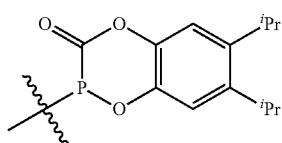

L29

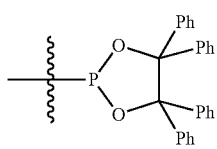

L30

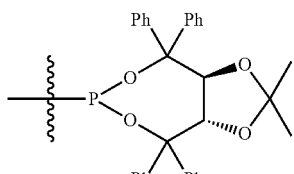

L31

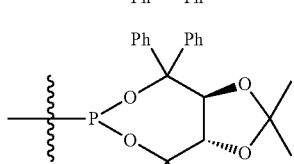

(R)-L31

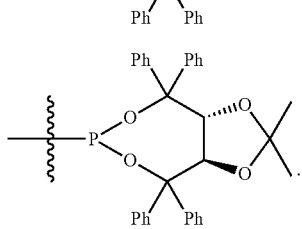

(S)-L31

9. The method of claim 4, wherein in the alkylation, the protonic acid or Lewis acid is an organic acid, an inorganic acid or a combination thereof;
the organic acid is selected from the group consisting of formic acid, acetic acid, oxalic acid, dichloroacetic acid, trifluoroacetic acid, propionic acid, malonic acid, pyruvic acid, butyric acid, valeric acid, caproic acid, adipic acid, benzoic acid, p-nitrobenzoic acid, terephthalic acid, benzenesulfonic acid, fluorosulfonic acid, methanesulfonic acid, trifluoromethanesulfonic acid, p-toluenesulfonic acid and a combination thereof;
the inorganic acid is selected from the group consisting of hydrobromic acid, hydrochloric acid, hydrofluoric acid, sulfurous acid, sulfuric acid, perchloric acid, phosphonic acid, pyrophosphoric acid, nitric acid, nitrous acid, chromic acid, magic acid, fluoroantimonic acid and a combination thereof;
an alkylating agent used in the alkylation is tert-butyl bromide, tert-butyl chloride, isobutene or tert-butanol;
a solvent used in the alkylation is benzene, toluene, p-toluene, p-xylene, o-xylene, chlorobenzene or dichlorobenzene; and
the alkylation is performed at 80-140° C.

10. The method of claim 4, wherein the aldol condensation is performed at 20-75° C. in a solvent in the presence of 1.5-10 equivalents of an alkali; the alkali is selected from the group consisting of potassium hydroxide, sodium hydroxide, potassium carbonate, sodium carbonate, sodium tert-butoxide and potassium tert-butoxide; and
the solvent is ethanol, water or an ethanol-water mixture, wherein a volume ratio of ethanol to water in the ethanol-water mixture is (1-9):1.

11. The method of claim 4, wherein the hydrogenation is performed at a temperature of 20-50° C. and a hydrogen pressure of 0.05-5 MPa in a solvent in the presence of a catalyst for 24-72 h;
wherein the catalyst is Raney nickel, ferric chloride, cobalt oxide or Pd/C; and
the solvent is ethyl acetate, tetrahydrofuran, dichloromethane or 1,4-dioxane.

12. The method of claim 4, wherein the cyclodehydration is performed at 45-135° C. in a solvent in the presence of 10-70 equivalents of a dehydrating agent for 2-6 h;
wherein the dehydrating agent is polyphosphoric acid, concentrated sulfuric acid, acetic anhydride, methanesulfonic acid, benzoic acid, p-toluenesulfonic acid or anhydrous aluminum trichloride;
the solvent is toluene, n-heptane, dichloromethane, trichloromethane or dichloroethane.

13. The method of claim 4, wherein the esterification between the chlorophosphite compound and the 1,1'-spirobiindane-7,7'-diol is performed in the presence of 5-20 equivalents of the acid-binding agent for 12-48 h, and the acid-binding agent is triethylamine, N,N-diisopropylethylamine or pyridine;
the esterification between the chlorinated form of the phosphite and the lithiation product is performed at −78-80° C. in the presence of 2-4 equivalents of n-butyllithium for 12-48 h;
the lithiation product is produced in the presence of 2-4 equivalents of n-butyllithium; and
the organic solvent is selected from the group consisting of toluene, tetrahydrofuran, diethyl ether, 2-methyltetrahydrofuran, methyl tert-butyl ether, isopropyl ether, anisole, ethylene glycol dimethyl ether, diethylene glycol dimethyl ether, butyl ether, cyclopentyl methyl ether and 1, 4-dioxane.

14. The method of claim 5, wherein the crystallization is performed in a solvent selected from the group consisting of ethyl acetate, toluene, dichloromethane, ethanol, acetonitrile, petroleum ether, n-hexane, tetrahydrofuran and a combination thereof.

15. The method of claim 4, wherein the spiro-bisphosphorous compound of formula (III) is prepared through steps of:
subjecting 1, 3-difluorobenzene to lithiation with n-butyllithium to obtain an aryl lithium reagent; reacting the aryl lithium reagent with methyl trimethylsilyl (TMS) glycolate to obtain an aryl ketone; and subjecting the aryl ketone to nucleophilic addition with the aryl lithium reagent followed by hydrolysis with dilute hydrochloric acid and removal of TMS group to obtain 1, 1-bis(2, 6-difluorophenyl)-1, 2-ethanediol;

heating the 1, 1-bis(2, 6-difluorophenyl)-1, 2-ethanediol under reflux in sulfuric acid followed by dehydration to obtain 1, 1-bis(2, 6-difluorophenyl)-acetaldehyde;

subjecting the 1, 1-bis(2, 6-difluorophenyl)-acetaldehyde to aldol condensation with paraformaldehyde in the catalysis of an alkali to obtain 1, 1-bis(2, 6-difluorophenyl)-3-hydroxypropionaldehyde; and subjecting the 1, 1-bis(2, 6-difluorophenyl)-3-hydroxypropionaldehyde to Cannizzaro reaction to obtain 1, 1-bis(2, 6-difluorophenyl)-1, 3-propanediol;

subjecting the 1, 1-bis(2, 6-difluorophenyl)-1, 3-propanediol and a leaving group to nucleophilic aromatic substitution (SNAr) in the presence of a first acid-binding agent followed by cyclization to obtain 1, 1'-spirodihydrobenzofuran-7, 7'-difluoro;

subjecting the 1, 1'-spirodihydrobenzofuran-7, 7'-difluoro to SNAr with benzyl alcohol in the presence of a second acid-binding agent to obtain 1, 1'-spirodihydrobenzofuran-7, 7'-dibenzyl ether;

subjecting the 1, 1'-spirodihydrobenzofuran-7, 7'-dibenzyl ether to debenzylation in the presence of Pd/C to obtain a racemic 1, 1'-spirodihydrobenzofuran-7, 7'-diol;

subjecting tert-butanol to dehydration in the catalysis of a protonic acid or a Lewis acid to obtain isobutylene; and subjecting the isobutylene and the racemic 1, 1'-spirodihydrobenzofuran-7, 7'-diol to electrophilic addition to obtain 4,4',6,6'-tetra-tert-butyl-1, 1'-spirodihydrobenzofuran-7, 7'-diol;

sequentially adding the 4,4',6,6'-tetra-tert-butyl-1, 1'-spirodihydrobenzofuran-7, 7'-diol and an organic solvent to a reaction vessel under a nitrogen atmosphere to obtain a mixed solution; or sequentially adding the 4,4',6,6'-tetra-tert-butyl-1, 1'-spirodihydrobenzofuran-7, 7'-diol and an organic solvent to a reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and dropwise adding a mixture of a chlorophosphite compound and an acid-binding agent to the mixed solution of the 4,4',6,6'-tetra-tert-butyl-1, 1'-spirodihydrobenzofuran-7, 7'-diol and the organic solvent followed by esterification at room temperature, filtration to remove inorganic salts, concentration and crystallization to obtain the spiro-bisphosphorous compound; or dropwise adding an organic solution of a chlorinated form of a phosphite to the lithiation product, followed by esterification, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

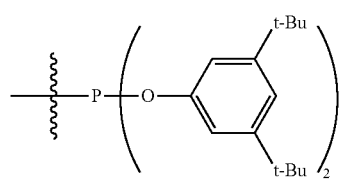

L1

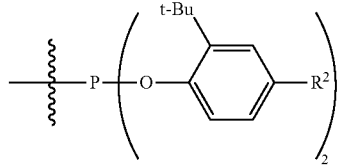

L2

$R^2$ = t-Bu, H, Me, OMe, $CF_3$, Cl

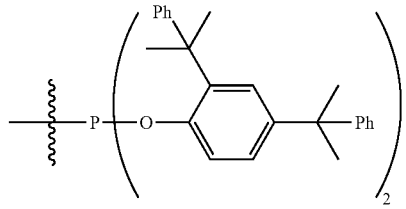

L3

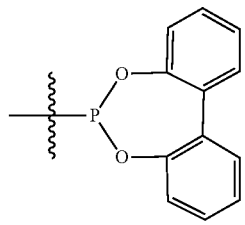

L4

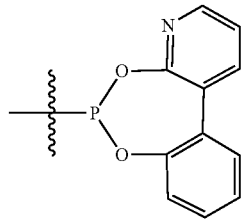

L5

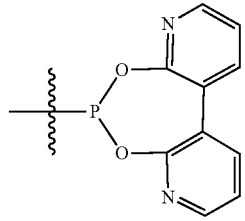

L6

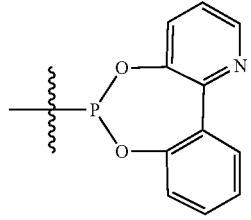

L7

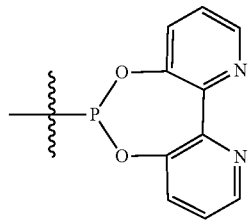

L8

-continued
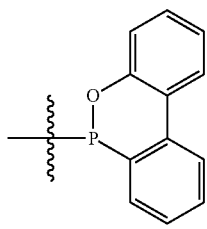
L9
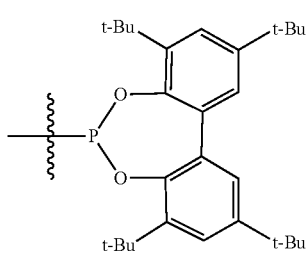
L10
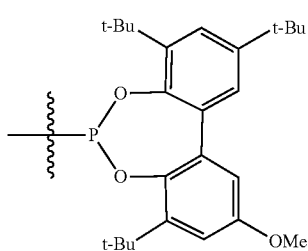
L11
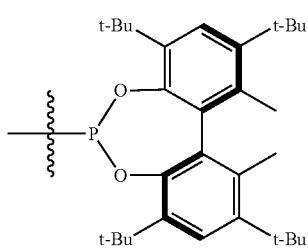
(R)-L12
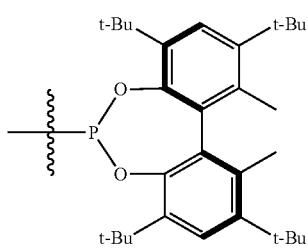
(S)-L12
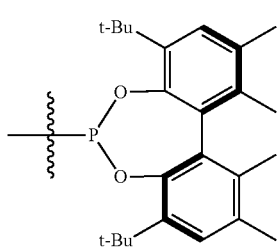
(R)-L13
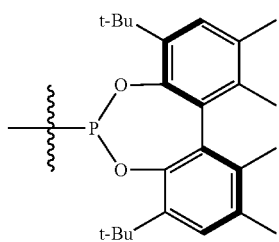
(S)-L13
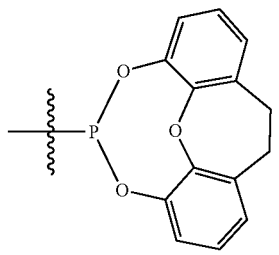
L14
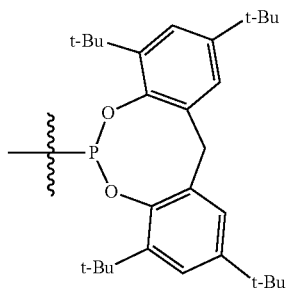
L15
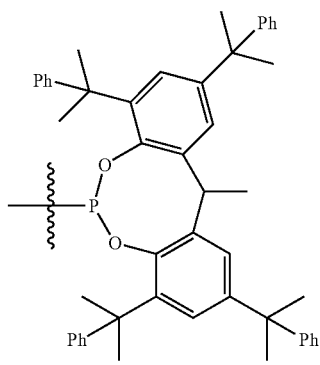
L16
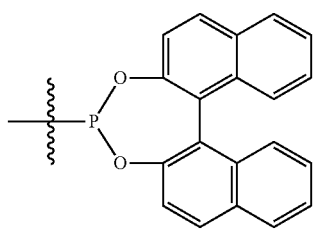
L17
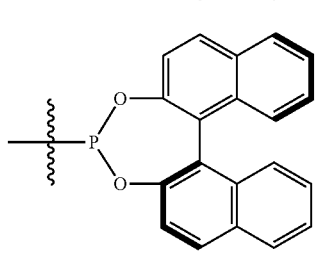
(R)-L17

-continued
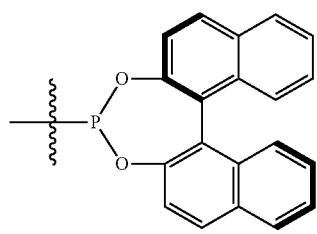
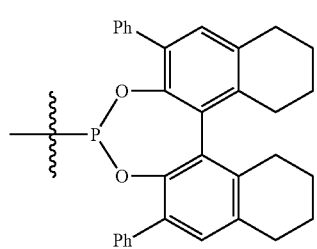
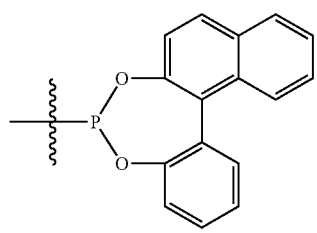
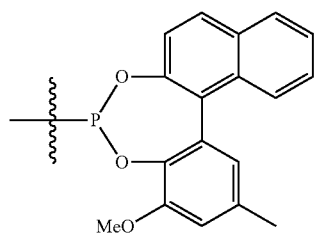
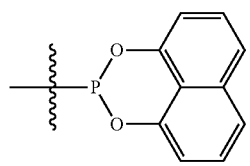
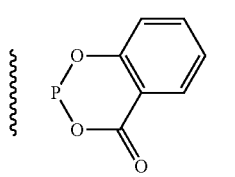
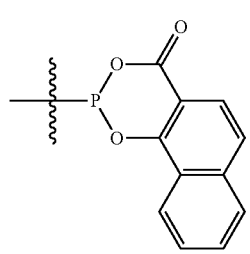
(S)-L17
L18
L19
L20
L21
L22
L23
-continued
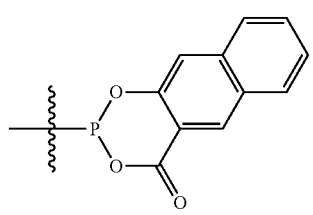
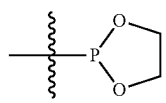
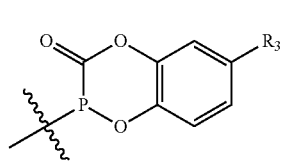
R³ = H, NO₂, Cl
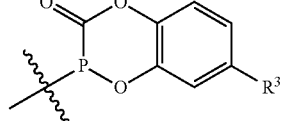
R³ = OMe, Cl
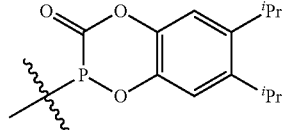
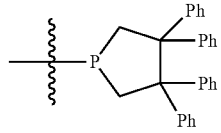
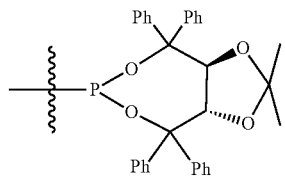
L24
L25
L26
L27
L28
L29
L30
L31
(R)-L31

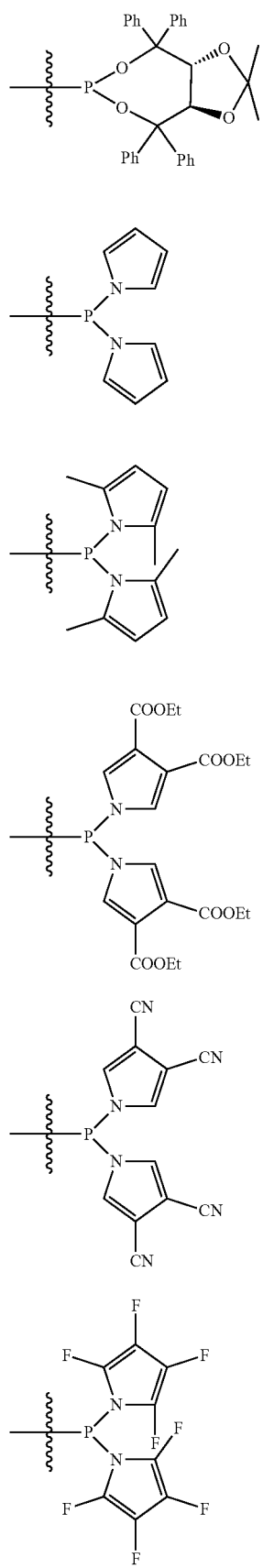
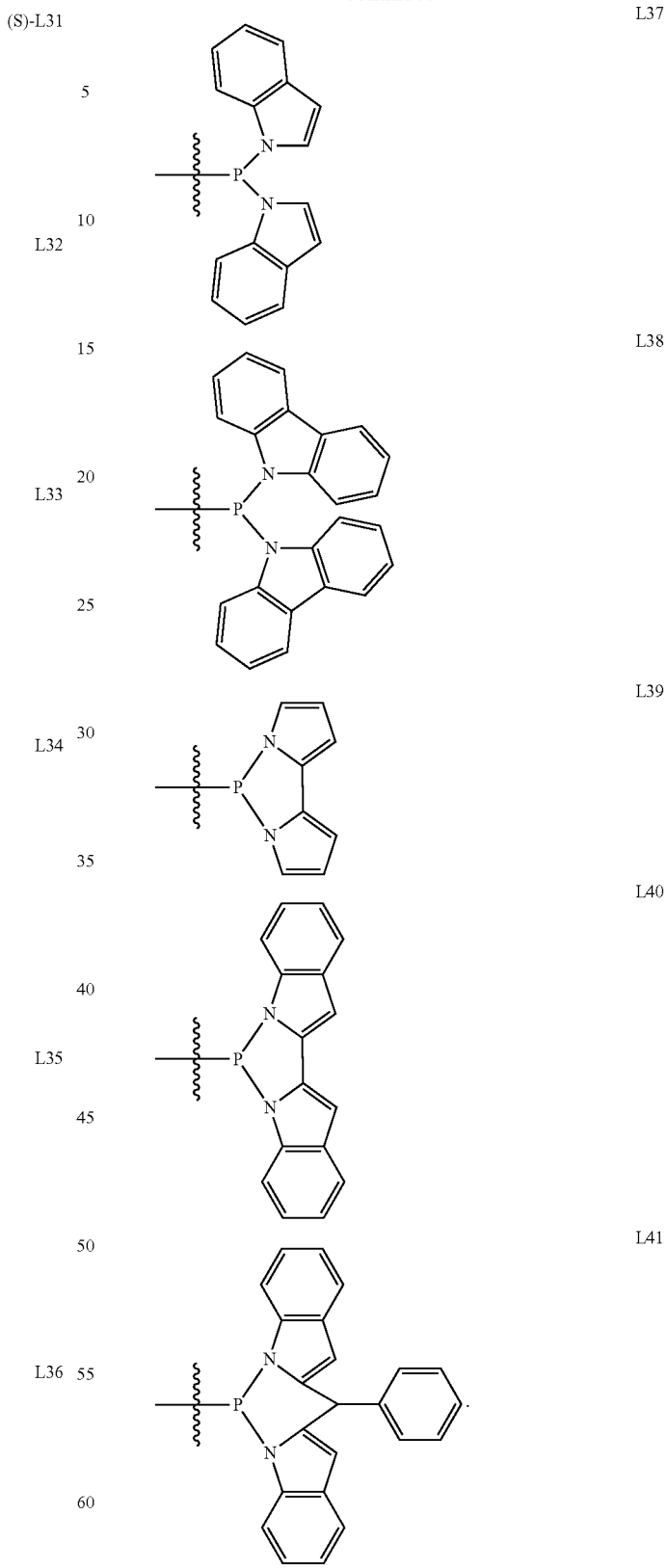
16. The method of claim 4, wherein the spiro-bisphosphorous compound of formula (III) is prepared through steps of:

subjecting 3-methoxyphenol to nucleophilic substitution with 1, 3-dichloro-2-propanol to obtain 1, 5-bis(3-methoxyphenoxy)-2-propanol;

subjecting the 1, 5-bis(3-methoxyphenoxy)-2-propanol to oxidation in the catalysis of chromium trioxide to obtain 1, 5-bis(3-methoxyphenoxy)-acetone;

subjecting the 1, 5-bis(3-methoxyphenoxy)-acetone to halogenation with bromine or NBS to obtain 1, 5-bis(2-bromo-3-methoxyphenoxy)-acetone;

subjecting the 1, 5-bis(2-bromo-3-methoxyphenoxy)-acetone to Friedel-Crafts reaction in the presence of a dehydrating agent to obtain 4, 4'-dibromo-7, 7'-dimethoxy-1, 1'-spirodihydrobenzofuran;

subjecting the 4, 4'-dibromo-7, 7'-dimethoxy-1, 1'-spirodihydrobenzofuran to debromination in the presence of n-butyllithium to obtain 7, 7'-dimethoxy-1, 1'-spirodihydrobenzofuran;

subjecting the 7, 7'-dimethoxy-1, 1'-spirodihydrobenzofuran to demethylation in the presence of a demethylation agent to obtain 1, 1'-spirodihydrobenzofuran-7, 7'-diol;

subjecting the 1, 1'-spirodihydrobenzofuran-7, 7'-diol and isobutene to alkylation to obtain 4,4',6,6'-tetra-tert-butyl-1, 1'-spirodihydrobenzofuran-7, 7'-diol;

sequentially adding the 4,4',6,6'-tetra-tert-butyl-1, 1'-spirodihydrobenzofuran-7, 7'-diol and an organic solvent to a reaction vessel under a nitrogen atmosphere to obtain a mixed solution; or sequentially adding the 4,4',6,6'-tetra-tert-butyl-1, 1'-spirodihydrobenzofuran-7, 7'-diol and an organic solvent to the reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and dropwise adding a mixture of a chlorophosphite compound and an acid-binding agent to the mixed solution of the 4,4',6,6'-tetra-tert-butyl-1, 1'-spirodihydrobenzofuran-7, 7'-diol and the organic solvent followed by esterification at room temperature, filtration to remove inorganic salts, concentration and crystallization to obtain the spiro-bisphosphorous compound; or dropwise adding an organic solution of a chlorinated form of a phosphite to the lithiation product, followed by esterification, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

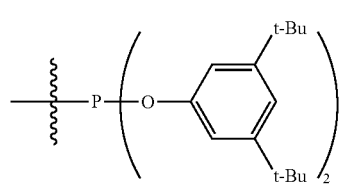

L1

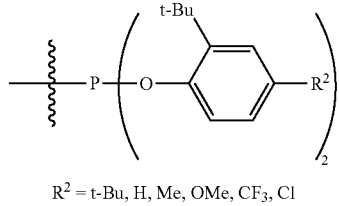

$R^2$ = t-Bu, H, Me, OMe, CF$_3$, Cl

L2

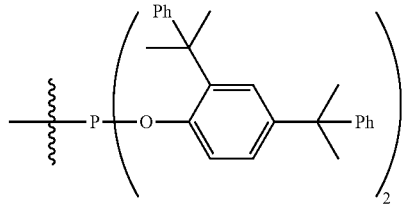

L3

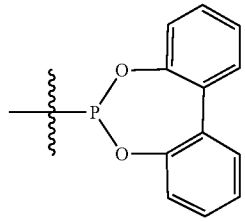

L4

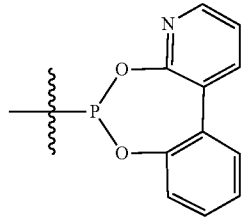

L5

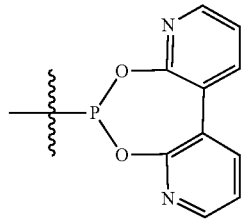

L6

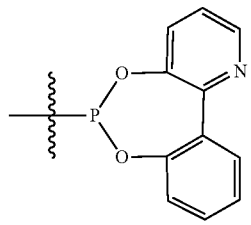

L7

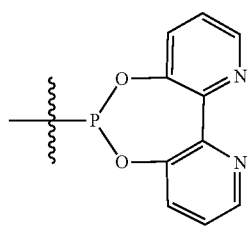

L8

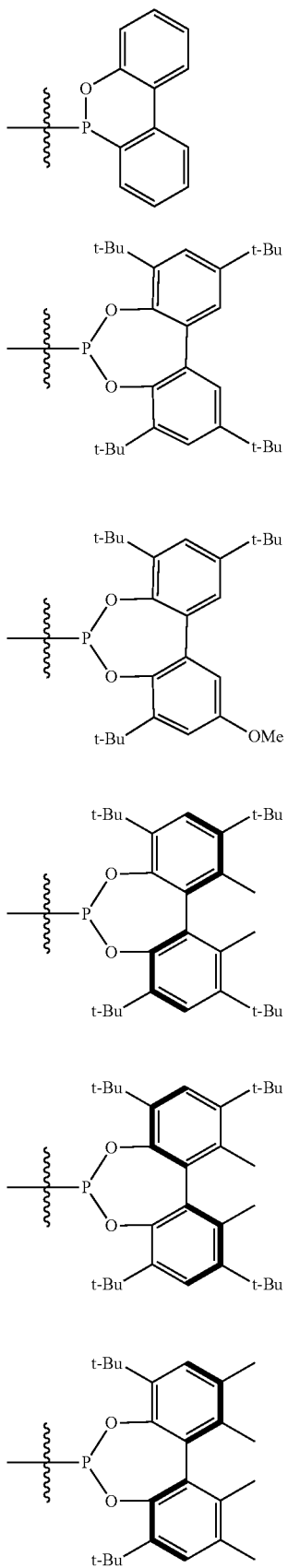
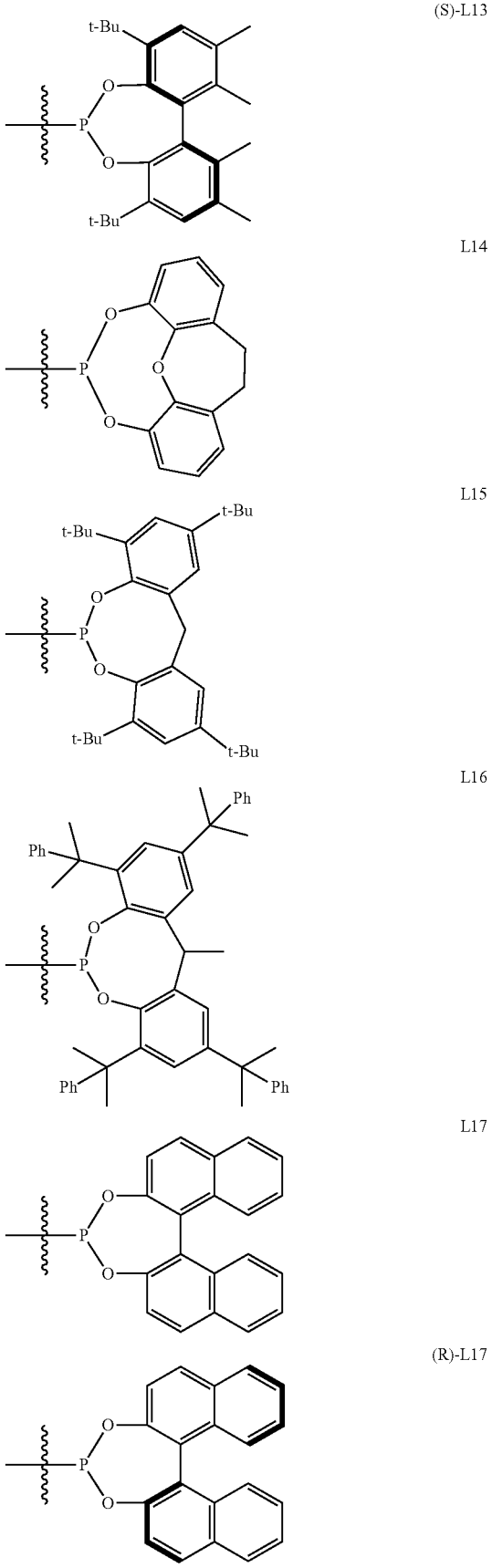

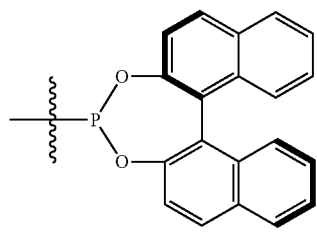
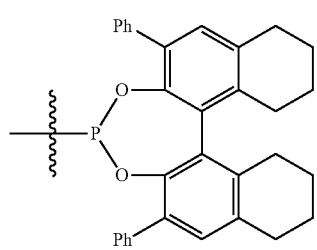
L18
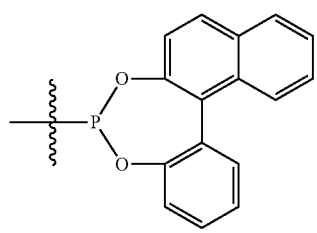
L19
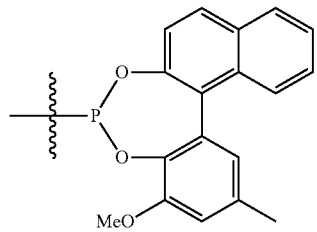
L20
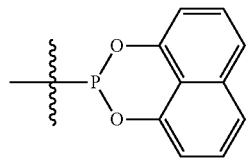
L21
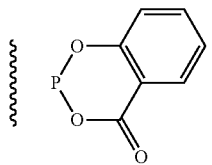
L22
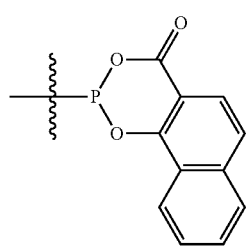
L23
(S)-L17
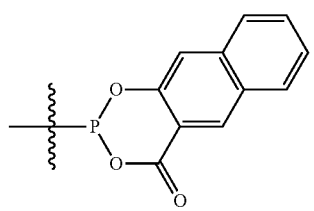
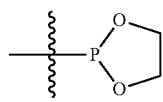
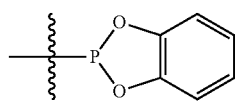
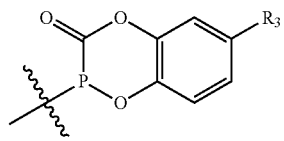
R³ = H, NO₂, Cl
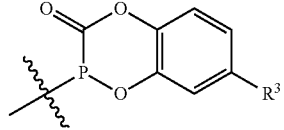
R³ = OMe, Cl
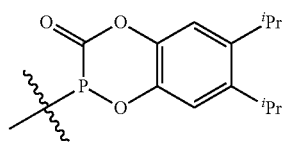
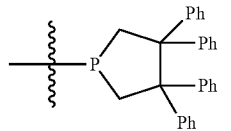
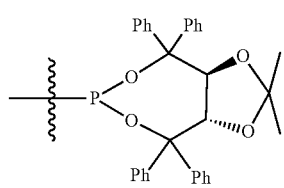
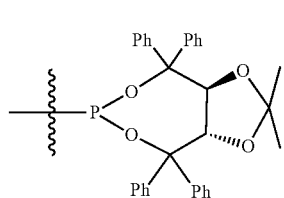
L24
L25
L26
L27
L28
L29
L30
L31
(R)-L31

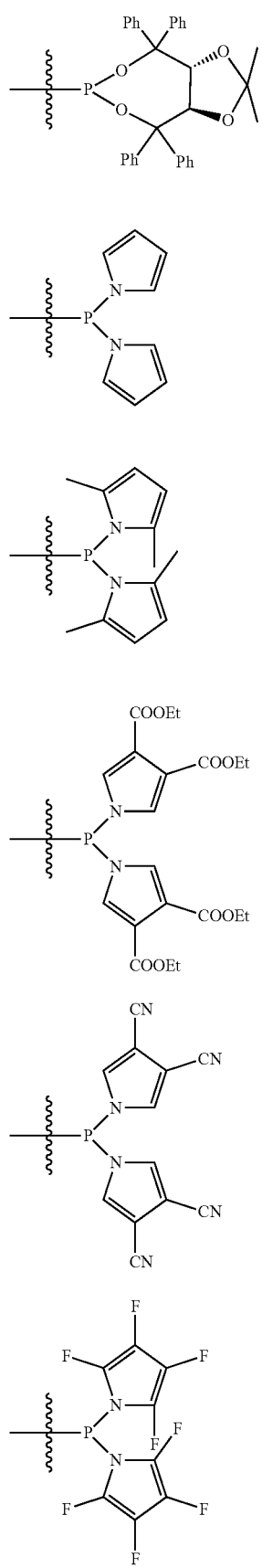
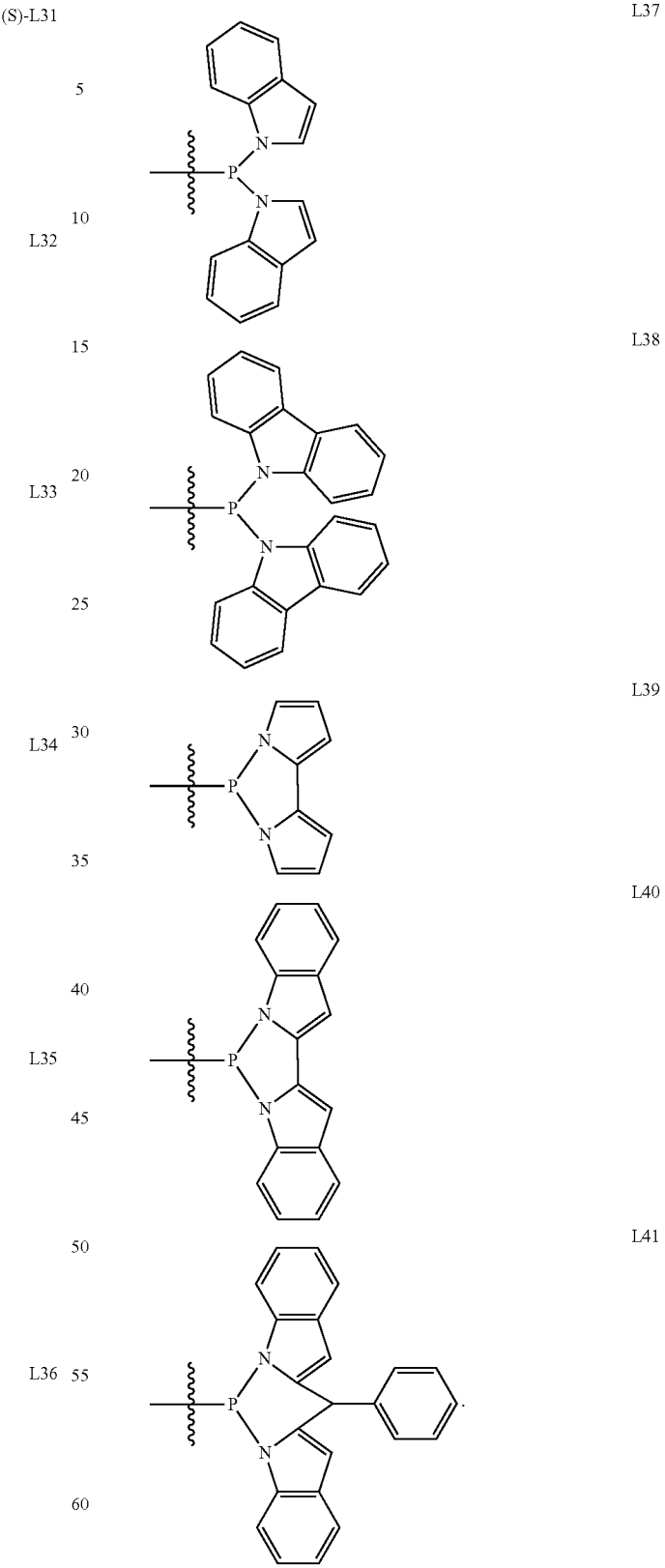
17. The method of claim 4, wherein the spiro-bisphosphorous compound of formula (III) is prepared through steps of:

subjecting isobutylene and proton to addition reaction in the catalysis of a protonic acid or a Lewis acid to obtain a tert-butyl carbocation; and subjecting the tert-butyl carbocation to alkylation with 3-methoxyphenol to obtain 2, 4-di-tert-butyl-5-methoxyphenol;
subjecting the 2, 4-di-tert-butyl-5-methoxyphenol to nucleophilic substitution with 1, 3-dichloro-2-propanol to obtain 2,4-di-tert-butyl-1,5-bis(3-methoxyphenoxy)-2-propanol;
subjecting the 2,4-di-tert-butyl-1,5-bis(3-methoxyphenoxy)-2-propanol to oxidation in the catalysis of chromium trioxide to obtain 2, 4-di-tert-butyl-1, 5-bis(3-methoxyphenoxy)-acetone;
subjecting the 2, 4-di-tert-butyl-1, 5-bis(3-methoxyphenoxy)-acetone to Friedel-Crafts reaction in the presence of a dehydrating agent to obtain 4,4',6,6'-tetra-tert-butyl-7, 7'-dimethoxy-1, 1'-spirodihydrobenzofuran;
subjecting the 4,4',6,6'-tetra-tert-butyl-7, 7'-dimethoxy-1, 1'-spirodihydrobenzofuran to demethylation in the presence of a demethylation agent to obtain 4,4',6,6'-tetra-tert-butyl-1, 1'-spirodihydrobenzofuran-7, 7'-diol;
sequentially adding the 4,4',6,6'-tetra-tert-butyl-1, 1'-spirodihydrobenzofuran-7, 7'-diol and an organic solvent to a reaction vessel under a nitrogen atmosphere to obtain a mixed solution; or sequentially adding the 4,4',6,6'-tetra-tert-butyl-1, 1'-spirodihydrobenzofuran-7, 7'-diol and an organic solvent to the reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and
dropwise adding a mixture composed of a chlorophosphite compound and an acid-binding agent to the mixed solution of the 1,1'-spirobiindane-7,7'-diol and the organic solvent followed by esterification at room temperature, filtration to remove inorganic salts, concentration and crystallization to obtain the spiro-bisphosphorous compound; or dropwise adding an organic solution of a chlorinated form of a phosphite to the lithiation product, followed by esterification, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

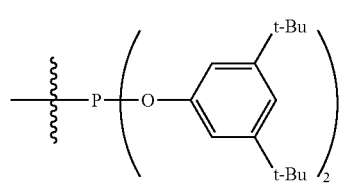

L1

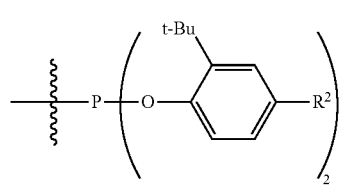

L2

$R^2$ = t-Bu, H, Me, OMe, $CF_3$, Cl

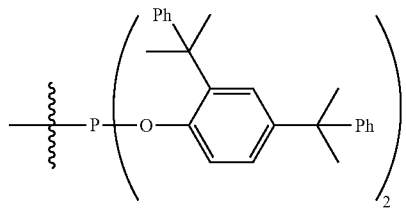

L3

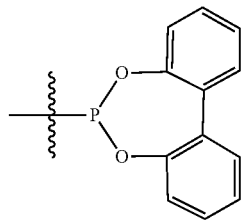

L4

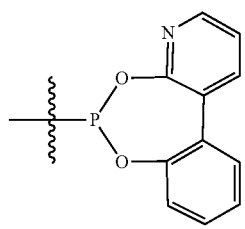

L5

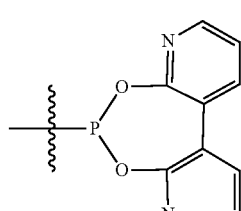

L6

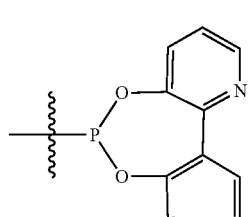

L7

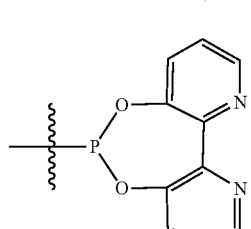

L8

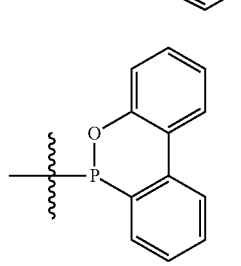

L9

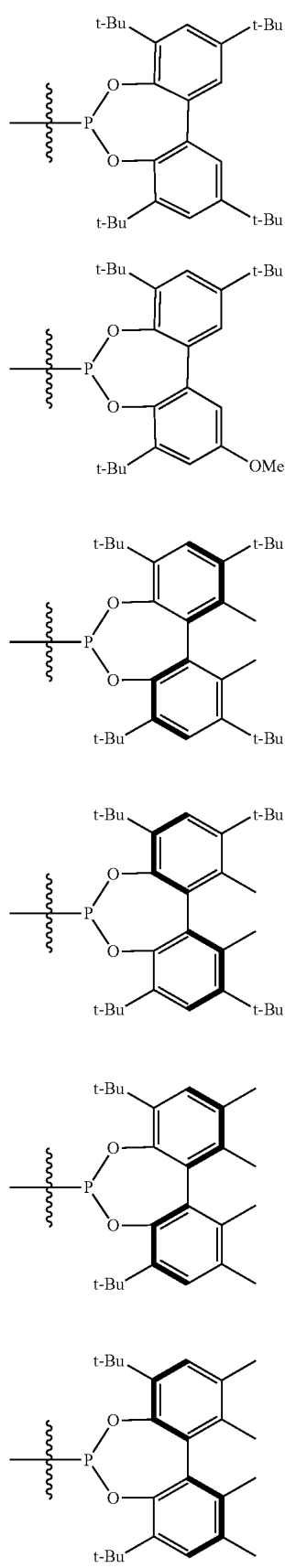
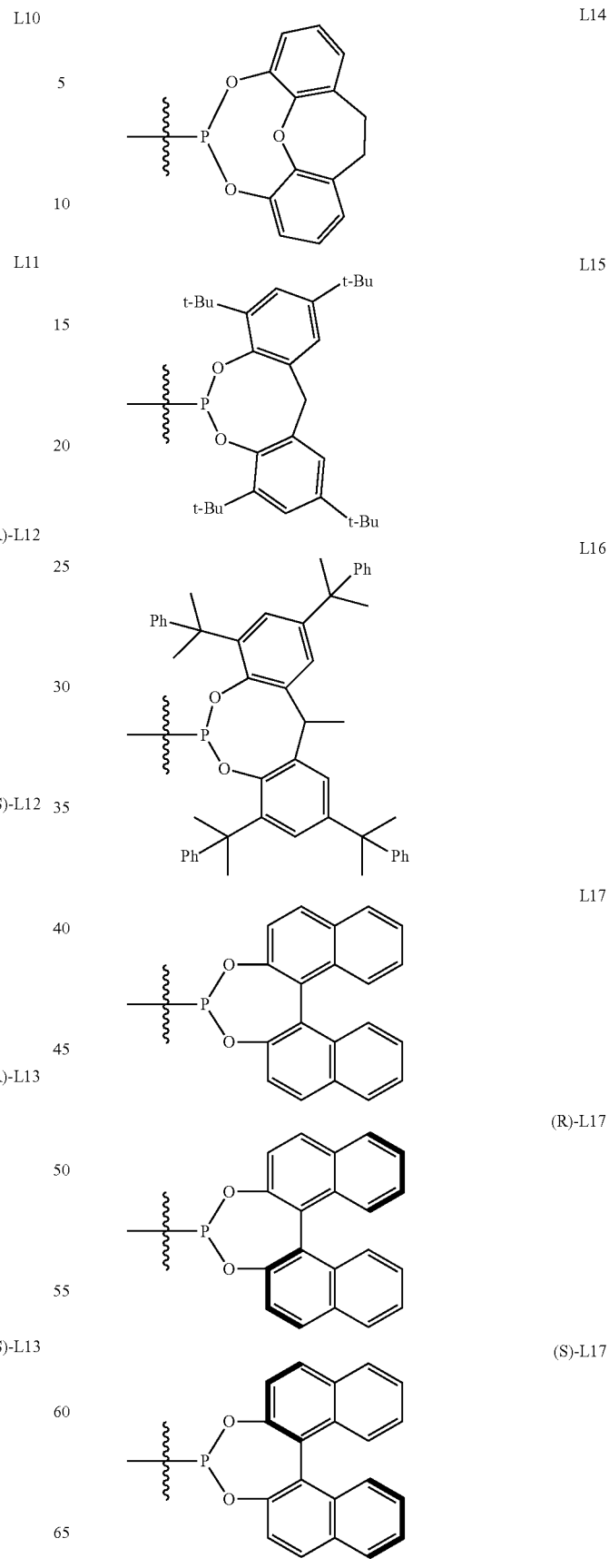

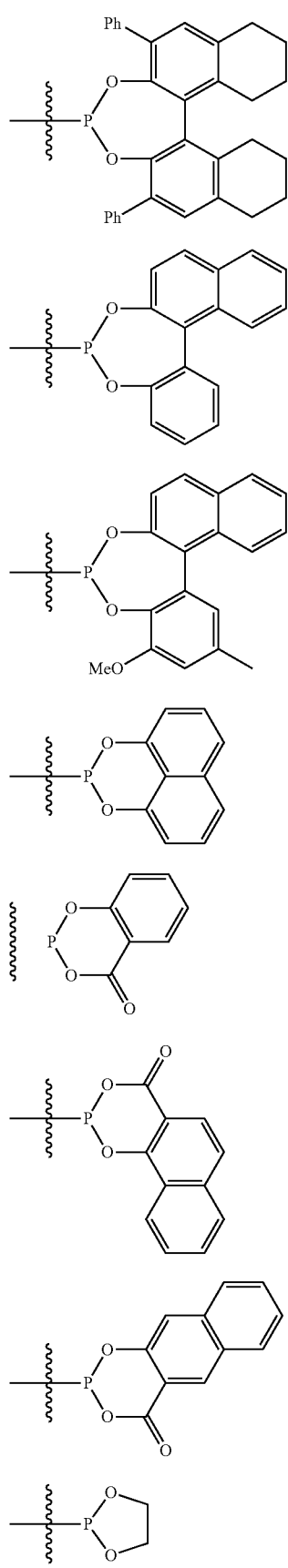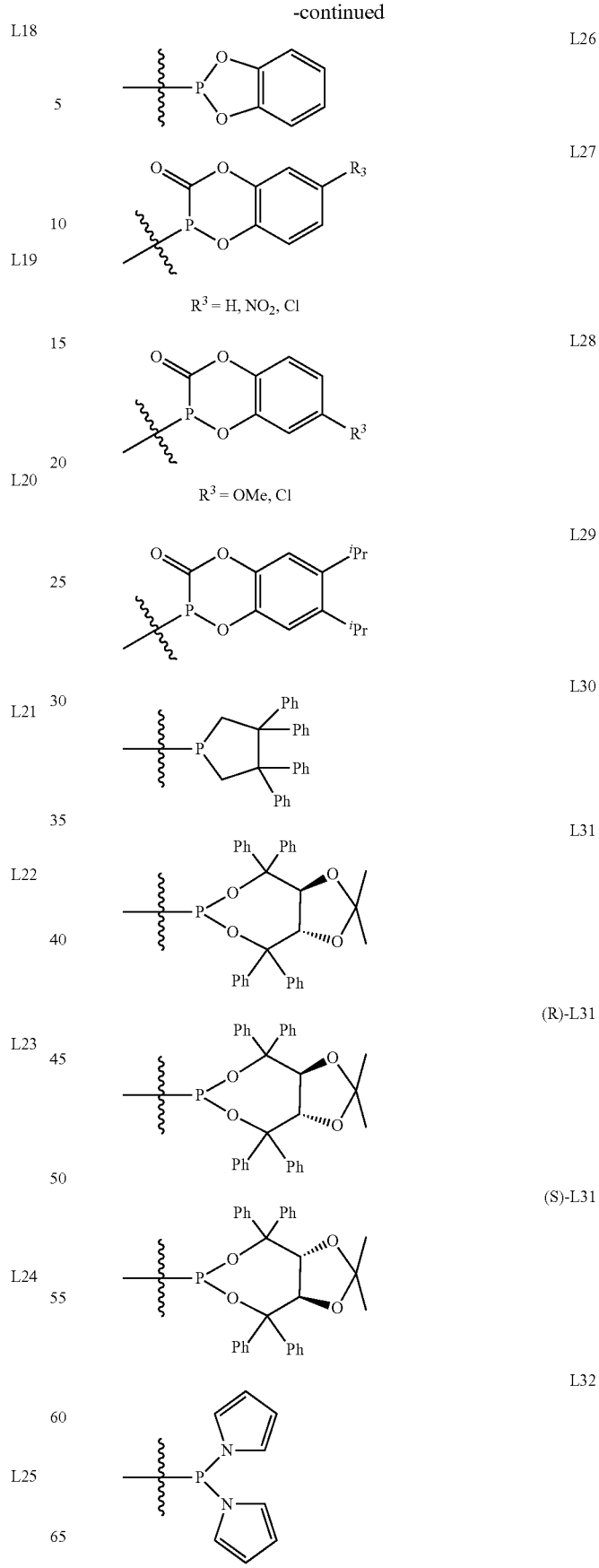

L33
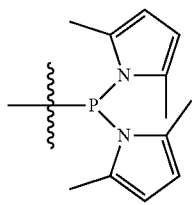

L34
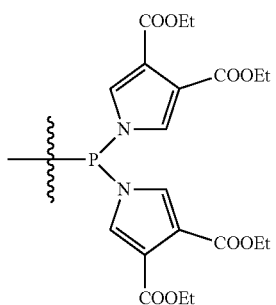

L35
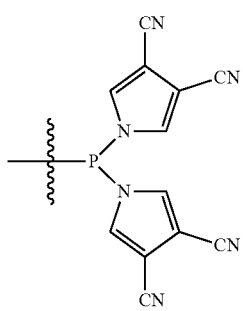

L36
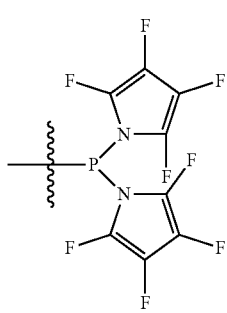

L37
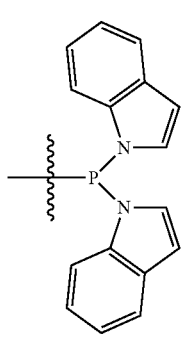

L38
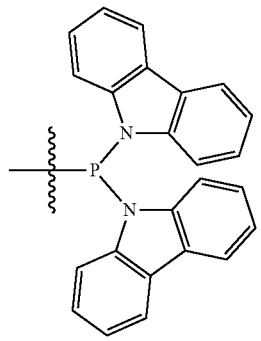

L39
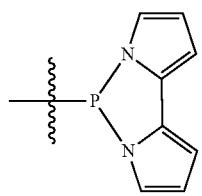

L40
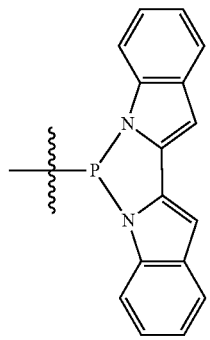

L41
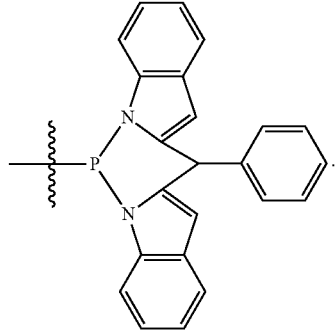

18. The method of claim 4, wherein the spiro-bisphosphorous compound of formula (III) is prepared through steps of:

subjecting isobutylene and proton to addition reaction in the catalysis of a protonic acid or a Lewis acid to obtain a tert-butyl carbocation; and subjecting the tert-butyl carbocation to alkylation with 3-methoxyphenol to obtain 2, 4-di-tert-butyl-5-methoxyphenol;

subjecting the 2, 4-di-tert-butyl-5-methoxyphenol to nucleophilic substitution with 2, 2-bis(chloromethyl)-1, 3-dioxolane to obtain 2, 4-di-tert-butyl-1, 5-bis(3-methoxyphenoxy)-2-propyl dioxolane;

subjecting the 2, 4-di-tert-butyl-1, 5-bis(3-methoxyphenoxy)-2-propyl dioxolane to Friedel-Crafts reaction in the presence of a dehydrating agent to obtain 4,4',6,6'-tetra-tert-butyl-7, 7'-dimethoxy-1, 1'-spirodihydrobenzofuran;

subjecting the 4,4',6,6'-tetra-tert-butyl-7, 7'-dimethoxy-1, 1'-spirodihydrobenzofuran to demethylation in the presence of a demethylation agent to obtain 4,4',6,6'-tetra-tert-butyl-1, 1'-spirodihydrobenzofuran-7, 7'-diol;

sequentially adding the 4,4',6,6'-tetra-tert-butyl-1, 1'-spirodihydrobenzofuran-7, 7'-diol and an organic solvent to a reaction vessel under a nitrogen atmosphere to obtain a mixed solution; or sequentially adding the 4,4',6,6'-tetra-tert-butyl-1, 1'-spirodihydrobenzofuran-7, 7'-diol and an organic solvent to a reaction vessel under a nitrogen atmosphere; dropwise adding n-butyllithium at −78~−10° C. to obtain a reaction mixture; and restoring the reaction mixture to room temperature followed by reaction under reflux to obtain a lithiation product; and dropwise adding a mixture of a chlorophosphite compound and an acid-binding agent to the mixed solution of the 1, 1'-spirobiindane-7, 7'-diol and the organic solvent followed by esterification at room temperature, filtration to remove inorganic salts, concentration and crystallization to obtain the spiro-bisphosphorous compound; or dropwise adding an organic solution of a chlorinated form of a phosphite to the lithiation product, followed by esterification, filtration to remove inorganic salts, concentration and crystallization to obtain the spiro-bisphosphorous compound, wherein the chlorophosphite compound comprises an aryl group selected from the group consisting of a biphenyl, methylene diphenyl, binaphthyl, benzoyloxy, o-phenyl, phenyl, and naphthyl group, and the phosphite is selected from the group consisting of:

L1
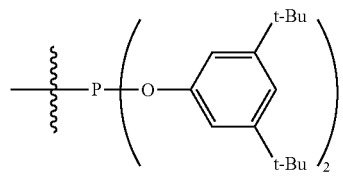

L2
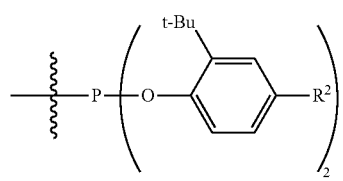

R² = t-Bu, H, Me, OMe, CF₃, Cl

L3
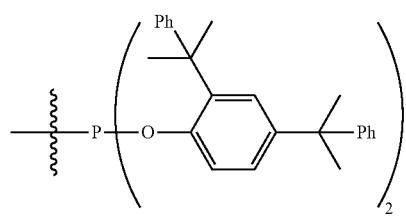

L4
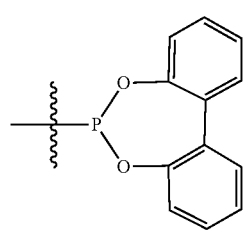

-continued

L5
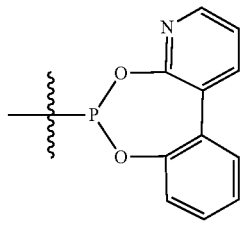

L6
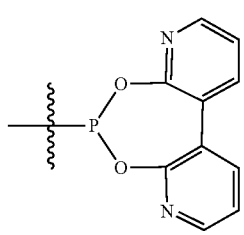

L7
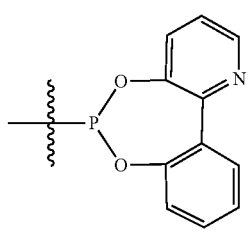

L8
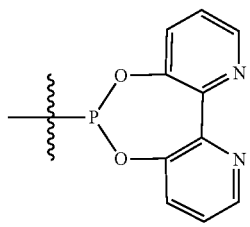

L9
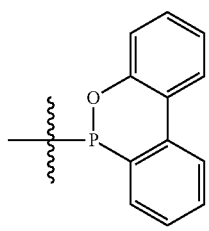

L10
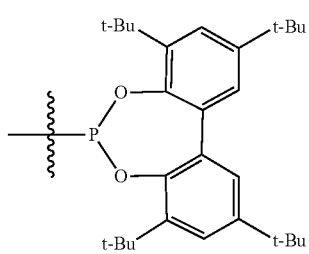

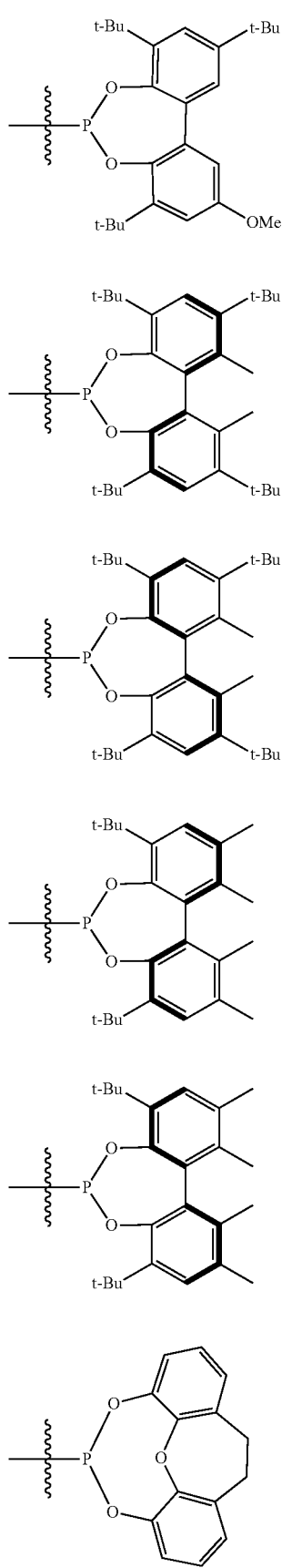

-continued
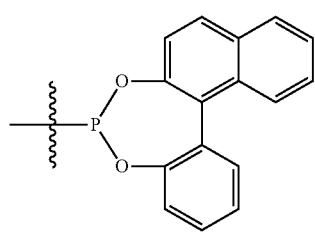
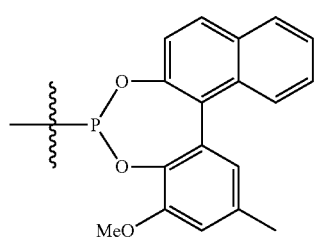
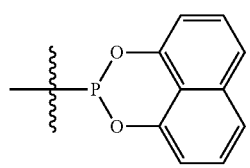 L21
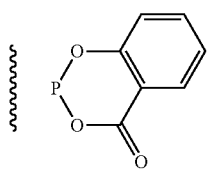 L22
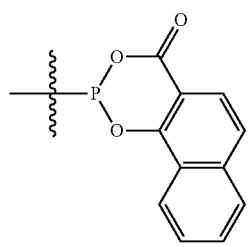 L23
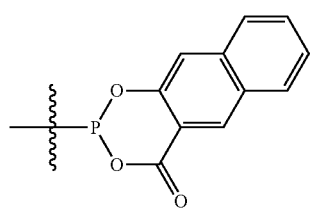 L24
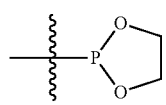 L25
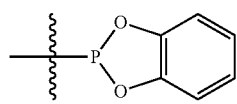 L26
-continued
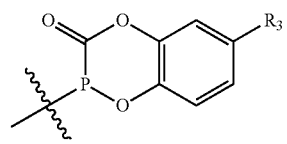 L27
$R^3$ = H, NO$_2$, Cl
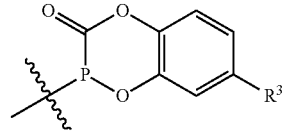 L28
$R^3$ = OMe, Cl
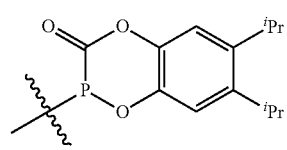 L29
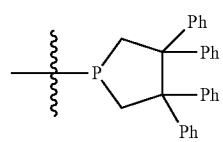 L30
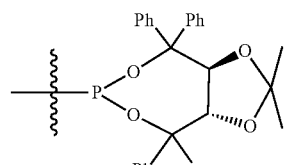 L31
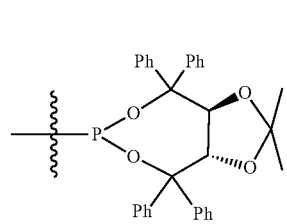 (R)-L31
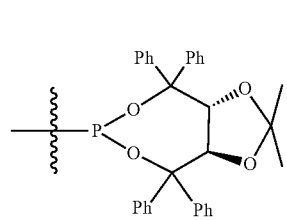 (S)-L31
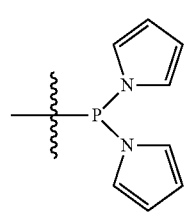 L32

L33 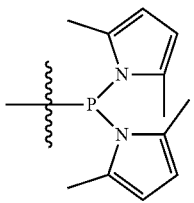

L34 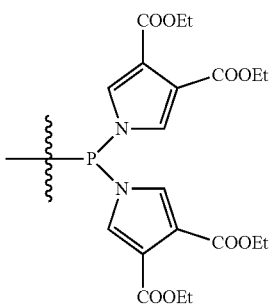

L35 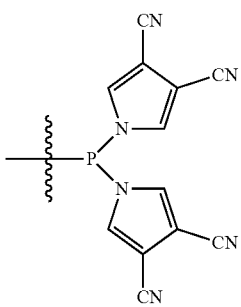

L36 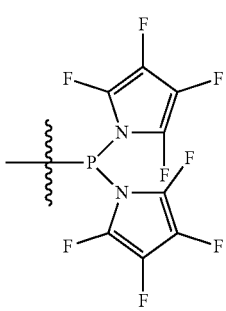

L37 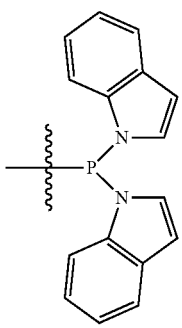

L38 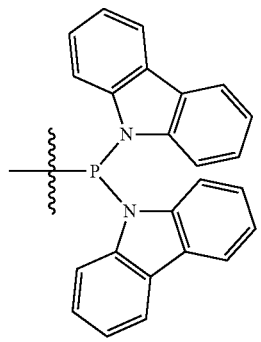

L39 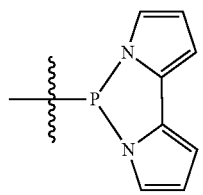

L40 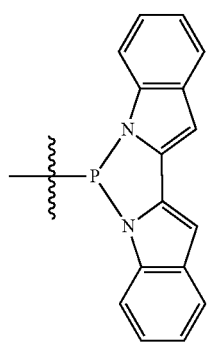

L41 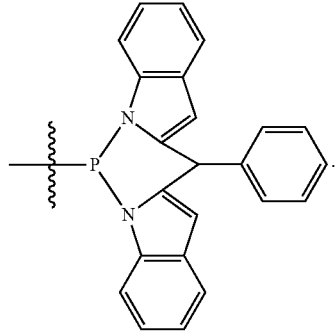

19. A method for catalyzing carbonylation related reactions, comprising:
   sequentially adding the spiro-bisphosphorous compound of claim 1 and a transition metal catalyst to an organic solvent in a reaction vessel under the protection of an inert gas followed by stirring at room temperature for complexation, wherein a molar ratio of phosphine in the spiro-bisphosphorous compound to the transition metal catalyst is (1-5):1;
   under the protection of an inert gas, adding liquified etherified C4, methanol-to-olefins (MTO) C4, cis-2-butene or trans-2-butene to the reaction vessel followed by stirring at room temperature, wherein a concentration of the transition metal catalyst is controlled at 50-200 ppm; and
   feeding hydrogen and carbon monoxide into the reaction vessel followed by reaction under stirring at 40-100° C.

for 1-4 h, wherein a pressure ratio of the hydrogen to the carbon monoxide is 1:(1-5), and a total pressure of hydrogen and carbon monoxide is controlled at 0.5-1 MPa.

20. The method of claim 19, wherein the etherified C4 and the MTO C4 independently consist of 0-30 wt % of 1-butene, 0-70 wt % of trans-2-butene, 0-40 wt % of cis-2-butene, 0-30 wt % of n-butane, 0-20 wt % of isobutane and 0-10 wt % of isobutylene.

* * * * *